(12) United States Patent
Matsui et al.

(10) Patent No.: US 6,589,963 B2
(45) Date of Patent: Jul. 8, 2003

(54) HETEROCYCLIC COMPOUNDS AND SALTS THEREOF AND MEDICINAL USE OF THE SAME

(75) Inventors: Hiroshi Matsui, Nara (JP); Hideo Kobayashi, Uji (JP); Satoru Azukizawa, Kyoto (JP); Masayasu Kasai, Souraku-gun (JP); Akihisa Yoshimi, Takatsuki (JP); Hiroaki Shirahase, Nagaokakyo (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 10/148,386

(22) PCT Filed: Nov. 29, 2000

(86) PCT No.: PCT/JP00/08464

§ 371 (c)(1),
(2), (4) Date: May 31, 2002

(87) PCT Pub. No.: WO01/40192

PCT Pub. Date: Jun. 7, 2001

(65) Prior Publication Data

US 2003/0027836 A1 Feb. 6, 2003

(30) Foreign Application Priority Data

Dec. 3, 1999 (JP) .......................................... 11-345543
Sep. 27, 2000 (JP) ........................................ 2000-295108

(51) Int. Cl.⁷ .................... C07D 401/12; A61K 31/47
(52) U.S. Cl. ........................................ 514/307; 546/147
(58) Field of Search .......................... 546/147; 514/307

(56) References Cited

U.S. PATENT DOCUMENTS

| | | | |
|---|---|---|---|
| 4,572,912 A | 2/1986 | Yoshioka et al. | 514/369 |
| 4,687,777 A | 8/1987 | Meguro et al. | 514/342 |
| 5,002,953 A | 3/1991 | Hindley | 514/275 |

FOREIGN PATENT DOCUMENTS

| | | |
|---|---|---|
| WO | 93/23378 | 11/1993 |
| WO | 98/00403 | 1/1998 |

OTHER PUBLICATIONS

M. Faul et al., "Synthesis of 2–Phenyloxazole Derivatives Containing Amino Acids as Insulin Sensitivity Enhancers for Treatment of Type II Diabetes", Heterocycles, vol. 55, No. 4, pp. 689–704, 2001.

Primary Examiner—Zinna Northington Davis
(74) Attorney, Agent, or Firm—Wenderoth, Lind & Ponack, L.L.P.

(57) ABSTRACT

A heterocyclic compound of the formula [I]

$$Y-A-B-O-\text{[aromatic ring]}-CO_2R^1, \quad N-R^2, \quad R^3 \quad [I]$$

wherein $R^1$ is hydrogen atom or lower alkyl, $R^2$ is hydrogen atom, alkyl optionally having a substituent and the like, $R^3$ is hydrogen atom, lower alkyl and the like, A is a single bond or $>N-R^5$ wherein $R^5$ is hydrogen atom or lower alkyl, B is lower alkylene, and Y is aryl optionally having a substituent and the like, and a pharmaceutically acceptable salt thereof show a hypoglycemic action, a blood hypolipidemic action, an insulin resistance-improving action and a PPAR activating action, and are useful as a hypoglycemic agent, a hypolipidemic agent, an insulin resistance improver, a therapeutic agent of diabetes, a therapeutic agent of diabetic complication, a glucose tolerance improver, an anti-atherosclerosis agent, an anti-obesity agent, an antiinflammatory agent, an agent for the prophylaxis or treatment of PPAR-mediated disease and an agent for the prophylaxis or treatment of syndrome X.

18 Claims, No Drawings

HETEROCYCLIC COMPOUNDS AND SALTS THEREOF AND MEDICINAL USE OF THE SAME

This application is a 371 of PCT/JP00/08464 filed Nov. 29, 2000.

TECHNICAL FIELD OF THE INVENTION

The present invention relates to a novel heterocyclic compound and a pharmaceutically acceptable salt thereof, which have a hypoglycemic action, a blood hypolipidemic action, an insulin resistance-improving action or a PPAR (peroxisome proliferator-activated receptor)-activating action. The present invention also relates to a pharmaceutical composition comprising the above-mentioned novel heterocyclic compound or a pharmaceutically acceptable salt thereof. Furthermore, the present invention relates to a hypoglycemic agent, a hypolipidemic agent, an insulin resistance improver, a therapeutic agent of diabetes, an anti-diabetic complication agent (i.e., a therapeutic agent of diabetic complication), a glucose tolerance improver, an anti-atherosclerosis agent, an anti-obesity agent, an antiinflammatory agent, an agent for the prophylaxis or treatment of PPAR-mediated disease and an agent for the prophylaxis or treatment of syndrome X, all of which comprising the above-mentioned novel heterocyclic compound or a pharmaceutically acceptable salt thereof.

BACKGROUND OF THE INVENTION

As a therapeutic agent of diabetes, biguanide compounds having, as a main action, an inhibitory action on glucose absorption via the intestinal tract and on glucose release from the liver, sulfonylurea compounds having an accelerating action on insulin secretion as a main action, insulin and the like have been employed. However, biguanide compounds cause lactic acidosis, and sulfonylurea compounds sometimes cause serious hypoglycemia due to their strong hypoglycemic action. Therefore, a due care should be given when in use of these compounds. In recent years, there have been active researches and developments of a therapeutic agent of diabetes, which is free of these defects, with the consequence that various compounds having an insulin resistance-improving action have been found.

The insulin resistance is important as a cause of non-insulin dependent diabetes mellitus (NIDDM), along with decrease in the insulin secretion. Therefore, the development of a pharmaceutical agent that improves insulin resistance has been desired. Various thiazolidine compounds are known as the agent capable of improving the insulin resistance. As these compounds, for example, 5-[4-[(6-hydroxy-2,5,7,8-tetramethylchroman-2-yl)methoxy]benzyl]-2,4-thiazolidinedione (general name: troglitazone) is described in JP-B-2-31079, 5-[[4-[2-(5-ethyl-pyridin-2-yl)ethoxy]phenyl]methyl]-2,4-thiazolidinedione (general name: pioglitazone) is described in JP-B-5-66956, and 5-[[4-[2-[N-methyl-N-(pyridin-2-yl)amino]ethoxy]phenyl]methyl]-2,4-thiazolidinedione (general name: rosiglitazone) is described in JP-A-1-131169.

It is therefore an object of the present invention to provide a compound having a hypoglycemic action, a blood hypolipidemic action, an insulin resistance-improving action and a PPAR activating action, which has a structure completely different from that of conventional compounds, thereby to increase the diversity in and to broaden the range of selection from hypoglycemic agents, hypolipidemic agents, insulin resistance improvers, therapeutic agents of diabetes, therapeutic agents of diabetic complications, glucose tolerance improvers, anti-atherosclerosis agents, anti-obesity agents, antiinflammatory agents, agents for the prophylaxis or treatment of PPAR-mediated disease and agents for the prophylaxis or treatment of syndrome X.

DISCLOSURE OF THE INVENTION

The present inventors have conducted intensive studies in an attempt to solve the above-mentione problems and found that a heterocyclic compound having a novel structure of the formula [I]

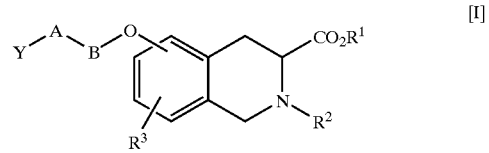

wherein
$R^1$ is hydrogen atom or lower alkyl,
$R^2$ is hydrogen atom, alkyl optionally having a substituent, cycloalkyl, cycloalkylalkyl, aryl optionally having a substituent, arylalkyl optionally having a substituent, alkenyl optionally having a substituent, alkynyl optionally having a substituent, heterocyclic alkyl optionally having a substituent or —$COR^4$
  wherein $R^4$ is hydrogen atom, alkyl optionally having a substituent, aryl optionally having a substituent, alkenyl optionally having a substituent, arylalkyl optionally having a substituent or heterocyclic residue optionally having a substituent,
$R^3$ is hydrogen atom, lower alkyl or lower alkoxy,
A is a single bond or >N—$R^5$ wherein $R^5$ is hydrogen atom or lower alkyl,
B is lower alkylene, and
Y is aryl optionally having a substituent or an aromatic heterocyclic residue optionally having a substituent and a pharmaceutically acceptable salt thereof have a hypoglycemic action, a blood hypolipidemic action, an insulin resistance-improving action and a PPAR activating action, which resulted in the completion of the invention.

Accordingly, the present invention relates to the following.

[1] A heterocyclic compound of the formula [I]

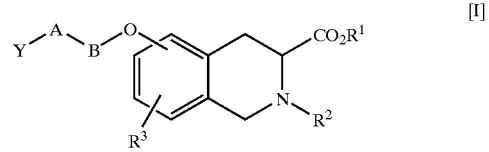

wherein
$R^1$ is hydrogen atom or lower alkyl,
$R^2$ is hydrogen atom, alkyl optionally having a substituent, cycloalkyl, cycloalkylalkyl, aryl optionally having a substituent, arylalkyl optionally having a substituent, alkenyl optionally having a substituent, alkynyl optionally having a substituent, heterocyclic alkyl optionally having a substituent or —$COR^4$
  wherein $R^4$ is hydrogen atom, alkyl optionally having a substituent, aryl optionally having a substituent, alkenyl optionally having a substituent, arylalkyl optionally having a substituent or heterocyclic residue optionally having a substituent $R^3$ is hydrogen atom, lower alkyl or lower alkoxy, A is a single bond or >N—$R^5$ wherein $R^5$ is hydrogen atom or lower alkyl, B is lower alkylene, and Y is aryl optionally having a substituent or an aromatic heterocyclic residue optionally having a substituent (hereinafter to be referred to as heterocyclic compound [I]), and a pharmaceutically acceptable salt thereof;

[2] the heterocyclic compound of the above-mentioned [1] wherein, in the formula [I], $R^1$ is hydrogen atom or lower alkyl, $R^2$ is hydrogen atom, alkyl optionally having a substituent, cycloalkyl, cycloalkylalkyl, aryl optionally having a substituent, arylalkyl optionally having a substituent or —$COR^4$ wherein $R^4$ is hydrogen atom, alkyl optionally having a substituent, aryl optionally having a substituent or arylalkyl optionally having a substituent, $R^3$ is hydrogen atom, lower alkyl or lower alkoxy, A is a single bond or >N—$R^5$ wherein $R^5$ is hydrogen atom or lower alkyl, B is lower alkylene, and Y is aryl optionally having a substituent or an aromatic heterocyclic residue optionally having a substituent, and a pharmaceutically acceptable salt thereof;

[3] the heterocyclic compound of the above-mentioned [1] wherein, in the formula [I], $R^1$ is hydrogen atom or lower alkyl, $R^2$ is hydrogen atom, alkyl, cycloalkylalkyl, arylalkyl optionally having a substituent, alkenyl, alkynyl, heterocyclic alkyl or —$COR^4$ wherein $R^4$ is alkyl, alkenyl or aryl, $R^3$ is hydrogen atom or lower alkoxy, A is a single bond or >N—$R^5$ wherein $R^5$ is lower alkyl, B is lower alkylene, and Y is aryl or an aromatic heterocyclic residue optionally having a substituent, and a pharmaceutically acceptable salt thereof;

[4] the heterocyclic compound of the above-mentioned [1] wherein, in the formula [I], $R^1$ is hydrogen atom or lower alkyl, $R^2$ is hydrogen atom, alkyl, cycloalkylalkyl, arylalkyl optionally having a substituent or —$COR^4$ wherein $R^4$ is alkyl or aryl, $R^3$ is hydrogen atom, A is a single bond or >N—$R^5$ wherein $R^5$ is lower alkyl, B is lower alkylene, and Y is an aromatic heterocyclic residue optionally having a substituent, and a pharmaceutically acceptable salt thereof;

[5] the heterocyclic compound of the above-mentioned [1] wherein, in the formula [I], Y—A— is

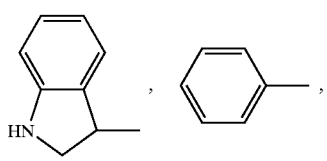

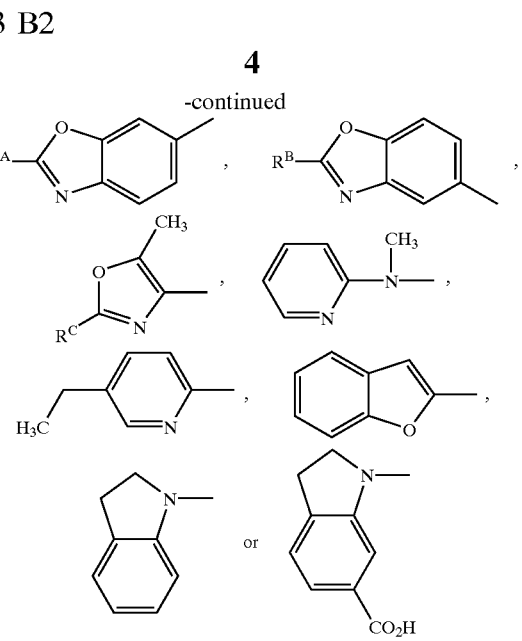

wherein $R^A$ is isopropyl or tert-butyl, $R^B$ is isopropyl or tert-butyl, $R^C$ is isopropyl, tert-butyl, phenyl, thiophen-2-yl, 2-methylpropenyl, 3-butenyl, cyclopropyl, 1-butenyl or 2,2-dimethylpropyl, and a pharmaceutically acceptable salt thereof;

[6] the heterocyclic compound of the above-mentioned [1] wherein, in the formula [I], Y—A— is

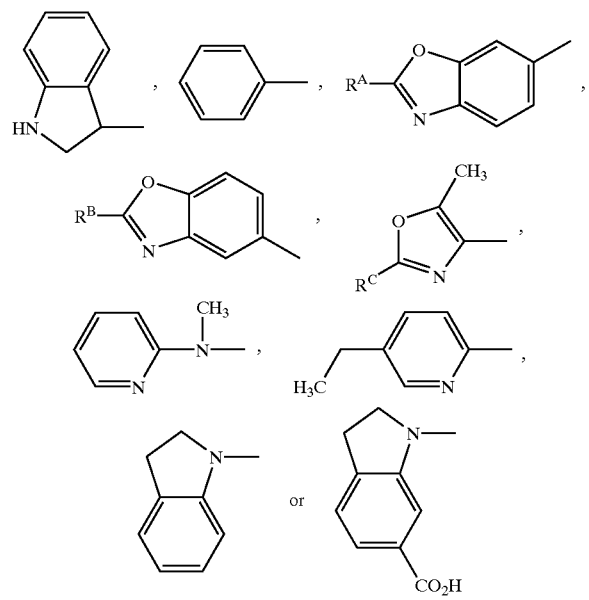

wherein $R^A$ is isopropyl or tert-butyl, $R^B$ is isopropyl or tert-butyl, $R^C$ is isopropyl, tert-butyl, phenyl, thiophen-2-yl, 2-methylpropenyl or 3-butenyl, and a pharmaceutically acceptable salt thereof;

[7] the heterocyclic compound of the above-mentioned [1] wherein, in the formula [I], Y—A— is

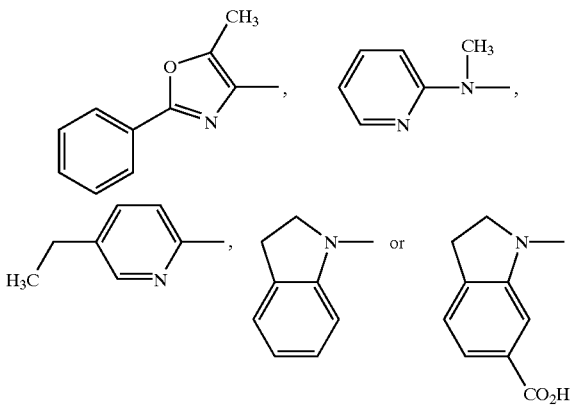

and a pharmaceutically acceptable salt thereof;

[8] the heterocyclic compound of the above-mentioned [1] wherein, in the formula [I], Y—A— is

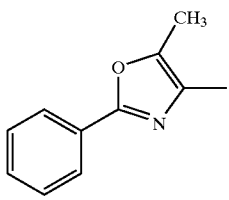

and a pharmaceutically acceptable salt thereof;

[9] the heterocyclic compound of the above-mentioned [1] wherein the heterocyclic compound of the formula [I] is any of the following compounds (1) to (67):
(1) 7-[2-(5-methyl-2-phenyloxazol-4-yl)ethoxy]-1,2,3,4-tetrahydroisoquinoline-(3S)-carboxylic acid,
(2) 2-benzyl-7-[2-(5-methyl-2-phenyloxazol-4-yl)ethoxy]-1,2,3,4-tetrahydroisoquinoline-(3S)-carboxylic acid,
(3) 2-acetyl-7-[2-(5-methyl-2-phenyloxazol-4-yl)ethoxy]-1,2,3,4-tetrahydroisoquinoline-(3S)-carboxylic acid,
(4) 2-methyl-7-[2-(5-methyl-2-phenyloxazol-4-yl)ethoxy]-1,2,3,4-tetrahydroisoquinoline-(3S)-carboxylic acid,
(5) 2-hexanoyl-7-[2-(5-methyl-2-phenyloxazol-4-yl)ethoxy]-1,2,3,4-tetrahydroisoquinoline-(3S)-carboxylic acid,
(6) 2-hexyl-7-[2-(5-methyl-2-phenyloxazol-4-yl)ethoxy]-1,2,3,4-tetrahydroisoquinoline-(3S)-carboxylic acid,
(7) 2-isobutyl-7-[2-(5-methyl-2-phenyloxazol-4-yl)ethoxy]-1,2,3,4-tetrahydroisoquinoline-(3S)-carboxylic acid,
(8) 2-cyclohexylmethyl-7-[2-(5-methyl-2-phenyloxazol-4-yl)ethoxy]-1,2,3,4-tetrahydroisoquinoline-(3S)-carboxylic acid,
(9) 7-[2-(5-methyl-2-phenyloxazol-4-yl)ethoxy]-2-(3-phenylpropyl)-1,2,3,4-tetrahydroisoquinoline-(3S)-carboxylic acid,
(10) 2-benzoyl-7-[2-(5-methyl-2-phenyloxazol-4-yl)ethoxy]-1,2,3,4-tetrahydroisoquinoline-(3S)-carboxylic acid,
(11) 2-benzyl-7-[2-(N-methyl-N-(pyridin-2-yl)amino)ethoxy]-1,2,3,4-tetrahydroisoquinoline-(3S)-carboxylic acid,
(12) 2-benzyl-7-[2-(5-ethyl-pyridin-2-yl)ethoxy]-1,2,3,4-tetrahydroisoquinoline-(3S)-carboxylic acid,
(13) 2-benzyl-7-[2-(indolin-1-yl)ethoxy]-1,2,3,4-tetrahydroisoquinoline-(3S)-carboxylic acid,
(14) ethyl 2-benzyl-7-[2-(5-methyl-2-phenyloxazol-4-yl)ethoxy]-1,2,3,4-tetrahydroisoquinoline-(3S)-carboxylate,
(15) methyl 7-[2-(5-methyl-2-phenyloxazol-4-yl)ethoxy]-1,2,3,4-tetrahydroisoquinoline-(3S)-carboxylate,
(16) 2-(4-methoxybenzyl)-7-[2-(5-methyl-2-phenyloxazol-4-yl)ethoxy]-1,2,3,4-tetrahydroisoquinoline-(3S)-carboxylic acid,
(17) ethyl 2-(4-methoxybenzyl)-7-[2-(5-methyl-2-phenyloxazol-4-yl)ethoxy]-1,2,3,4-tetrahydroisoquinoline-(3S)-carboxylate,
(18) 2-(4-methylbenzyl)-7-[2-(5-methyl-2-phenyloxazol-4-yl)ethoxy]-1,2,3,4-tetrahydroisoquinoline-(3S)-carboxylic acid,
(19) ethyl 2-(4-methylbenzyl)-7-[2-(5-methyl-2-phenyloxazol-4-yl)ethoxy]-1,2,3,4-tetrahydroisoquinoline-(3S)-carboxylate,
(20) 2-benzyl-7-[2-(6-carboxyindolin-1-yl)ethoxy]-1,2,3,4-tetrahydroisoquinoline-(3S)-carboxylic acid,
(21) 2-(4-fluorobenzyl)-7-[2-(5-methyl-2-phenyloxazol-4-yl)ethoxy]-1,2,3,4-tetrahydroisoquinoline-(3S)-carboxylic acid,
(22) 2-(2,2-dimethylpropionyl)-7-[2-(5-methyl-2-phenyloxazol-4-yl)ethoxy]-1,2,3,4-tetrahydroisoquinoline-(3S)-carboxylic acid,
(23) 2-(2,2-dimethylpropyl)-7-[2-(5-methyl-2-phenyloxazol-4-yl)ethoxy]-1,2,3,4-tetrahydroisoquinoline-(3S)-carboxylic acid,
(24) 2-benzyl-7-[2-(5-methyl-2-tert-butyloxazol-4-yl)ethoxy]-1,2,3,4-tetrahydroisoquinoline-(3S)-carboxylic acid,
(25) 2-benzyl-7-[2-(5-methyl-2-(thiophen-2-yl)oxazol-4-yl)ethoxy]-1,2,3,4-tetrahydroisoquinoline-(3S)-carboxylic acid,
(26) 2-benzyl-7-[2-(5-methyl-2-isopropyloxazol-4-yl)ethoxy]-1,2,3,4-tetrahydroisoquinoline-(3S)-carboxylic acid,
(27) 2-butyl-7-[2-(5-methyl-2-phenyloxazol-4-yl)ethoxy]-1,2,3,4-tetrahydroisoquinoline-(3S)-carboxylic acid,
(28) 2-benzyl-7-{2-[5-methyl-2-(2-methylpropenyl)oxazol-4-yl]ethoxy}-1,2,3,4-tetrahydroisoquinoline-(3S)-carboxylic acid,
(29) 2-benzyl-7-{2-[2-(3-butenyl)-5-methyloxazol-4-yl]ethoxy}-1,2,3,4-tetrahydroisoquinoline-(3S)-carboxylic acid,
(30) 2-allyl-7-[2-(5-methyl-2-phenyloxazol-4-yl)ethoxy]-1,2,3,4-tetrahydroisoquinoline-(3S)-carboxylic acid,
(31) 7-[2-(5-methyl-2-phenyloxazol-4-yl)ethoxy]-2-(2-propynyl)-1,2,3,4-tetrahydroisoquinoline-(3S)-carboxylic acid,
(32) 2-(2-butenyl)-7-[2-(5-methyl-2-phenyloxazol-4-yl)ethoxy]-1,2,3,4-tetrahydroisoquinoline-(3S)-carboxylic acid,
(33) 2-benzyl-7-[(indolin-3-yl)ethoxy]-1,2,3,4-tetrahydroisoquinoline-(3S)-carboxylic acid,
(34) 2-(3-butenyl)-7-[2-(5-methyl-2-phenyloxazol-4-yl)ethoxy]-1,2,3,4-tetrahydroisoquinoline-(3S)-carboxylic acid,
(35) 7-[2-(5-methyl-2-phenyloxazol-4-yl)ethoxy]-2-pentanoyl-1,2,3,4-tetrahydroisoquinoline-(3S)-carboxylic acid,
(36) 7-[2-(5-methyl-2-phenyloxazol-4-yl)ethoxy]-2-(4-pentenoyl)-1,2,3,4-tetrahydroisoquinoline-(3S)-carboxylic acid,
(37) 2-(3-methyl-2-butenoyl)-7-[2-(5-methyl-2-phenyloxazol-4-yl)ethoxy]-1,2,3,4-tetrahydroisoquinoline-(3S)-carboxylic acid,
(38) 2-(3,3-dimethylbutyryl)-7-[2-(5-methyl-2-phenyloxazol-4-yl)ethoxy]-1,2,3,4-tetrahydroisoquinoline-(3S)-carboxylic acid,

(39) 2-benzyl-7-methoxy-6-[2-(5-methyl-2-phenyloxazol-4-yl)ethoxy]-1,2,3,4-tetrahydroisoquinoline-(3RS)-carboxylic acid,
(40) 7-[2-(5-methyl-2-phenyloxazol-4-yl)ethoxy]-2-(pyridin-2-ylmethyl)-1,2,3,4-tetrahydroisoquinoline-(3S)-carboxylic acid,
(41) 2-benzyl-7-(3-methyl-3-phenylbutoxy)-1,2,3,4-tetrahydroisoquinoline-(3S)-carboxylic acid,
(42) 2-benzyl-7-(3,3-dimethyl-4-phenylbutoxy)-1,2,3,4-tetrahydroisoquinoline-(3S)-carboxylic acid,
(43) 2-benzyl-7-(2-isopropylbenzoxazol-6-yl)methoxy-1,2,3,4-tetrahydroisoquinoline-(3S)-carboxylic acid,
(44) 2-benzyl-7-(2-tert-butylbenzoxazol-6-yl)methoxy-1,2,3,4-tetrahydroisoquinoline-(3S)-carboxylic acid,
(45) 2-benzyl-7-(2-tert-butylbenzoxazol-5-yl)methoxy-1,2,3,4-tetrahydroisoquinoline-(3S)-carboxylic acid,
(46) 7-(2-tert-butylbenzoxazol-6-yl)methoxy-2-(2,2-dimethylpropyl)-1,2,3,4-tetrahydroisoquinoline-(3S)-carboxylic acid,
(47) 2-benzyl-7-(2-isopropylbenzoxazol-5-yl)methoxy-1,2,3,4-tetrahydroisoquinoline-(3S)-carboxylic acid,
(48) 7-[2-(5-methyl-2-phenyloxazol-4-yl)ethoxy]-2-(pyridin-4-ylmethyl)-1,2,3,4-tetrahydroisoquinoline-(3S)-carboxylic acid,
(49) 7-[2-(5-methyl-2-phenyloxazol-4-yl)ethoxy]-2-[(pyridin-2-yl)carbonyl]-1,2,3,4-tetrahydroisoquinoline-(3S)-carboxylic acid,
(50) methyl 2-benzyl-7-[2-(5-methyl-2-phenyloxazol-4-yl)ethoxy]-1,2,3,4-tetrahydroisoquinoline-(3S)-carboxylate,
(51) 2-benzyl-7-[2-(2-cyclopropyl-5-methyloxazol-4-yl)-ethoxy]-1,2,3,4-tetrahydroisoquinoline-(3S)-carboxylic acid,
(52) 2-(3-methyl-2-butenyl)-7-[2-(5-methyl-2-phenyloxazol-4-yl)ethoxy]-1,2,3,4-tetrahydroisoquinoline-(3S)-carboxylic acid,
(53) 2-(2,2-dimethylpropyl)-7-[2-(5-methyl-2-tert-butyloxazol-4-yl)ethoxy]-1,2,3,4-tetrahydroisoquinoline-(3S)-carboxylic acid,
(54) 2-benzyl-7-{2-[2-(1-butenyl)-5-methyloxazol-4-yl]ethoxy}-1,2,3,4-tetrahydroisoquinoline-(3S)-carboxylic acid,
(55) 2-benzyl-7-{2-[2-(2,2-dimethylpropyl)-5-methyloxazol-4-yl]ethoxy}-1,2,3,4-tetrahydroisoquinoline-(3S)-carboxylic acid,
(56) ethyl 2-(2,2-dimethylpropyl)-7-[2-(5-methyl-2-phenyloxazol-4-yl)ethoxy]-1,2,3,4-tetrahydroisoquinoline-(3S)-carboxylate,
(57) 7-(benzofran-2-ylmethoxy)-2-benzyl-1,2,3,4-tetrahydroisoquinoline-(3S)-carboxylic acid,
(58) 2-isobutyryl-7-[2-(5-methyl-2-phenyloxazol-4-yl)ethoxy]-1,2,3,4-tetrahydroisoquinoline-(3S)-carboxylic acid,
(59) 7-[2-(benzofran-2-yl)ethoxy]-2-benzyl-1,2,3,4-tetrahydroisoquinoline-(3S)-carboxylic acid,
(60) 7-[2-(5-ethylpyridin-2-yl)ethoxy]-2-hexanoyl-1,2,3,4-tetrahydroisoquinoline-(3S)-carboxylic acid,
(61) 2-carboxymethyl-7-[2-(5-methyl-2-phenyloxazol-4-yl)ethoxy]-1,2,3,4-tetrahydroisoquinoline-(3S)-carboxylic acid,
(62) 2-[3-(methoxycarbonyl)propionyl]-7-[2-(5-methyl-2-phenyloxazol-4-yl)ethoxy]-1,2,3,4-tetrahydroisoquinoline-(3S)-carboxylic acid,
(63) 2-[3-(ethoxycarbonyl)propyl]-7-[2-(5-methyl-2-phenyloxazol-4-yl)ethoxy]-1,2,3,4-tetrahydroisoquinoline-(3S)-carboxylic acid,
(64) 2-benzyl-6-[2-(5-methyl-2-phenyloxazol-4-yl)ethoxy]-1,2,3,4-tetrahydroisoquinoline-(3RS)-carboxylic acid,
(65) 2-(3-acetylbenzyl)-7-[2-(5-methyl-2-phenyloxazol-4-yl)ethoxy]-1,2,3,4-tetrahydroisoquinoline-(3S)-carboxylic acid,
(66) 2-(2-acetylbenzyl)-7-[2-(5-methyl-2-phenyloxazol-4-yl)ethoxy]-1,2,3,4-tetrahydroisoquinoline-(3S)-carboxylic acid, and
(67) 2-benzyl-7-[(5-methyl-2-phenyloxazol-4-yl)methoxy]-1,2,3,4-tetrahydroisoquinoline-(3S)-carboxylic acid, and a pharmaceutically acceptable salt thereof;

[10] the heterocyclic compound of the above-mentioned [9] wherein the heterocyclic compound of the formula [I] is any of the above-mentioned compounds (1) to (47), and a pharmaceutically acceptable salt thereof;

[11] the heterocyclic compound of the above-mentioned [9] wherein the heterocyclic compound of the formula [I] is any of the above-mentioned compounds (1) to (21), and a pharmaceutically acceptable salt thereof;

[12] a pharmaceutical composition comprising the heterocyclic compound of any of the above-mentioned [1] to [11] or a pharmaceutically acceptable salt thereof;

[13] a pharmaceutical agent comprising the heterocyclic compound of any of the above-mentioned [1] to [11] or a pharmaceutically acceptable salt thereof, which is selected from the group consisting of a hypoglycemic agent, a hypolipidemic agent, an insulin resistance improver, a therapeutic agent of diabetes, a therapeutic agent of diabetic complication, a glucose tolerance improver, an anti-atherosclerosis agent, an anti-obesity agent, an antiinflammatory agent, an agent for the prophylaxis or treatment of PPAR-mediated disease and an agent for the prophylaxis or treatment of syndrome X;

[14] a hypoglycemic agent comprising the heterocyclic compound of any of the above-mentioned [1] to [11] or a pharmaceutically acceptable salt thereof;

[15] a hypolipidemic agent comprising the heterocyclic compound of any of the above-mentioned [1] to [11] or a pharmaceutically acceptable salt thereof;

[16] an insulin resistance improver comprising the heterocyclic compound of any of the above-mentioned [1] to [11] or a pharmaceutically acceptable salt thereof;

[17] a therapeutic agent of diabetic complications, comprising the heterocyclic compound of any of the above-mentioned [1] to [11] or a pharmaceutically acceptable salt thereof; and

[18] a therapeutic agent of diabetes, comprising the heterocyclic compound of any of the above-mentioned [1] to [11] or a pharmaceutically acceptable salt thereof.

The novel heterocyclic compound of the formula [I]

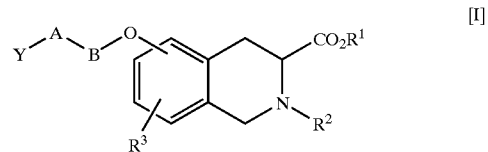

wherein $R^1$ is hydrogen atom or lower alkyl, $R^2$ is hydrogen atom, alkyl optionally having a substituent, cycloalkyl, cycloalkylalkyl, aryl optionally having a substituent, arylalkyl optionally having a substituent, alkenyl optionally having a substituent, alkynyl optionally having a substituent, heterocyclic alkyl optionally having a substituent or —COR$^4$ wherein $R^4$ is hydrogen atom, alkyl optionally having a substituent, aryl optionally having a substituent, alkenyl optionally having a substituent, arylalkyl optionally having a substituent or heterocyclic residue optionally having a substituent, $R^3$ is hydrogen atom, lower alkyl or lower alkoxy, A is a single bond or >N—$R^5$ wherein $R^5$ is hydrogen atom or lower alkyl, B is lower alkylene, and Y is aryl optionally having a substituent or an aromatic heterocyclic residue optionally having a substituent and a pharmaceutically acceptable salt thereof have a hypoglycemic action, a blood hypolipidemic action, an insulin resistance-improving action and a PPAR-activating action.

The alkoxycarbonyl in the present invention preferably has 2 to 5 carbon atoms. Examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like.

The lower alkyl at $R^1$, $R^3$ and $R^5$ is preferably straight chain or branched chain alkyl having 1 to 6 carbon atoms, which is exemplified by methyl, ethyl, propyl, isopropyl, butyl, isobutyl, sec-butyl, tert-butyl, pentyl, isopentyl, neopentyl, hexyl and the like, preferably methyl, ethyl, propyl and isopropyl.

The lower alkoxy at $R^3$ is preferably straight chain or branched chain alkoxy having 1 to 6 carbon atoms, which is exemplified by methoxy, ethoxy, propoxy, isopropoxy, butoxy, isobutoxy, sec-butoxy, tert-butoxy, pentyloxy, isopentyloxy, neopentyloxy, hexyloxy and the like, preferably methoxy, ethoxy, propoxy and isopropoxy.

The "alkenyl", in the alkenyl optionally having a substituent at $R^2$ and $R^4$ is preferably straight chain or branched chain alkenyl having 2 to 6 carbon atoms, which is exemplified by vinyl, 1-propenyl, 2-propenyl, isopropenyl, allyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 1-hexenyl, 2-hexenyl, 3-hexenyl, 4-hexenyl, 5-hexenyl and the like, preferably allyl, 2-butenyl, 3-butenyl, 4-pentenyl, 2-propenyl and 2-methyl-1-propenyl. As the substituent, exemplified are lower alkoxy (as defined for lower alkoxy at $R^3$), hydroxy, carboxy, alkoxycarbonyl, halogen atom (chlorine atom, bromine atom, iodine atom and fluorine atom), nitro, amino and the like. When alkenyl at $R^2$ or $R^4$ is substituted, the number of the substituent is preferably 1 or 2.

The "alkynyl" in the alkynyl optionally having a substituent at $R^2$ is preferably straight chain or branched chain alkynyl having 2 to 4 carbon atoms, which is exemplified by ethynyl, 1-propynyl, 2-propynyl, 1-methyl-2-propynyl and the like, preferably ethynyl and 2-propynyl. As the substituent, exemplified are lower alkoxy (as defined for lower alkoxy at $R^3$), hydroxy, carboxy, alkoxycarbonyl, halogen atom (chlorine atom, bromine atom, iodine atom and fluorine atom), nitro, amino and the like. When alkynyl at $R^2$ is substituted, the number of the substituent is preferably 1 or 2.

The "alkyl" in the alkyl optionally having a substituent at $R^2$ and $R^4$ is preferably straight chain or branched chain alkyl having 1 to 8 carbon atoms, which is exemplified by methyl, ethyl, propyl, isopropyl, butyl, isobutyl, sec-butyl, tert-butyl, pentyl, isopentyl, neopentyl, hexyl, heptyl, octyl and the like, preferably methyl, ethyl, isobutyl, propyl, hexyl, pentyl and isopropyl. As the substituent, exemplified are lower alkoxy (as defined for lower alkoxy at $R^3$), hydroxy, carboxy, alkoxycarbonyl, halogen atom (chlorine atom, bromine atom, iodine atom and fluorine atom), nitro, amino and the like. When alkyl at $R^2$ is substituted, the number of the substituent is preferably 1 or 2.

The cycloalkyl at $R^2$ is preferably cycloalkyl having 3 to 8 carbon atoms, which is exemplified by cyclopropyl, cyclobutyl, cyclopentyl, cyclohexyl, cycloheptyl, cyclooctyl and the like, preferably cyclopropyl, cyclopentyl and cyclohexyl.

The cycloalkylalkyl at $R^2$ is that wherein cycloalkyl moiety is preferably cycloalkyl having 3 to 8 carbon atoms and alkyl moiety is preferably straight chain or branched chain alkyl having 1 to 3 carbon atoms. Examples thereof are cyclopropylmethyl, cyclobutylmethyl, cyclopentylmethyl, cyclohexylmethyl, cycloheptylmethyl, cyclooctylmethyl, 2-cyclopropylethyl, 2-cyclobutylethyl, 2-cyclopentylethyl, 2-cyclohexylethyl, 2-cycloheptylethyl, 2-cyclooctylethyl, 3-cyclopropylpropyl, 3-cyclobutylpropyl, 3-cyclopentylpropyl, 3-cyclohexylpropyl, 3-cycloheptylpropyl, 3-cyclooctylpropyl, 1-cyclohexylethyl, 1-cyclohexylpropyl, 2-cyclohexylpropyl and the like, preferably cyclohexylmethyl, 2-cyclohexylethyl, cyclopentylmethyl and 2-cyclopentylethyl.

The aryl in the aryl optionally having a substituent at $R^2$, $R^4$ and Y is exemplified by phenyl, naphthyl and the like. As the substituent, exemplified are lower alkyl (as defined for lower alkyl at $R^1$, $R^3$ and $R^5$), lower alkoxy (as defined for lower alkoxy at $R^3$), hydroxy, carboxy, alkoxycarbonyl, halogen atom (chlorine atom, bromine atom, iodine atom and fluorine atom), nitro, amino, acyl (e.g., formyl, acetyl, propanoyl etc.) and the like. When aryl at Y is substituted, the number of the substituent is preferably 1 or 2.

The arylalkyl optionally having a substituent at $R^2$ and $R^4$ is exemplified by that wherein aryl moiety is preferably phenyl, naphthyl and the like, and alkyl moiety is preferably straight chain or branched chain alkyl having 1 to 3 carbon atoms. Examples of arylalkyl are benzyl, 1-naphthylmethyl, 2-naphthylmethyl, 2-phenylethyl, 2-(1-naphthyl)ethyl, 2-(2-naphthyl)ethyl, 3-phenylpropyl, 3-(1-naphthyl)propyl, 3-(2-naphthyl)propyl, 1-phenylethyl, 2-phenylpropyl, 1-(1-naphthyl)ethyl, 1-(2-naphthyl)ethyl, 1-(1-naphthyl)propyl, 1-(2-naphthyl)propyl, 2-(1-naphthyl)propyl, 2-(2-naphthyl)propyl and the like, preferably benzyl, 3-phenylpropyl, 1-naphthylmethyl and 2-naphthylmethyl. As the substituent, exemplified are lower alkyl (as defined for lower alkyl at $R^1$, $R^3$ and $R^5$), lower alkoxy (as defined for lower alkoxy at $R^3$), hydroxy, carboxy, alkoxycarbonyl, halogen atom (chlorine atom, bromine atom, iodine atom and fluorine atom), nitro, amino, acyl (e.g., formyl, acetyl, propanoyl etc.) and the like, preferably lower alkyl, lower alkoxy, halogen atom and acyl. When arylalkyl at Y is substituted, the number of the substituent is preferably 1 or 2.

The aromatic heterocycle in the aromatic heterocyclic residue optionally having a substituent at Y is preferably a monocyclic heterocycle or a condensed heterocycle containing at least one hetero atom selected from the group consisting of oxygen atom, nitrogen atom and sulfur atom. The condensed heterocycle in the present invention has two rings and encompasses that having hetero atom(s) on the both rings. Preferable monocyclic heterocycle includes a 5- or 6-membered ring. The heterocycle constituting the condensed heterocycle is preferably a 5- or 6-membered ring. The ring without a hetero atom, which constitutes the condensed heterocycle, is preferably a 5- or 6-membered ring. Examples of the aromatic heterocyclic residue are monocyclic heterocyclic residue such as furyl, thienyl, pyridyl, imidazolyl, pyrazolyl, oxazolyl, isooxazolyl, thiazolyl, triazolyl, thiadiazolyl, oxadiazolyl, pyridazinyl, pyrimidinyl or pyrazinyl and the like; a condensed heterocyclic residue such as indolyl, isoindolyl, indolinyl, isoindolinyl, indazolyl, benzofuranyl, benzothiophenyl, benzimidazolyl, benzoxazolyl, benzothiazolyl, quinolyl, isoquinolyl, benzoxazinyl, benzothiazinyl, furo[2,3-b]pyridyl, thieno[2,3-b]pyridyl, naphthyridinyl, imidazopyridyl, oxazolopyridyl, thiazolopyridyl and the like, with preference given to pyridyl, oxazolyl, indolinyl, benzoxazolyl, thiazolyl, benzothiazolyl, indolyl, quinolyl and benzofuranyl. As the substituent, exemplified are lower alkyl (as defined for lower alkyl at $R^1$, $R^3$ and $R^5$), lower alkoxy (as defined for lower alkoxy at $R^3$), hydroxy, carboxy, alkoxycarbonyl, halogen atom (chlorine atom, bromine atom, iodine atom and fluorine atom), nitro, amino aryl (e.g., phenyl, naphthyl and the like), heterocyclic residue (e.g., thienyl, pyridyl, furyl and the like), alkenyl (as defined for alkenyl at $R^2$ and $R^4$), cycloalkyl (e.g., cyclopropyl etc.) and the like, preferably aryl, lower alkyl, carboxy, heterocyclic residue, alkenyl and cycloalkyl. When aromatic heterocyclic residue at Y is substituted, the number of the substituent is preferably 1 or 2.

The lower alkylene at B is preferably straight chain or branched chain alkylene having 1 to 6 carbon atoms, which is exemplified by methylene, ethylene, trimethylene, tetramethylene, pentamethylene, hexamethylene, methylmethylene, 2,2-dimethyltrimethylene, 2-ethyltrimethylene, 1-methyltetramethylene, 2-methyltetramethylene, 3-methyltetramethylene, 3,3-dimethyltrimethylene, 3,3-dimethyltetramethylene and the like, preferably ethylene, trimethylene and tetramethylene.

The heterocyclic moiety in the heterocyclic alkyl optionally having a substituent at $R^2$ is as defined for the "aromatic heterocyclic residue" in the "aromatic heterocyclic residue optionally having a substituent" at Y. As the alkyl moiety, exemplified is straight chain or branched chain alkyl having 1 to 3 carbon atoms. The specific examples of the heterocyclic alkyl are 1-pyridylmethyl, 2-pyridylmethyl, 3-pyridylmethyl, 4-pyridylmethyl; 1-(1-pyridyl)ethyl, 1-(2-pyridyl)ethyl, 1-(3-pyridyl)ethyl, 1-(4-pyridyl)ethyl, 2-(1-pyridyl)ethyl, 2-(2-pyridyl)ethyl, 2-(3-pyridyl)ethyl, 2-(4-pyridyl)ethyl; 1-(1-pyridyl)propyl, 1-(2-pyridyl)propyl, 1-(3-pyridyl)propyl, 1-(4-pyridyl)propyl, 2-(1-pyridyl)propyl, 2-(2-pyridyl)propyl, 2-(3-pyridyl)propyl, 2-(4-pyridyl)propyl, 3-(1-pyridyl)propyl, 3-(2-pyridyl)propyl, 3-(3-pyridyl)propyl, 3-(4-pyridyl)propyl; 2-thienylmethyl, 3-thienylmethyl; 1-(2-thienyl)ethyl, 1-(3-thienyl)ethyl, 2-(2-thienyl)ethyl, 2-(3-thienyl)ethyl; 1-(2-thienyl)propyl, 1-(3-thienyl)propyl, 2-(2-thienyl)propyl, 2-(3-thienyl)propyl, 3-(2-thienyl)propyl, 3-(3-thienyl)propyl; and the like. The heterocyclic alkyl may be substituted at the heterocyclic moiety. As the substituent, exemplified are lower alkyl (as defined for lower alkyl at $R^1$, $R^3$ and $R^5$), lower alkoxy (as defined for lower alkoxy at $R^3$), hydroxy, carboxy, alkoxycarbonyl, halogen atom (chlorine atom, bromine atom, iodine atom and fluorine atom), nitro, amino and the like. When the heterocyclic moiety is substituted, the number of the substituent is preferably 1 or 2.

With regard to the heterocyclic residue optionally having a substituent at $R^4$, the heterocyclic moiety is the same as the "aromatic heterocyclic residue" in the "aromatic heterocyclic residue optionally having a substituent" at Y, which is preferably pyridyl. The heterocyclic residue may be substituted. As the substituent, exemplified are lower alkyl (as defined for lower alkyl at $R^1$, $R^3$ and $R^5$), lower alkoxy (as defined for lower alkoxy at $R^3$), hydroxy, carboxy, alkoxycarbonyl, halogen atom (chlorine atom, bromine atom, iodine atom and fluorine atom), nitro, amino and the like. When the heterocyclic moiety is substituted, the number of the substituent is preferably 1 or 2.

The heterocyclic compound [I] and a pharmaceutically acceptable salt thereof are preferably exemplified by the following.

A heterocyclic compound of the above-mentioned formula [I], wherein (1) $R^1$ is hydrogen atom or lower alkyl, $R^2$ is hydrogen atom, alkyl optionally having a substituent, cycloalkyl, cycloalkylalkyl, aryl optionally having a substituent, arylalkyl optionally having a substituent or —$COR^4$ wherein $R^4$ is hydrogen atom, alkyl optionally having a substituent, aryl optionally having a substituent or arylalkyl optionally having a substituent, $R^3$ is hydrogen atom, lower alkyl or lower alkoxy, A is a single bond or >N—$R^5$ wherein $R^5$ is hydrogen atom or lower alkyl, B is lower alkylene, and Y is aryl optionally having a substituent or an aromatic heterocyclic residue optionally having a substituent, (2) $R^1$ is hydrogen atom or lower alkyl, $R^2$ is hydrogen atom, alkyl, cycloalkylalkyl, arylalkyl optionally having a substituent, alkenyl, alkynyl, heterocyclic alkyl or —$COR^4$ wherein $R^4$ is alkyl, alkenyl or aryl, $R^3$ is hydrogen atom or lower alkoxy, A is a single bond or >N—$R^5$ wherein $R^5$ is lower alkyl, B is lower alkylene, and Y is aryl or an aromatic heterocyclic residue optionally having a substituent, or (3) $R^1$ is hydrogen atom or lower alkyl, $R^2$ is hydrogen atom, alkyl, cycloalkylalkyl, arylalkyl optionally having a substituent or —$COR^4$ wherein $R^4$ is alkyl or aryl, $R^3$ is hydrogen atom, A is a single bond or >N—$R^5$ wherein $R^5$ is lower alkyl, B is lower alkylene, and Y is an aromatic heterocyclic residue optionally having a substituent and a pharmaceutically acceptable salt thereof.

In the formula [I], Y—A— is preferably

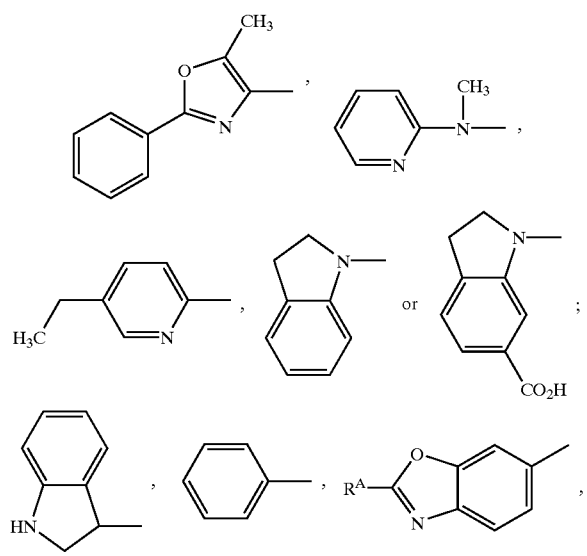

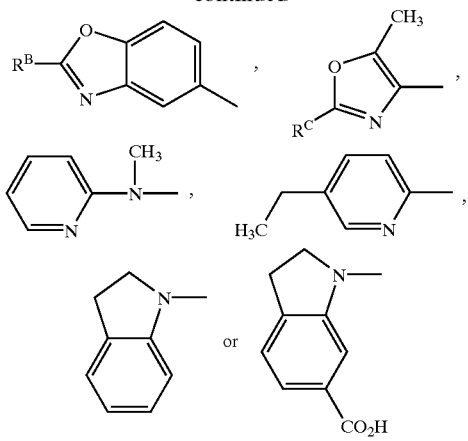

wherein

R^A is isopropyl or tert-butyl,

R^B is isopropyl or tert-butyl, and

R^C is isopropyl, tert-butyl, phenyl, thiophen-2-yl, 2-methylpropenyl or 3-butenyl; or

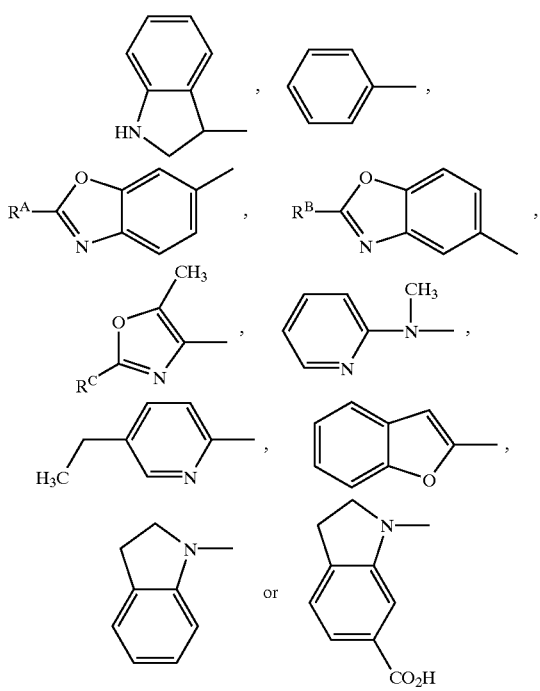

wherein

R^A is isopropyl or tert-butyl,

R^B is isopropyl or tert-butyl,

R^C is isopropyl, tert-butyl, phenyl, thiophen-2-yl, 2-methylpropenyl, 3-butenyl, cyclopropyl, 1-butenyl or 2,2-dimethylpropyl, with particular preference given to

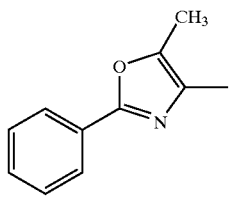

Preferable examples of the heterocyclic compound [I] and the pharmaceutically acceptable salt thereof are (1) 7-[2-(5-methyl-2-phenyloxazol-4-yl)ethoxy]-1,2,3,4-tetrahydroisoquinoline-(3S)-carboxylic acid, (2) 2-benzyl-7-[2-(5-methyl-2-phenyloxazol-4-yl)ethoxy]-1,2,3,4-tetrahydroisoquinoline-(3S)-carboxylic acid, (3) 2-acetyl-7-[2-(5-methyl-2-phenyloxazol-4-yl)ethoxy]-1,2,3,4-tetrahydroisoquinoline-(3S)-carboxylic acid, (4) 2-methyl-7-[2-(5-methyl-2-phenyloxazol-4-yl)ethoxy]-1,2,3,4-tetrahydroisoquinoline-(3S)-carboxylic acid, (5) 2-hexanoyl-7-[2-(5-methyl-2-phenyloxazol-4-yl)ethoxy]-1,2,3,4-tetrahydroisoquinoline-(3S)-carboxylic acid, (6) 2-hexyl-7-[2-(5-methyl-2-phenyloxazol-4-yl)ethoxy]-1,2,3,4-tetrahydroisoquinoline-(3S)-carboxylic acid, (7) 2-isobutyl-7-[2-(5-methyl-2-phenyloxazol-4-yl)ethoxy]-1,2,3,4-tetrahydroisoquinoline-(3S)-carboxylic acid, (8) 2-cyclohexylmethyl-7-[2-(5-methyl-2-phenyloxazol-4-yl)ethoxy]-1,2,3,4-tetrahydroisoquinoline-(3S)-carboxylic acid, (9) 7-[2-(5-methyl-2-phenyloxazol-4-yl)ethoxy]-2-(3-phenylpropyl)-1,2,3,4-tetrahydroisoquinoline-(3S)-carboxylic acid,

(10) 2-benzoyl-7-[2-(5-methyl-2-phenyloxazol-4-yl)ethoxy]-1,2,3,4-tetrahydroisoquinoline-(3S)-carboxylic acid,

(11) 2-benzyl-7-[2-(N-methyl-N-(pyridin-2-yl)amino)ethoxy]-1,2,3,4-tetrahydroisoquinoline-(3S)-carboxylic acid,

(12) 2-benzyl-7-[2-(5-ethyl-pyridin-2-yl)ethoxy]-1,2,3,4-tetrahydroisoquinoline-(3S)-carboxylic acid,

(13) 2-benzyl-7-[2-(indolin-1-yl)ethoxy]-1,2,3,4-tetrahydroisoquinoline-(3S)-carboxylic acid,

(14) ethyl 2-benzyl-7-[2-(5-methyl-2-phenyloxazol-4-yl)ethoxy]-1,2,3,4-tetrahydroisoquinoline-(3S)-carboxylate,

(15) methyl 7-[2-(5-methyl-2-phenyloxazol-4-yl)ethoxy]-1,2,3,4-tetrahydroisoquinoline-(3S)-carboxylate,

(16) 2-(4-methoxybenzyl)-7-[2-(5-methyl-2-phenyloxazol-4-yl)ethoxy]-1,2,3,4-tetrahydroisoquinoline-(3S)-carboxylic acid,

(17) ethyl 2-(4-methoxybenzyl)-7-[2-(5-methyl-2-phenyloxazol-4-yl)ethoxy]-1,2,3,4-tetrahydroisoquinoline-(3S)-carboxylate,

(18) 2-(4-methylbenzyl)-7-[2-(5-methyl-2-phenyloxazol-4-yl)ethoxy]-1,2,3,4-tetrahydroisoquinoline-(3S)-carboxylic acid,

(19) ethyl 2-(4-methylbenzyl)-7-[2-(5-methyl-2-phenyloxazol-4-yl)ethoxy]-1,2,3,4-tetrahydroisoquinoline-(3S)-carboxylate,

(20) 2-benzyl-7-[2-(6-carboxyindolin-1-yl)ethoxy]-1,2,3,4-tetrahydroisoquinoline-(3S)-carboxylic acid, and

(21) 2-(4-fluorobenzyl)-7-[2-(5-methyl-2-phenyloxazol-4-yl)ethoxy]-1,2,3,4-tetrahydroisoquinoline-(3S)-carboxylic acid, and pharmaceutically acceptable salt thereof. Besides the above-mentioned, preferred are

(22) 2-(2,2-dimethylpropionyl)-7-[2-(5-methyl-2-phenyloxazol-4-yl)ethoxy]-1,2,3,4-tetrahydroisoquinoline-(3S)-carboxylic acid,

(23) 2-(2,2-dimethylpropyl)-7-[2-(5-methyl-2-phenyloxazol-4-yl)ethoxy]-1,2,3,4-tetrahydroisoquinoline-(3S)-carboxylic acid,
(24) 2-benzyl-7-[2-(5-methyl-2-tert-butyloxazol-4-yl)ethoxy]-1,2,3,4-tetrahydroisoquinoline-(3S)-carboxylic acid,
(25) 2-benzyl-7-[2-(5-methyl-2-(thiophen-2-yl)oxazol-4-yl)ethoxy]-1,2,3,4-tetrahydroisoquinoline-(3S)-carboxylic acid,
(26) 2-benzyl-7-[2-(5-methyl-2-isopropyloxazol-4-yl)ethoxy]-1,2,3,4-tetrahydroisoquinoline-(3S)-carboxylic acid,
(27) 2-butyl-7-[2-(5-methyl-2-phenyloxazol-4-yl)ethoxy]-1,2,3,4-tetrahydroisoquinoline-(3S)-carboxylic acid,
(28) 2-benzyl-7-{2-[5-methyl-2-(2-methylpropenyl)oxazol-4-yl]ethoxy}-1,2,3,4-tetrahydroisoquinoline-(3S)-carboxylic acid,
(29) 2-benzyl-7-{2-[2-(3-butenyl)-5-methyloxazol-4-yl]ethoxy}-1,2,3,4-tetrahydroisoquinoline-(3S)-carboxylic acid,
(30) 2-allyl-7-[2-(5-methyl-2-phenyloxazol-4-yl)ethoxy]-1,2,3,4-tetrahydroisoquinoline-(3S)-carboxylic acid,
(31) 7-[2-(5-methyl-2-phenyloxazol-4-yl)ethoxy]-2-(2-propynyl)-1,2,3,4-tetrahydroisoquinoline-(3S)-carboxylic acid,
(32) 2-(2-butenyl)-7-[2-(5-methyl-2-phenyloxazol-4-yl)ethoxy]-1,2,3,4-tetrahydroisoquinoline-(3S)-carboxylic acid,
(33) 2-benzyl-7-[(indolin-3-yl)ethoxy]-1,2,3,4-tetrahydroisoquinoline-(3S)-carboxylic acid,
(34) 2-(3-butenyl)-7-[2-(5-methyl-2-phenyloxazol-4-yl)ethoxy]-1,2,3,4-tetrahydroisoquinoline-(3S)-carboxylic acid,
(35) 7-[2-(5-methyl-2-phenyloxazol-4-yl)ethoxy]-2-pentanoyl-1,2,3,4-tetrahydroisoquinoline-(3S)-carboxylic acid,
(36) 7-[2-(5-methyl-2-phenyloxazol-4-yl)ethoxy]-2-(4-pentenoyl)-1,2,3,4-tetrahydroisoquinoline-(3S)-carboxylic acid,
(37) 2-(3-methyl-2-butenoyl)-7-[2-(5-methyl-2-phenyloxazol-4-yl)ethoxy]-1,2,3,4-tetrahydroisoquinoline-(3S)-carboxylic acid,
(38) 2-(3,3-dimethylbutyryl)-7-[2-(5-methyl-2-phenyloxazol-4-yl)ethoxy]-1,2,3,4-tetrahydroisoquinoline-(3S)-carboxylic acid,
(39) 2-benzyl-7-methoxy-6-[2-(5-methyl-2-phenyloxazol-4-yl)-ethoxy]-1,2,3,4-tetrahydroisoquinoline-(3RS)-carboxylic acid,
(40) 7-[2-(5-methyl-2-phenyloxazol-4-yl)ethoxy]-2-(pyridin-2-ylmethyl)-1,2,3,4-tetrahydroisoquinoline-(3S)-carboxylic acid,
(41) 2-benzyl-7-(3-methyl-3-phenylbutoxy)-1,2,3,4-tetrahydroisoquinoline-(3S)-carboxylic acid,
(42) 2-benzyl-7-(3,3-dimethyl-4-phenylbutoxy)-1,2,3,4-tetrahydroisoquinoline-(3S)-carboxylic acid,
(43) 2-benzyl-7-(2-isopropylbenzoxazol-6-yl)methoxy-1,2,3,4-tetrahydroisoquinoline-(3S)-carboxylic acid,
(44) 2-benzyl-7-(2-tert-butylbenzoxazol-6-yl)methoxy-1,2,3,4-tetrahydroisoquinoline-(3S)-carboxylic acid,
(45) 2-benzyl-7-(2-tert-butylbenzoxazol-5-yl)methoxy-1,2,3,4-tetrahydroisoquinoline-(3S)-carboxylic acid,
(46) 7-(2-tert-butylbenzoxazol-6-yl)methoxy-2-(2,2-dimethylpropyl)-1,2,3,4-tetrahydroisoquinoline-(3S)-carboxylic acid, and
(47) 2-benzyl-7-(2-isopropylbenzoxazol-5-yl)methoxy-1,2,3,4-tetrahydroisoquinoline-(3S)-carboxylic acid, and pharmaceutically acceptable salts thereof.

In addition to the above-mentioned, the following heterocyclic compound [I] and pharmaceutically acceptable salts thereof are preferable.
(48) 7-[2-(5-methyl-2-phenyloxazol-4-yl)ethoxy]-2-(pyridin-4-ylmethyl)-1,2,3,4-tetrahydroisoquinoline-(3S)-carboxylic acid,
(49) 7-[2-(5-methyl-2-phenyloxazol-4-yl)ethoxy]-2-[(pyridin-2-yl)carbonyl]-1,2,3,4-tetrahydroisoquinoline-(3S)-carboxylic acid,
(50) methyl 2-benzyl-7-[2-(5-methyl-2-phenyloxazol-4-yl)-ethoxy]-1,2,3,4-tetrahydroisoquinoline-(3S)-carboxylate,
(51) 2-benzyl-7-[2-(2-cyclopropyl-5-methyloxazol-4-yl)-ethoxy]-1,2,3,4-tetrahydroisoquinoline-(3S)-carboxylic acid,
(52) 2-(3-methyl-2-butenyl)-7-[2-(5-methyl-2-phenyloxazol-4-yl)ethoxy]-1,2,3,4-tetrahydroisoquinoline-(3S)-carboxylic acid,
(53) 2-(2,2-dimethylpropyl)-7-[2-(5-methyl-2-tert-butyloxazol-4-yl)ethoxy]-1,2,3,4-tetrahydroisoquinoline-(3S)-carboxylic acid,
(54) 2-benzyl-7-{2-[2-(1-butenyl)-5-methyloxazol-4-yl]ethoxy}-1,2,3,4-tetrahydroisoquinoline-(3S)-carboxylic acid,
(55) 2-benzyl-7-{2-[2-(2,2-dimethylpropyl)-5-methyloxazol-4-yl]ethoxy}-1,2,3,4-tetrahydroisoquinoline-(3S)-carboxylic acid,
(56) ethyl 2-(2,2-dimethylpropyl)-7-[2-(5-methyl-2-phenyloxazol-4-yl)ethoxy]-1,2,3,4-tetrahydroisoquinoline-(3S)-carboxylate,
(57) 7-(benzofran-2-ylmethoxy)-2-benzyl-1,2,3,4-tetrahydroisoquinoline-(3S)-carboxylic acid,
(58) 2-isobutyryl-7-[2-(5-methyl-2-phenyloxazol-4-yl)ethoxy]-1,2,3,4-tetrahydroisoquinoline-(3S)-carboxylic acid,
(59) 7-[2-(benzofran-2-yl)ethoxy]-2-benzyl-1,2,3,4-tetrahydroisoquinoline-(3S)-carboxylic acid,
(60) 7-[2-(5-ethylpyridin-2-yl)ethoxy]-2-hexanoyl-1,2,3,4-tetrahydroisoquinoline-(3S)-carboxylic acid,
(61) 2-carboxymethyl-7-[2-(5-methyl-2-phenyloxazol-4-yl)ethoxy]-1,2,3,4-tetrahydroisoquinoline-(3S)-carboxylic acid,
(62) 2-[3-(methoxycarbonyl)propionyl]-7-[2-(5-methyl-2-phenyloxazol-4-yl)ethoxy]-1,2,3,4-tetrahydroisoquinoline-(3S)-carboxylic acid,
(63) 2-[3-(ethoxycarbonyl)propyl]-7-[2-(5-methyl-2-phenyloxazol-4-yl)ethoxy]-1,2,3,4-tetrahydroisoquinoline-(3S)-carboxylic acid,
(64) 2-benzyl-6-[2-(5-methyl-2-phenyloxazol-4-yl)ethoxy]-1,2,3,4-tetrahydroisoquinoline-(3RS)-carboxylic acid,
(65) 2-(3-acetylbenzyl)-7-[2-(5-methyl-2-phenyloxazol-4-yl)ethoxy]-1,2,3,4-tetrahydroisoquinoline-(3S)-carboxylic acid,
(66) 2-(2-acetylbenzyl)-7-[2-(5-methyl-2-phenyloxazol-4-yl)ethoxy]-1,2,3,4-tetrahydroisoquinoline-(3S)-carboxylic acid,
(67) 2-benzyl-7-[(5-methyl-2-phenyloxazol-4-yl)methoxy]-1,2,3,4-tetrahydroisoquinoline-(3S)-carboxylic acid.

Since the heterocyclic compound [I] has an asymmetric carbon at the 3-position of the 1,2,3,4-tetrahydroisoquinoline ring, it includes various stereoisomers. The most preferable configuration is

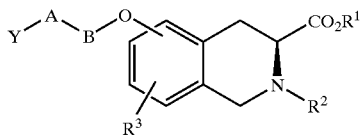

wherein $R^1$, $R^2$, $R^3$, Y, A and B are as defined above.

The heterocyclic compound [I] can be converted to a pharmaceutically acceptable salt as necessary.

When the heterocyclic compound [I] has a basic group, an acid addition salt can be formed. The acid used for forming the acid addition salt is not subject to any particular limitation as long as it can form a salt with a basic moiety and it is a pharmaceutically acceptable acid. Examples of the acid include inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, p-toluenesulfonic acid and the like, and the like.

When the heterocyclic compound [I] has an acidic group (e.g., carboxyl group and the like), a salt such as an alkali metal salt (e.g., sodium salt, potassium salt and the like), an alkaline earth metal salt (e.g., calcium salt, magnesium salt and the like) or an organic base salt (e.g., triethylamine salt, dicyclohexylamine salt, pyridine salt and the like) and the like may be formed.

The heterocyclic compound [I] and the pharmaceutically acceptable salt thereof can be produced according to any of the following Production Methods.

Production Method 1

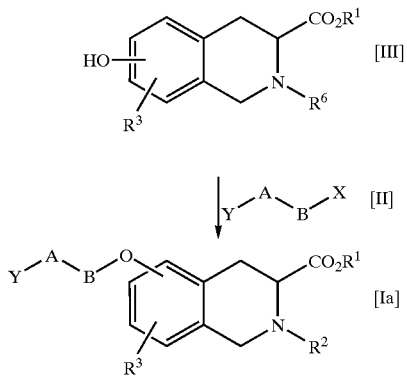

wherein $R^1$, $R^3$, A, B and Y are as defined above, $R^6$ is hydrogen atom, alkyl optionally having a substituent, cycloalkyl, cycloalkylalkyl, aryl optionally having a substituent, arylalkyl optionally having a substituent, alkenyl optionally having a substituent, alkynyl optionally having a substituent, heterocyclic alkyl optionally having a substituent, —COR$^4$ ($R^4$ is as defined above) or amino-protecting group, and X is hydroxy, halogen atom (fluorine atom, chlorine atom, bromine atom or iodine atom), or a leaving group such as alkanesulfonyloxy (e.g., methanesulfonyloxy, ethanesulfonyloxy, propanesulfonyloxy, trifluoromethanesulfonyloxy and the like), arylsulfonyloxy (e.g., phenylsulfonyloxy, tolylsulfonyloxy and the like) and the like.

In Production Method 1, the compound of formula [Ia] (also referred to as compound [Ia]) is synthesized by the reaction of the compound of the formula [II] (also referred to as compound [II]) with the compound of the formula [III] (also referred to as compound [III]).

The "alkyl optionally having a substituent", "cycloalkyl", "cycloalkylalkyl", "aryl optionally having a substituent", "arylalkyl optionally having a substituent", "alkenyl optionally having a substituent", "alkynyl optionally having a substituent" and "heterocyclic alkyl optionally having a substituent" at $R^6$ are as defined for $R^2$.

Examples of the amino-protecting group at $R^6$ are formyl, monochloroacetyl, dichloroacetyl, trichloroacetyl, trifluoroacetyl, methoxycarbonyl, ethoxycarbonyl, benzyloxycarbonyl, p-nitrobenzyloxycarbonyl, diphenylmethyloxycarbonyl, methoxymethylcarbonyl, methoxymethyloxycarbonyl, trimethylsilyl, 2,2,2-trichloroethoxycarbonyl, 2-methylsulfonylethyloxycarbonyl, tert-butoxycarbonyl (hereinafter to be referred to as Boc), trityl and the like.

Production Method 1-a: When X is hydroxy, Production Method 1 comprises a dehydrating reaction such as Mitsunobu Reaction (Reagents for Organic Synthesis, Fisher & Fisher, Vol. 6, 645) and the like. The reaction is generally carried out in a solvent with an azo compound and phosphine. As the azo compound, exemplified are di($C_1$–$C_4$ alkyl) azodicarboxylate (e.g., diethyl azodicarboxylate and the like), azodicarboxamide (e.g., 1,1'-(azodicarbonyl)dipiperidine and the like) and the like. As the phosphine, exemplifdied are triarylphosphine (e.g., triphenylphosphine and the like), tri($C_1$–$C_4$alkyl)phosphine (e.g., tributylphosphine and the like), and the like.

As the solvent used in the Production Method 1-a, exemplified are dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like; and a mixture thereof and the like, but the solvent is not limited as far as it does not adversely influence the reaction.

The amount of the compound [II] used in the Production Method 1-a is not subject to any particular limitation. It is used in an amount of generally 1–5 mol, preferably 1–3 mol, per 1 mol of compound [III]. The azo compound and phosphine are respectively used in an amount of generally 1–3 mol, preferably 1–1.5 mol, per 1 mol of compound [III].

While the reaction conditions such as reaction temperature and reaction time and the like in Production Method 1-a vary depending on the reagent, solvent and the like to be used in this reaction, the reaction generally proceeds at a temperature of from –30° C. to 50° C. for 30 min to about a dozen hours.

Production Method 1-b: When X is halogen atom or leaving group such as alkanesulfonyloxy (e.g., methanesulfonyloxy, ethanesulfonyloxy, propanesulfonyloxy, trifluoromethanesulfonyloxy and the like), arylsulfonyloxy (e.g., phenylsulfonyloxy, tolylsulfonyloxy and the like) and the like, Production Method 1-b is performed in a solvent similar to that used in the Production Method 1-a and in the presence of a base.

The base used in the Production Method 1-b is exemplified by, but not particulary limited to, inorganic base such as alkali metal carbonate (e.g., sodium carbonate, potassium carbonate, sodium hydrogencarbonate, potassium hydrogencarbonate and the like), alkali metal hydroxide (e.g., sodium hydroxide, potassium hydroxide and the like), metal hydride compound (e.g., sodium hydride, potassium hydride, calcium hydride and the like) and the like; organic base such as alkali metal alkoxide (e.g., sodium methoxide, sodium ethoxide, potassium tert-butoxide and the like), amines (e.g., triethylamine, diisopropylethylamine and the like) and the like.

The amount of the compound [II] used in the Production Method 1-b is not subject to any particular limitation. It is used in an amount of generally 1–5 mol, preferably 1–3 mol, per 1 mol of compound [III]. The base is used in an amount of generally 1–5 mol, preferably 1–3 mol, per 1 mol of compound [III].

While the reaction conditions such as reaction temperature and reaction time and the like in Production Method 1-b vary depending on the reagent, solvent and the like to be used in this reaction, the reaction generally proceeds at a temperature of from −30° C. to 150° C. for 30 min to about a dozen hours.

In the Production Method 1, $R^1$ of compound [III] is preferably lower alkyl. In this case, compound [Ia] wherein $R^1$ is lower alkyl is obtained, and this compound may be led to the compound [Ia] wherein $R^1$ is hydrogen atom, by hydrolysis according to a method known per se.

In the Production Method 1, when $R^6$ of compound [III] is amino-protecting group, compound [Ia] wherein $R^6$ is amino-protecting group is obtained. This compound may be led to the compound [Ia] wherein $R^6$ is hydrogen atom, by deprotection according to a method known per se.

Production Method 2

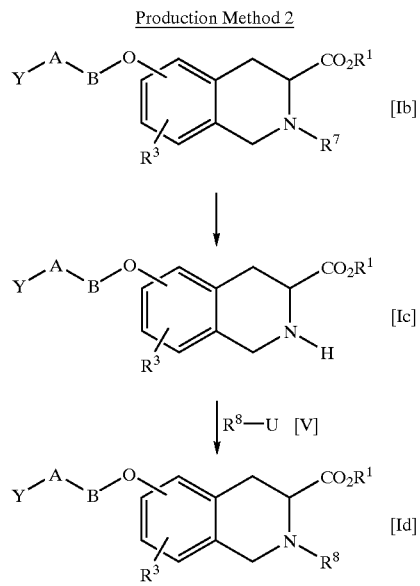

wherein $R^1$, $R^3$, A, B and Y are as defined above, $R^7$ is amino-protecting group, $R^8$ is alkyl optionally having a substituent, cycloalkyl, cycloalkylalkyl, aryl optionally having a substituent, arylalkyl optionally having a substituent, alkenyl optionally having a substituent, alkynyl optionally having a substituent or heterocyclic alkyl optionally having a substituent, and U is halogen atom (fluorine atom, chlorine atom, bromine atom, iodine atom), or a leaving group such as alkanesulfonyloxy (e.g., methanesulfonyloxy, ethanesulfonyloxy, propanesulfonyloxy, trifluoromethanesulfonyloxy and the like), arylsulfonyloxy (e.g., phenylsulfonyloxy, tolylsulfonyloxy and the like) and the like.

In Production Method 2, the amino-protecting group $R^7$ of a compound of the formula [Ib] (also referred to as compound [Ib]) is eliminated by a method known per se to give a compound of the formula [Ic] (also referred to as compound [Ic]), which is then reacted with a compound of the formula [V] (also referred to as compound [V]), whereby a compound of the formula [Id] (also referred to as compound [Id]) is produced.

The "alkyl optionally having a substituent", "cycloalkyl", "cycloalkylalkyl", "aryl optionally having a substituent",
"arylalkyl optionally having a substituent", "alkenyl optionally having a substituent", "alkynyl optionally having a substituent" and "heterocyclic alkyl optionally having a substituent" at $R^8$ are as defined for $R^2$.

The amino-protecting group at $R^7$ is as defined for $R^6$.

In the Production Method 2, compound [Ic] is reacted with compound [V] in a solvent that does not inhibit the reaction, such as dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like; and a mixture thereof and the like, in the presence of a base, to give compound [Id].

In the Production Method 2, the base used for the reaction of compound [Ic] with compound [V] is exemplified, but not particulary limited to, inorganic base such as alkali metal carbonate (e.g., sodium carbonate, potassium carbonate, sodium hydrogencarbonate, potassium hydrogencarbonate and the like), alkali metal hydroxide (e.g., sodium hydroxide, potassium hydroxide and the like), metal hydride compound (e.g., sodium hydride, potassium hydride and calcium hydride and the like) and the like; and organic base such as alkali metal alkoxide (e.g., sodium methoxide, sodium ethoxide, potassium tert-butoxide and the like), amines (e.g., triethylamine, diisopropylethylamine and the like) and the like.

The amount of the compound [V] used in the Production Method 2 is generally 1–5 mol, preferably 1–3 mol, per 1 mol of compound [Ic]. The base is used in an amount of generally 1–5 mol, preferably 1–3 mol, per 1 mol of compound [Ic].

While the reaction conditions such as reaction temperature and reaction time and the like for the reaction of compound [Ic] with compound [V] in the Production Method 2 vary depending on the reagent, solvent and the like to be used in this reaction, the reaction generally proceeds at a temperature of from −30° C. to 150° C. for 30 min to about two dozen hours.

In the Production Method 2, $R^1$ of compound [Ib] is preferably lower alkyl. In this case, compound [Id] wherein $R^1$ is lower alkyl is obtained, and this compound may be led to the compound [Id] wherein $R^1$ is hydrogen atom, by hydrolysis according to a method known per se.

Production Method 3

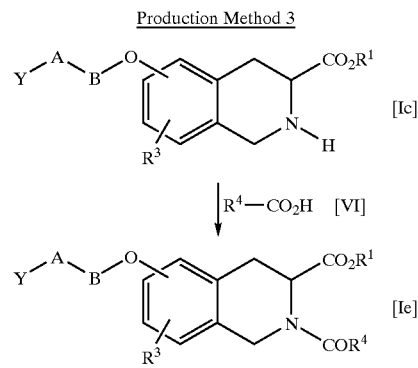

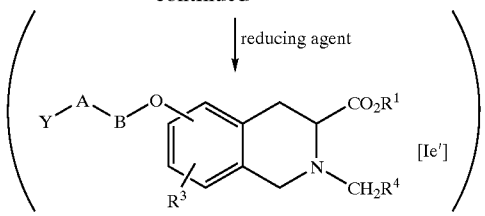

wherein $R^1$, $R^3$, $R^4$, A, B and Y are as defined above.

In Production Method 3, a compound of the formula [Ie] (also referred to as compound [Ie]) is synthesized by reacting compound [Ic] with a compound of the formula [VI] (also referred to as compound [VI]).

In the Production Method 3, compound [VI] may be used not only in the form of a free acid, but also in the form of a salt (e.g., sodium salt, potassium salt, calcium salt, triethylamine salt, pyridine salt and the like) or as a reactive derivative (e.g., acid halide such as acid chloride, acid bromide and the like; acid anhydride; mixed acid anhydride with substituted phosphoric acid such as dialkyl phosphate and the like, and alkyl carbonate such as monoethyl carbonate and the like; reactive amide which is amide with imidazole and the like; ester such as cyanomethyl ester and 4-nitrophenyl ester and the like), and the like.

In the Production Method 3, when the compound [VI] is used in the form of a free acid or a salt, this reaction is preferably carried out in the presence of a condensing agent. As the condensing agent, a dehydrating agent such as carbodiimide compound (e.g., N,N'-dicyclohexylcarbodiimide, 1-ethyl-3-(3'-dimethylaminopropyl)carbodiimide, N-cyclohexyl-N'-morpholinoethylcarbodiimide, N-cyclohexyl-N'-(4-diethylaminocyclohexyl)carbodiimide and the like), azolide compound (e.g., N,N'-carbonyldiimidazole, N,N'-thionyldiimidazole and the like) and the like, and the like can be used. The condensing agent is used in an amount of generally 1–5 mol, preferably 1–3 mol, per 1 mol of compound [Ic]. It is considered that, when a condensing agent is used, compound [VI] becomes a reactive derivative and proceeds to the reaction.

The Production Method 3 is generally performed in a solvent inert to the reaction. As the solvent, exemplified are acetone, dioxane, acetonitrile, chloroform, benzene, methylene chloride, ethylene chloride, tetrahydrofuran, ethyl acetate, N,N-dimethylformamide, pyridine, water and a mixed solvent thereof. In the Production Method 3, a base such as triethylamine, pyridine, 4-dimethylaminopyridine, potassium carbonate and the like can be used. When the base is used, it is used in an amount of generally 1–5 mol, preferably 1–3 mol, per 1 mol of compound [Ic].

In Production Method 3, compound [VI] is used in an amount of generally 1–5 mol, preferably 1–3 mol, per 1 mol of compound [Ic].

While the reaction conditions such as reaction temperature and reaction time and the like in the reaction of compound [VI] with compound [Ic] in the Production Method 3 vary depending on the reagent, solvent and the like to be used in this reaction, the reaction generally proceeds at a temperature of from −30° C. to 150° C. for 10 min to about a dozen hours.

In the Production Method 3, compound [Ie'] is obtained by reacting compound [VI] with compound [Ic], isolating and reducing the resulting compound [Ie]. This reduction reaction is carried out in a solvent that does not adversely influence the reaction (e.g., water, methanol, ethanol, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide, a mixture thereof and the like) in the presence of a reducing agent.

The reducing agent used in this reduction is exemplified by metal hydride complex (e.g., lithium aluminum hydride, sodium cyanoborohydride ($NaBH_3CN$), sodium borohydride and the like), borane and the like. The agent is not subject to any particular limitation as long as it is generally used for reducing a carbonyl group to a methylene group. The reducing agent is used in an amount of generally 1–5 mol, preferably 1–3 mol, per 1 mol of compound [Ie].

While the reaction conditions such as reaction temperature and reaction time and the like in the reduction reaction vary depending on the reagent, solvent and the like to be used in this reaction, the reaction generally proceeds at a temperature of from −30° C. to 150° C. for 30 min to about a dozen hours.

Production Method 4

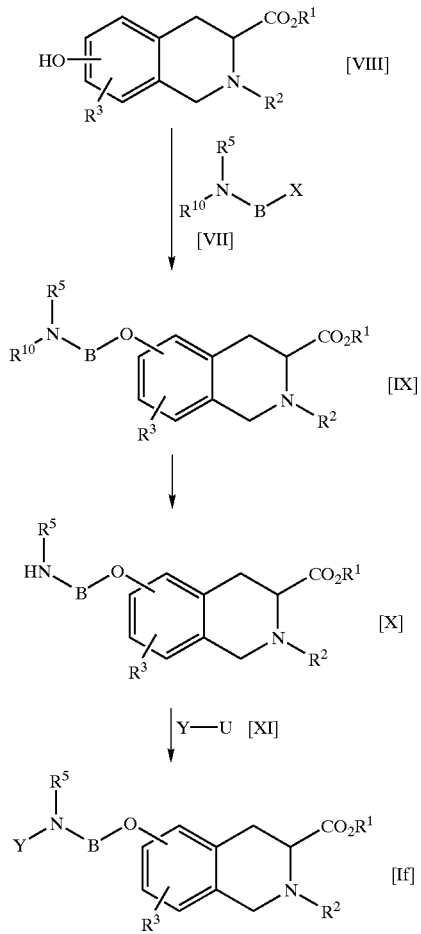

wherein $R^1$, $R^2$, $R^3$, $R^5$, B, X, Y and U are as defined above, and $R^{10}$ is an amino-protecting group.

The amino-protecting group at $R^{10}$ is as defined for $R^6$.

Production Method 4 is intended for the heterocyclic compound [I] wherein A is >N—$R^5$. In this method, compound of the formula [VII] (also referred to as compound [VII]) is reacted with compound of the formula [VIII] (also referred to as compound [VIII]) in the same manner as in Production Method 1 to give a compound of the formula [IX] (also referred to as compound [IX]), and the amino-protecting group at $R^{10}$ of the compound [IX] is eliminated by a method known per se to give a compound of the formula [X] (also referred to as compound [X]), which is then reacted with a compound of the formula [XI] (also referred to as compound [XI]), whereby a compound of the formula [If] (also referred to as compound [If]) is produced.

The reaction of compound [X] with compound [XI] in Production Method 4 is carried out in a solvent that does not adversely influence the reaction in the presence of a base. As the solvent, exemplified are dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like; and a mixture thereof. When compound [XI] can be used as a solvent, it can be used as a solvent.

The base used in the reaction of compound [X] with compound [XI] in the Production Method 4 is exemplified, but not particulary limited to, inorganic base such as alkali metal carbonate (e.g., sodium carbonate, potassium carbonate, sodium hydrogencarbonate, potassium hydrogencarbonate and the like), alkali metal hydroxide (e.g., sodium hydroxide, potassium hydroxide and the like), metal hydride compound (e.g., sodium hydride, potassium hydride, calcium hydride and the like) and the like; and organic base such as alkali metal alkoxide (e.g., sodium methoxide, sodium ethoxide, potassium tert-butoxide and the like) and amines (e.g., triethylamine, diisopropylethylamine and the like) and the like. The base is used in an amount of generally 1–5 mol, preferably 1–3 mol, per 1 mol of compound [X].

In Production Method 4, compound [XI] is used in a proportion of generally 1–5 mol, preferably 1–3 mol, per 1 mol of compound [X].

While the reaction conditions such as reaction temperature and reaction time and the like in the reaction of compound [X] with compound [XI] in the Production Method 4 vary depending on the reagent, solvent and the like to be used in this reaction, the reaction generally proceeds at a temperature of from −30° C. to 150° C. for 30 min to about a dozen hours.

Production Method 5

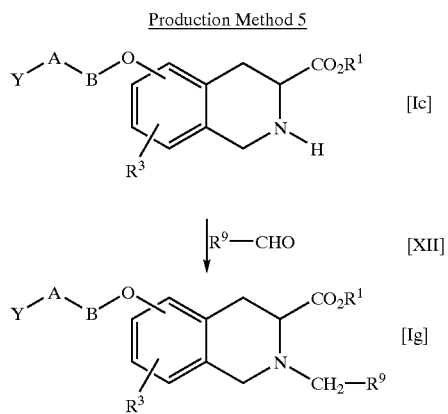

wherein $R^1$, $R^3$, A, B and Y are as defined above, $R^9$ is such a group as makes a group of the formula:—$CH_2$—$R^9$ alkyl optionally having a substituent, cycloalkylalkyl, arylalkyl optionally having a substituent, alkenyl optionally having a substituent, alkynyl optionally having a substituent or heterocyclic alkyl optionally having a substituent.

In Production Method 5, compound [Ic] is reacted with a compound of the formula [XII] (also referred to as compound [XII]), whereby a compound of the formula [Ig] (also referred to as compound [Ig]) is produced.

In a group of the formula: —$CH_2$—$R^9$, the "alkyl optionally having a substituent", "cycloalkylalkyl", "arylalkyl optionally having a substituent", "alkenyl optionally having a substituent", "alkynyl optionally having a substituent" and "heterocyclic alkyl optionally having a substituent" are as defined for $R^2$. In Production Method 5, compound [Ic] and compound [XII] are condensed in a solvent which does not inhibit the reaction (e.g., water, methanol, ethanol, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide, a mixture thereof and the like) in the presence of a reducing agent.

The reducing agent used in the Production Method 5 is not subject to any particular limitation, and is exemplified by metal hydride complex (e.g., lithium aluminum hydride, sodium cyanoborohydride ($NaBH_3CN$), sodium borohydride and the like), borane and the like.

In Production Method 5, compound [XII] is used in an amount of generally 1–5 mol, preferably 1–3 mol, per 1 mol of compound [Ic]. The reducing agent is used in an amount of generally 1–5 mol, preferably 1–3 mol, per 1 mol of compound [Ic].

While the reaction conditions such as reaction temperature and reaction time and the like in Production Method 5 vary with the reagent, solvent and the like to be used in this reaction, the reaction generally proceeds at a temperature of from −30° C. to 150° C. for 30 min to about a dozen hours.

The heterocyclic compound [I] obtained in the above-mentioned Production Methods 1–5 may be isolated by a conventional method, and, where necessary, purified by a conventional method such as recrystallization, preparative thin-layer chromatography, column chromatography and the like. The compound can be also purified into a salt as necessary.

The heterocyclic compound [I] may be converted to a pharmaceutically acceptable salt thereof by a method known per se.

The pharmaceutical composition comprising the heterocyclic compound [I] or a pharmaceutically acceptable salt thereof of the present invention may contain an additive and the like. As an additive, exemplified are excipient (e.g., starch, lactose, sugar, calcium carbonate, calcium phosphate and the like), binder (e.g., starch, gum arabic, carboxymethylcellulose, hydroxypropylcellulose, crystalline cellulose and the like), lubricant (e.g., magnesium stearate, talc and the like), disintegrator (e.g., carboxymethylcellulose calcium, talc and the like), and the like.

The above-mentioned components are mixed to give a preparation for oral administration such as capsule, tablet, powder, granule, dry syrup and the like, or a preparation for parenteral administration such as injection, suppository and the like, according to a method known per se.

While the dose of the heterocyclic compound [I] or a pharmaceutically acceptable salt thereof may vary according to the administration subject, symptom and other factors, when it is orally administered to an adult patient with, for example, diabetes, diabetic complications or hyperlipidemia, the single dose is approximately 1–500 mg/kg body weight, which is administered 1 to 3 times a day.

The heterocyclic compound [I] and a pharmaceutically acceptable salt of the present invention show a superior hypoglycemic action, a blood hypolipidemic action, an insulin resistance-improving action and a PPAR activating action in mammals (human, cattle, horse, dog, cat, rat, mouse, hamster and the like), and are useful as a hypoglycemic agent, a hypolipidemic agent, an insulin resistance improver, a therapeutic agent of diabetes, a therapeutic agent of diabetic complication, a glucose tolerance improver, an anti-atherosclerosis agent, an anti-obesity agent, an antiinflammatory agent, an agent for the prophylaxis or treatment of PPAR-mediated disease and an agent for the prophylaxis or treatment of syndrome X. To be specific, the heterocyclic compound [I] and a pharmaceutically acceptable salt of the present invention are useful for the prophylaxis or treatment of diabetes, diabetic complications, hyperlipidemia, atherosclerosis, hyperglycemia, diseases caused by insulin resistant impaired glucose tolerance, diseases caused by insulin resistance, obesity, inflammation, PPAR-mediated disease and syndrome X.

EXAMPLES

The present invention is explained in detail by referring to the following examples. The present invention is not limited by these examples in any way.

Example 1

Sodium 7-[2-(5-methyl-2-phenyloxazol-4-yl)ethoxy]-1,2,3,4-tetrahydroisoquinoline-(3S)-carboxylate (1) Ethyl 2-tert-butoxycarbonyl-7-hydroxy-1,2,3,4-tetrahydroisoquinoline-(3S)-carboxylate (1.50 g) and 2-(5-methyl-2-phenyloxazol-4-yl)ethyl methanesulfonate (2.50 g) were dissolved in N,N-dimethylformamide (20 ml). Thereto was added potassium carbonate (2.0 g) and the mixture was stirred at 80° C. for 5 hr. Ethyl acetate (100 ml) was added to the reaction mixture, and the mixture was washed with water (100 ml) and saturated brine (50 ml) and dried over $Na_2SO_4$. Ethyl acetate was evaporated under reduced pressure. The obtained residue was purified by silica gel column chromatography to give ethyl 2-tert-butoxycarbonyl-7-[2-(5-methyl-2-phenyloxazol-4-yl)ethoxy]-1,2,3,4-tetrahydroisoquinoline-(3S)-carboxylate (1.62 g).

Ethyl 2-tert-butoxycarbonyl-7-[2-(5-methyl-2-phenyloxazol-4-yl)ethoxy]-1,2,3,4-tetrahydroisoquinoline-(3S)-carboxylate:

IR v(neat) cm$^{-1}$; 2978, 2930, 1738, 1699, 1614, 1587.
$^1$H-NMR (CDCl$_3$) δ (ppm);
1.29 (3H, t, J=7.0 Hz), 1.46, 1.50 (9H, s, s), 2.36 (3H, s), 2.95 (2H, t, J=6.8 Hz), 2.90–3.30 (2H, m), 4.00–4.40 (4H, m), 4.51, 4.61 (2H, s, s), 4.70–4.90, 5.00–5.20 (1H, m, m), 6.60–6.90 (2H, m), 7.12 (1H, d, J=8.4 Hz), 7.30–7.55 (3H, m), 7.90–8.15 (2H, m).

(2) The compound (5.2 g) obtained in (1) above was dissolved in formic acid (20 ml). Thereto was added a 8.78N hydrogen chloride solution (6.0 ml) in 2-propanol under ice-cooling, and the mixture was stirred at room temperature for 10 min. Ethyl acetate (100 ml) was added to the reaction mixture, and the mixture was neutralized with saturated aqueous sodium hydrogencarbonate solution and separated into two layers. The obtained ethyl acetate layer was washed with saturated brine (50 ml) and dried over $Na_2SO_4$. Ethyl acetate was evaporated under reduced pressure to give ethyl 7-[2-(5-methyl-2-phenyloxazol-4-yl)ethoxy]-1,2,3,4-tetrahydroisoquinoline-(3S)-carboxylate (3.6 g).

Ethyl 7-[2-(5-methyl-2-phenyloxazol-4-yl)ethoxy]-1,2,3,4-tetrahydroisoquinoline-(3S)-carboxylate:

IR v (nujol) cm$^{-1}$; 3476, 1742, 1639, 1611, 1553.
$^1$H-NMR (CDCl$_3$) δ (ppm);
1.29 (3H, t, J=7.0 Hz), 2.02 (1H, s), 2.36 (3H, s), 2.80–3.10 (4H, m), 3.50–3.80 (1H, m), 4.00–4.40 (6H, m), 6.50–6.80 (2H, m), 7.00 (1H, d, J=8.4 Hz), 7.30–7.50 (3H, m), 7.90–8.10 (2H, m).

(3) The compound (1.11 g) obtained in (2) above was dissolved in methanol (20 ml). Thereto was added 1N aqueous sodium hydroxide solution (3.0 ml) and the mixture was stirred at room temperature for 2 hr. The solvent was evaporated under reduced pressure. Water (5 ml) was added to the obtained crystalline residue, and the crystals were collected by filtration to give the title compound (0.92 g).
IR v (nujol) cm$^{-1}$; 3427, 1589, 1504.
$^1$H-NMR (DMSO-d$_6$) δ (ppm);
2.35 (3H, s), 2.60–3.10 (6H, m), 3.86 (2H, br-s), 4.14 (2H, t, J=6.6 Hz), 6.50–6.80 (2H, m), 6.94 (1H, d, J=8.1 Hz), 7.40–7.60 (3H, m), 7.75–8.05 (2H, m).

Example 2

2-Benzyl-7-[2-(5-methyl-2-phenyloxazol-4-yl)ethoxy]-1,2,3,4-tetrahydroisoquinoline-(3S)-carboxylic acid (1) The compound (1.40 g) obtained in Example 1(2) was dissolved in N,N-dimethylformamide (20 ml). Thereto was added sodium hydride (160 mg, 60% suspension in oil) under ice-cooling, and the mixture was stirred at room temperature for 20 min. To the obtained mixture was dropwise added benzyl bromide (0.40 ml), and the mixture was stirred further at the same temperature for 1 hr. Ethyl acetate (50 ml) was added to the reaction mixture, and the mixture was washed with water (50 ml) and saturated brine (30 ml) and dried over $Na_2SO_4$. Ethyl acetate was evaporated under reduced pressure. The obtained residue was purified by silica gel column chromatography to give ethyl 2-benzyl-7-[2-(5-methyl-2-phenyloxazol-4-yl)ethoxy]-1,2,3,4-tetrahydroisoquinoline-(3S)-carboxylate (1.38 g).

Ethyl 2-benzyl-7-[2-(5-methyl-2-phenyloxazol-4-yl)ethoxy]-1,2,3,4-tetrahydroisoquinoline-(3S)-carboxylate:

IR v (nujol) cm$^{-1}$; 1728, 1639, 1614, 1551.
$^1$H-NMR (CDCl$_3$) δ (ppm);
1.21 (3H, t, J=7.0 Hz), 2.34 (3H, s), 2.92 (2H, t, J=7.0 Hz), 3.05–3.20 (2H, m), 3.60–4.00 (5H, m), 4.12 (2H, q, J=7.0 Hz), 4.16 (2H, t, J=7.0 Hz), 6.51 (1H, d, J=2.0 Hz), 6.68 (1H, dd, J=2.0, 8.4 Hz), 6.99 (1H, d, J=8.4 Hz), 7.30–7.50 (8H, m), 7.80–8.10 (2H, m).

(2) The compound (8.20 g) obtained in (1) above was dissolved in 80 ml of a mixed solution of tetrahydrofuran-methanol (3:1). Thereto was added 2N aqueous lithium hydroxide solution (42 ml), and the mixture was stirred at 50° C. for 2 hr. The solvent was evaporated under reduced pressure, and the obtained residue was acidified with citric acid. The precipitated crystals were collected by filtration. The obtained crude crystals (9.0 g) were recrystallized from methanol to give the title compound (6.33 g).
IR v (nujol) cm$^{-1}$; 1638, 1501.
$^1$H-NMR (DMSO-d$_6$) δ (ppm);
2.33 (3H, s), 2.65–3.30 (4H, m), 3.50–4.00 (5H, m), 4.00–6.20 (1H, br), 4.13 (2H, t, J=7.0 Hz), 6.59 (1H, br-s), 6.68 (1H, br-d, J=8.4 Hz), 7.01 (1H, d, J=8.4 Hz), 7.32 (5H, s), 7.35–7.70 (3H, m), 7.85–8.10 (2H, m).

Example 3

2-Acetyl-7-[2-(5-methyl-2-phenyloxazol-4-yl)ethoxy]-1,2,3,4-tetrahydroisoquinoline-(3S)-carboxylic acid (1) The compound (800 mg) obtained in Example 1(2) was dissolved in methylene chloride (8.0 ml). Thereto was added acetic anhydride (0.23 ml) under ice-cooling, and the mixture was stirred at room temperature for 10 min. Ethyl acetate (30 ml) was added to the reaction mixture, and the mixture was neutralized with saturated aqueous sodium hydrogencarbonate solution, and then the two layers were separated. The obtained organic layer was washed with saturated brine (10 ml) and dried over $Na_2SO_4$. The solvent was evaporated under reduced pressure. The obtained residue was purified by silica gel column chromatography to give ethyl 2-acetyl-7-[2-(5-methyl-2-phenyloxazol-4-yl)ethoxy]-1,2,3,4-tetrahydroisoquinoline-(3S)-carboxylate (873 mg).

Ethyl 2-acetyl-7-[2-(5-methyl-2-phenyloxazol-4-yl)ethoxy]-1,2,3,4-tetrahydroisoquinoline-(3S)-carboxylate:

IR ν (nujol) $cm^{-1}$; 1732, 1651, 1555.
$^1$H-NMR ($CDCl_3$) δ (ppm);
1.12 (3H, t, J=7.0 Hz), 2.13, 2.21 (3H, s, s), 2.36 (3H, s), 2.95 (2H, t, J=6.6 Hz), 3.05–3.30 (2H, m), 4.04 (2H, q, J=7.0 Hz), 4.22 (2H, t, J=6.6 Hz), 4.62 (2H, s), 5.45 (1H, dd, J=4.0, 5.7 Hz), 6.55–6.85 (2H, m), 7.04 (1H, d, J=8.2 Hz), 7.30–7.50 (3H, m), 7.85–8.10 (2H, m).

(2) The compound (800 mg) obtained in (1) above was dissolved in 5.0 ml of a mixed solution of tetrahydrofuran-methanol (3:1). Thereto was added 1N aqueous lithium hydroxide solution (3.0 ml), and the mixture was stirred at room temperature for 30 min. The solvent was evaporated under reduced pressure, and the obtained residue was acidified with citric acid. The precipitated crystals were collected by filtration to give the title compound (668 mg).

IR ν (nujol) $cm^{-1}$; 3400, 1732, 1641, 1612, 1555.
$^1$H-NMR ($CDCl_3$) δ (ppm);
2.10, 2.17 (3H, s, s), 2.32 (3H, s), 2.70–3.30 (4H, m), 3.90–4.20 (2H, m), 4.30–4.90 (2H, m), 5.35–5.60 (1H, m), 6.50–6.80 (2H, m), 7.03 (1H, d, J=8.1 Hz), 7.30–7.60 (3H, m), 7.80–8.10 (2H, m).

Example 4

2-Methyl-7-[2-(5-methyl-2-phenyloxazol-4-yl)ethoxy]-1,2,3,4-tetrahydroisoquinoline-(3S)-carboxylic acid (1) The compound (1.0 g) obtained in Example 1(2) was dissolved in methanol (10 ml). Thereto were added formalin (0.4 ml) and sodium cyanoborohydride (310 mg), and the mixture was stirred at room temperature for 1 hr. Methanol was evaporated under reduced pressure. Ethyl acetate (20 ml) was added to the obtained residue, and the mixture was washed with water (20 ml) and saturated brine (10 ml) and dried over $Na_2SO_4$. Ethyl acetate was evaporated under reduced pressure. The obtained residue was purified by silica gel column chromatography to give ethyl 2-methyl-7-[2-(5-methyl-2-phenyloxazol-4-yl)ethoxy]-1,2,3,4-tetrahydroisoquinoline-(3S)-carboxylate (1.08 g).

Ethyl 2-methyl-7-[2-(5-methyl-2-phenyloxazol-4-yl)ethoxy]-1,2,3,4-tetrahydroisoquinoline-(3S)-carboxylate:

IR ν (neat) $cm^{-1}$; 2926, 2874, 1732, 1641, 1614.
$^1$H-NMR ($CDCl_3$) δ (ppm);
1.25 (3H, t, J=7.0 Hz), 2.35 (3H, s), 2.50 (3H, s), 2.94 (2H, t, J=6.8 Hz), 3.02 (2H, d, J=6.0 Hz), 3.45 (1H, t, J=6.0 Hz), 3.64 (1H, d, J=15.6 Hz), 3.98 (1H, d, J=15.6 Hz), 4.17 (2H, q, J=7.0 Hz), 4.20 (2H, t, J=6.6 Hz), 6.56 (1H, d, J=2.0 Hz), 6.70 (1H, dd, J=2.0, 8.4 Hz), 6.98 (1H, d, J=8.4 Hz), 7.30–7.50 (3H, m), 7.85–8.10 (2H, m).

(2) The compound (1.08 g) obtained in (1) above was dissolved in 10 ml of a mixed solution of tetrahydrofuran-methanol (3:1). Thereto was added 1N aqueous lithium hydroxide solution (7.5 ml), and the mixture was stirred at room temperature for 1 hr. The solvent was evaporated under reduced pressure, and the obtained residue was acidified with citric acid. The precipitated crystals were collected by filtration to give the title compound (0.74 g).

IR ν (nujol) $cm^{-1}$; 1616, 1555, 1541, 1506.
$^1$H-NMR (DMSO-$d_6$) δ (ppm);
2.36 (3H, s), 2.55 (3H, s), 2.70–3.10 (4H, m), 3.40–3.60 (1H, m), 3.70–4.30 (4H, m), 6.60–6.80 (2H, m), 7.05 (1H, d, J=8.6 Hz), 7.35–7.65 (3H, m), 7.75–8.10 (2H, m).

Example 5

2-Hexanoyl-7-[2-(5-methyl-2-phenyloxazol-4-yl)ethoxy]-1,2,3,4-tetrahydroisoquinoline-(3S)-carboxylic acid (1) The compound (1.0 g) obtained in Example 1(2) was dissolved in methylene chloride (10 ml). Thereto were added hexanoyl chloride (0.41 ml) and triethylamine (0.51 ml) under ice-cooling, and the mixture was stirred at the same temperature for 10 min. Ethyl acetate (70 ml) was added to the reaction mixture, and the mixture was washed with 10% aqueous citric acid solution (50 ml), saturated aqueous sodium hydrogencarbonate solution (50 ml) and then saturated brine (50 ml) and dried over $Na_2SO_4$. The solvent was evaporated under reduced pressure. The obtained residue was purified by silica gel column chromatography to give ethyl 2-hexanoyl-7-[2-(5-methyl-2-phenyloxazol-4-yl)ethoxy]-1,2,3,4-tetrahydroisoquinoline-(3S)-carboxylate (1.02 g).

Ethyl 2-hexanoyl-7-[2-(5-methyl-2-phenyloxazol-4-yl)ethoxy]-1,2,3,4-tetrahydroisoquinoline-(3S)-carboxylate:

IR ν (nujol) $cm^{-1}$; 1736, 1653, 1587.
$^1$H-NMR ($CDCl_3$) δ (ppm);
0.70–1.90 (12H, m), 2.20–2.60 (2H, m), 2.36 (3H, s), 2.95 (2H, t, J=6.8 Hz), 3.10–3.20 (2H, m), 4.04 (2H, q, J=7.0 Hz), 4.22 (2H, t, J=7.0 Hz), 4.63 (2H, s), 5.45 (1H, dd, J=4.0, 5.4 Hz), 6.60–6.90 (2H, m), 7.04 (1H, d, J=8.1 Hz), 7.30–7.50 (3H, m), 7.80–8.10 (2H, m).

(2) The compound (1.02 g) obtained in (1) above was dissolved in 10 ml of a mixed solution of tetrahydrofuran-methanol (3:1). Thereto was added 1N aqueous lithium hydroxide solution (6.0 ml), and the mixture was stirred at room temperature for 4 hr. The solvent was evaporated under reduced pressure, and the obtained residue was acidified with citric acid. The precipitated crystals were collected by filtration to give the title compound (0.56 g).

IR ν (nujol) $cm^{-1}$; 1742, 1641, 1612, 1572.
$^1$H-NMR ($CDCl_3$) δ (ppm);
0.88 (3H, br-t, J=6.0 Hz), 1.10–1.90 (6H, m), 2.32 (3H, s), 2.30–2.50 (2H, m), 2.70–3.30 (4H, m), 4.07 (2H, t, J=7.0 Hz), 4.60 (2H, s), 5.40–5.60 (1H, m), 6.60–6.80 (2H, m), 7.05 (1H, d, J=8.6 Hz), 7.35–7.65 (3H, m), 7.75–8.10 (2H, m).

Example 6

2-Hexyl-7-[2-(5-methyl-2-phenyloxazol-4-yl)ethoxy]-1,2,3,4-tetrahydroisoquinoline-(3S)-carboxylic acid (1) The compound (1.20 g) obtained in Example 1(2) was dissolved in N,N-dimethylformamide (12 ml). Thereto were added hexyl iodide (0.65 ml) and potassium carbonate (0.82 g) and the mixture was stirred at 50° C. for 15 hr. Water (100 ml) was added to the reaction mixture, and the mixture was extracted twice with ethyl acetate (50 ml). The ethyl acetate layer was washed with saturated brine (100 ml) and dried over $Na_2SO_4$. Ethyl acetate was evaporated under reduced pressure. The obtained residue was purified by silica gel column chromatography to give ethyl 2-hexyl-7-[2-(5-methyl-2-phenyloxazol-4-yl)ethoxy]-1,2,3,4-tetrahydroisoquinoline-(3S)-carboxylate (1.05 g).

Ethyl 2-hexyl-7-[2-(5-methyl-2-phenyloxazol-4-yl)ethoxy]-1,2,3,4-tetrahydroisoquinoline-(3S)-carboxylate:

IR ν (nujol) $cm^{-1}$; 1724, 1643, 1611.

$^1$H-NMR ($CDCl_3$) δ (ppm);

0.88 (3H, br-t, J=5.0 Hz), 1.10–1.75 (11H, m), 2.35 (3H, s), 2.50–2.80 (2H, m), 2.94 (2H, t, J=7.0 Hz), 3.02 (2H, d, J=5.5 Hz), 3.68 (1H, t, J=5.5 Hz), 3.83 (1H, s), 3.94 (1H, s), 4.12 (2H, q, J=7.0 Hz), 4.20 (2H, t, J=7.0 Hz), 6.50–6.80 (2H, m), 6.97 (1H, d, J=8.4 Hz), 7.30–7.60 (3H, m), 7.80–8.10 (2H, m).

(2) The compound (1.0 g) obtained in (1) above was dissolved in 10 ml of a mixed solution of tetrahydrofuran-methanol (3:1). Thereto was added 2N aqueous lithium hydroxide solution (5.1 ml), and the mixture was stirred at room temperature for 11 hr. The solvent was evaporated under reduced pressure, and the obtained residue was acidified with citric acid. The precipitated crystals were collected by filtration to give the title compound (0.80 g).

IR ν (nujol) $cm^{-1}$; 1620, 1555, 1506.

$^1$H-NMR ($CDCl_3$) δ (ppm);

0.89 (3H, br-t, J=6.0 Hz), 1.00–1.45 (6H, m), 1.50–1.90 (2H, m), 2.36 (3H, s), 2.70–3.30 (2H, m), 2.93 (2H, t, J=6.2 Hz), 3.15 (2H, d, J=6.4 Hz), 3.75 (1H, t, J=6.4 Hz), 4.00–4.40 (4H, m), 6.23 (1H, br-s), 6.60–6.85 (2H, m), 7.06 (1H, d, J=8.4 Hz), 7.30–7.60 (3H, m), 7.80–8.10 (2H, m).

Example 7

2-Isobutyl-7-[2-(5-methyl-2-phenyloxazol-4-yl)ethoxy]-1,2,3,4-tetrahydroisoquinoline-(3S)-carboxylic acid (1) The compound (1.40 g) obtained in Example 1(2) was dissolved in N,N-dimethylformamide (14 ml). Thereto were added isobutyl iodide (1.20 ml) and potassium carbonate (0.95 g), and the mixture was stirred at 50° C. for 3 days. Water (100 ml) was added to the reaction mixture, and the mixture was extracted twice with ethyl acetate (50 ml). The obtained ethyl acetate layer was washed with saturated brine (100 ml) and dried over $Na_2SO_4$. Ethyl acetate was evaporated under reduced pressure. The obtained residue was purified by silica gel column chromatography to give ethyl 2-isobutyl-7-[2-(5-methyl-2-phenyloxazol-4-yl)ethoxy]-1,2,3,4-tetrahydroisoquinoline-(3S)-carboxylate (1.15 g).

Ethyl 2-isobutyl-7-[2-(5-methyl-2-phenyloxazol-4-yl)ethoxy]-1,2,3,4-tetrahydroisoquinoline-(3S)-carboxylate:

IR ν (nujol) $cm^{-1}$; 1719, 1645, 1614, 1506.

$^1$H-NMR ($CDCl_3$) δ (ppm);

0.89 (6H, d, J=6.6 Hz), 1.19 (3H, t, J=7.0 Hz), 1.70–1.90 (1H, m), 2.35 (3H, s), 2.10–2.50 (2H, m), 2.94 (2H, t, J=7.0 Hz), 3.02 (2H, d, J=5.2 Hz), 3.66 (1H, t, J=5.2 Hz), 3.83 (1H, s), 3.92 (1H, s), 4.16 (2H, q, J=7.0 Hz), 4.20 (2H, t, J=7.0 Hz), 6.45–6.75 (2H, m), 6.97 (1H, d, J=8.2 Hz), 7.25–7.50 (3H, m), 7.85–8.10 (2H, m).

(2) The compound (1.05 g) obtained in (1) above was dissolved in 10 ml of a mixed solution of tetrahydrofuran-methanol (3:1). Thereto was added 2N aqueous lithium hydroxide solution (5.7 ml), and the mixture was stirred at room temperature for 24 hr. The solvent was evaporated under reduced pressure, and the obtained residue was acidified with citric acid. The precipitated crystals were collected by filtration to give the title compound (0.83 g).

IR ν (nujol) $cm^{-1}$; 3339, 1620, 1553, 1508.

$^1$H-NMR ($CDCl_3$) δ (ppm); 0.95 (3H, d, J=6.7 Hz), 1.01 (3H, d, J=7.0 Hz), 1.95–2.15 (1H, m), 2.36 (3H, s), 2.60–2.80 (2H, m), 2.94 (2H, t, J=6.7 Hz), 3.16 (2H, d, J=6.6 Hz), 3.70 (1H, t, J=6.6 Hz), 4.11 (2H, s), 4.18 (2H, t, J=6.6 Hz), 4.84 (1H, br-s), 6.60–6.90 (2H, m), 7.49 (1H, d, J=8.1 Hz), 7.25–7.50 (3H, m), 7.85–8.10 (2H, m).

Example 8

2-Cyclohexylmethyl-7-[2-(5-methyl-2-phenyloxazol-4-yl)ethoxy]-1,2,3,4-tetrahydroisoquinoline-(3S)-carboxylic acid (1) The compound (1.40 g) obtained in Example 1(2) was dissolved in N,N-dimethylformamide (14 ml). Thereto were added cyclohexylmethyl bromide (1.44 ml) and potassium carbonate (0.95 g), and the mixture was stirred at 50° C. for 2 days. Water (100 ml) was added to the reaction mixture, and the mixture was extracted twice with ethyl acetate (50 ml). The ethyl acetate layer was washed with saturated brine (100 ml) and dried over $Na_2SO_4$. Ethyl acetate was evaporated under reduced pressure. The obtained residue was purified by silica gel column chromatography to give ethyl 2-cyclohexylmethyl-7-[2-(5-methyl-2-phenyloxazol-4-yl)ethoxy]-1,2,3,4-tetrahydroisoquinoline-(3S)-carboxylate (1.0 g).

Ethyl 2-cyclohexylmethyl-7-[2-(5-methyl-2-phenyloxazol-4-yl)ethoxy]-1,2,3,4-tetrahydroisoquinoline-(3S)-carboxylate:

IR ν (nujol) $cm^{-1}$; 1728, 1638, 1614, 1504.

$^1$H-NMR ($CDCl_3$) δ (ppm);

0.80–2.00 (11H, m), 1.19 (3H, t, J=7.0 Hz), 2.36 (3H, s), 2.40–2.55 (2H, m), 2.94 (2H, t, J=7.1 Hz), 3.00 (2H, d, J=5.3 Hz), 3.65 (1H, t, J=5.3 Hz), 3.82 (1H, s), 3.92 (1H, s), 4.05 (2H, t, J=7.0 Hz), 4.16 (2H, q, J=7.0 Hz), 6.50–6.80 (2H, m), 6.97 (1H, d, J=8.1 Hz), 7.30–7.50 (3H, m), 7.80–8.10 (2H, m).

(2) The compound (0.95 g) obtained in (1) above was dissolved in 28 ml of a mixed solution of tetrahydrofuran-methanol (3:1). Thereto was added 2N aqueous lithium hydroxide solution (7.13 ml), and the mixture was stirred at room temperature for 3 days. The solvent was evaporated under reduced pressure, and the obtained residue was acidified with citric acid. The precipitated crystals were collected by filtration to give the title compound (0.76 g).

IR ν (nujol) $cm^{-1}$; 3319, 1624, 1506.

$^1$H-NMR ($CDCl_3$) δ (ppm);

0.70–2.10 (11H, m), 2.36 (3H, s), 2.40–2.55 (2H, m), 2.93 (2H, t, J=6.4 Hz), 3.16 (2H, d, J=7.2 Hz), 3.70 (1H, t, J=7.2 Hz), 4.00–4.30 (4H, m), 5.30 (1H, br-s), 6.60–6.90 (2H, m), 7.08 (1H, d, J=8.4 Hz), 7.30–7.50 (3H, m), 7.80–8.10 (2H, m).

Example 9

7-[2-(5-Methyl-2-phenyloxazol-4-yl)ethoxy]-2-(3-phenylpropyl)-1,2,3,4-tetrahydroisoquinoline-(3S)-carboxylic acid (1) The compound (1.40 g) obtained in Example 1(2) was dissolved in N,N-dimethylformamide (14 ml). Thereto were added 3-phenylpropyl bromide (0.78 ml) and potassium carbonate (0.95 g), and the mixture was stirred at 50° C. for 22 hr. Water (100 ml) was added to the reaction mixture, and the mixture was extracted twice with ethyl acetate (50 ml). The ethyl acetate layer was washed with saturated brine (100 ml) and dried over $Na_2SO_4$. Ethyl acetate was evaporated under reduced pressure. The obtained residue was purified by silica gel column chromatography to give ethyl 7-[2-(5-methyl-2-phenyloxazol-4-yl)ethoxy]-2-(3-phenylpropyl)-1,2,3,4-tetrahydroisoquinoline-(3S)-carboxylate (1.05 g).

Ethyl 7-[2-(5-methyl-2-phenyloxazol-4-yl)ethoxy]-2-(3-phenylpropyl)-1,2,3,4-tetrahydroisoquinoline-(3S)-carboxylate IR ν (nujol) $cm^{-1}$; 1720, 1647, 1612, 1504.
$^1$H-NMR ($CDCl_3$) δ (ppm);
1.17 (3H, t, J=7.0 Hz), 1.60–2.05 (2H, m), 2.35 (3H, s), 2.50–2.80 (4H, m), 2.94 (2H, t, J=7.1 Hz), 3.04 (2H, d, J=5.7 Hz), 3.67 (1H, t, J=5.7 Hz), 3.84 (1H, s), 3.94 (1H, s), 4.04 (2H, t, J=7.1 Hz), 4.16 (2H, q, J=7.0 Hz), 6.50–6.80 (2H, m), 7.07 (1H, d, J=9.0 Hz), 7.20 (5H, s), 7.10–7.50 (3H, m), 7.80–8.10 (2H, m).

(2) The compound (1.0 g) obtained in (1) above was dissolved in 10 ml of a mixed solution of tetrahydrofuran-methanol (3:1). Thereto was added 2N aqueous lithium hydroxide solution (4.77 ml), and the mixture was stirred at room temperature for 10 hr. The solvent was evaporated under reduced pressure, and the obtained residue was acidified with citric acid. The precipitated crystals were collected by filtration to give the title compound (0.66 g).
IR ν (nujol) $cm^{-1}$; 3346, 1616, 1556, 1506.
$^1$H-NMR ($CDCl_3$) δ (ppm);
1.70–2.20 (3H, m), 2.35 (3H, s), 2.40–2.70 (4H, m), 2.70–3.30 (2H, m), 2.92 (2H, t, J=6.3 Hz), 3.10 (2H, d, J=7.0 Hz), 3.65 (1H, t, J=7.0 Hz), 3.90–4.30 (4H, m), 5.12 (1H, br-s), 6.55–6.80 (2H, m), 6.90–7.25 (6H, m), 7.25–7.55 (3H, m), 7.80–8.10 (2H, m).

Example 10

2-Benzoyl-7-[2-(5-methyl-2-phenyloxazol-4-yl)ethoxy]-1,2,3,4-tetrahydroisoquinoline-(3S)-carboxylic acid (1) The compound (1.4 g) obtained in Example 1(2) was dissolved in methylene chloride (14 ml). Thereto were added benzoyl chloride (0.48 ml) and triethylamine (0.72 ml) under ice-cooling, and the mixture was stirred at the same temperature for 15 min. Ethyl acetate (100 ml) was added to the reaction mixture, and the mixture was washed successively with 10% aqueous citric acid solution (50 ml), saturated aqueous sodium hydrogencarbonate solution (50 ml) and then saturated brine (50 ml) and dried over $Na_2SO_4$. The solvent was evaporated under reduced pressure. The obtained residue was purified by silica gel column chromatography to give ethyl 2-benzoyl-7-[2-(5-methyl-2-phenyloxazol-4-yl)ethoxy]-1,2,3,4-tetrahydroisoquinoline-(3S)-carboxylate (1.16 g).

Ethyl 2-benzoyl-7-[2-(5-methyl-2-phenyloxazol-4-yl)ethoxy]-1,2,3,4-tetrahydroisoquinoline-(3S)-carboxylate IR ν (nujol) $cm^{-1}$; 1734, 1638, 1612, 1591.
$^1$H-NMR ($CDCl_3$) δ (ppm);
0.75–1.15 (3H, m), 2.35 (3H, s), 2.93 (2H, t, J=6.6 Hz), 3.05–3.25 (2H, m), 3.85–4.40 (4H, m), 4.20–4.80 (2H, m), 5.00–5.60 (1H, m), 6.47 (1H, br-s), 6.72 (1H, br-d, J=8.4 Hz), 7.05 (1H, br-d, J=8.4 Hz), 7.30–7.60 (8H, m), 7.80–8.10 (2H, m).

(2) The compound (1.0 g) obtained in (1) above was dissolved in 10 ml of a mixed solution of tetrahydrofuran-methanol (3:1). Thereto was added 1N aqueous lithium hydroxide solution (6.0 ml), and the mixture was stirred at room temperature for 1.5 hr. The solvent was evaporated under reduced pressure. Thereto was added water (20 ml), and the mixture was washed with ethyl acetate (10 ml). The obtained aqueous layer was acidified with 6N hydrochloric acid, and the mixture was extracted twice with diethyl ether (20 ml). The diethyl ether layer was washed with saturated brine (30 ml) and dried over $Na_2SO_4$. Diethyl ether was evaporated under reduced pressure. The obtained residue was recrystallized from methanol to give the title compound (0.75 g).
IR ν (nujol) $cm^{-1}$; 1730, 1636, 1551.
$^1$H-NMR ($CDCl_3$) δ (ppm);
2.32 (3H, s), 2.87 (2H, t, J=6.4 Hz), 3.00–3.35 (2H, m), 4.02 (2H, t, J=6.4 Hz), 4.40–4.90 (2H, m), 4.90–5.30 (1H, br), 5.00–5.65 (1H, m), 6.40 (1H, br-s), 6.50–6.80 (1H, m), 7.03 (1H, d, J=8.4 Hz), 7.20–7.60 (8H, m), 7.75–8.05 (2H, m).

Example 11

Sodium 2-benzyl-7-[2-(N-methyl-N-(pyridin-2-yl)amino)ethoxy]-1,2,3,4-tetrahydroisoquinoline-(3S)-carboxylate (1) Ethyl 2-benzyl-7-hydroxy-1,2,3,4-tetrahydroisoquinoline-(3S)-carboxylate (1.38 g) was dissolved in N,N-dimethylformamide (10 ml). Thereto was added sodium hydride (210 mg, 60% suspension in oil) under ice-cooling and the mixture was stirred at room temperature for 30 min. Thereto was added 2-(N-tert-butoxycarbonyl-N-methylamino)ethyl methanesulfonate (1.30 g) and the mixture was stirred further at the same temperature for 1 hr. Ethyl acetate (50 ml) was added to the reaction mixture, and the mixture was washed with water (50 ml) and saturated brine (30 ml) and dried over $Na_2SO_4$. Ethyl acetate was evaporated under reduced pressure. The obtained residue was purified by silica gel column chromatography to give ethyl 2-benzyl-7-[2-(N-tert-butoxycarbonyl-N-methylamino)ethoxy]-1,2,3,4-tetrahydroisoquinoline-(3S)-carboxylate (1.44 g).

Ethyl 2-benzyl-7-[2-(N-tert-butoxycarbonyl-N-methylamino)ethoxy]-1,2,3,4-tetrahydroisoquinoline-(3S)-carboxylate IR ν(neat) $cm^{-1}$; 2978, 2932, 1732, 1695, 1614.
$^1$H-NMR ($CDCl_3$) δ (ppm);
1.23 (3H, t, J=7.0 Hz), 1.44 (9H, s), 2.95 (3H, s), 3.08 (2H, d, J=4.9 Hz), 3.54 (2H, t, J=5.5 Hz), 3.60–4.30 (7H, m), 6.50 (1H, d, J=2.0 Hz), 6.68 (1H, dd, J=2.0, 8.1 Hz), 7.01 (1H, d, J=8.1 Hz), 7.20–7.50 (5H, m).

(2) The compound (1.44 g) obtained in (1) above was dissolved in formic acid (7.0 ml). Thereto was added 8.78N hydrogen chloride solution (2.0 ml) in 2-propanol, and the mixture was stirred at room temperature for 15 min. Ethyl acetate (100 ml) was added to the reaction mixture, and the mixture was neutralized with saturated aqueous sodium hydrogencarbonate solution, and then the two layers were separated. The obtained ethyl acetate layer was washed with saturated brine (50 ml) and dried over $Na_2SO_4$. Ethyl acetate was evaporated under reduced pressure to give ethyl 2-benzyl-7-(2-methylaminoethoxy)-1,2,3,4-tetrahydroisoquinoline-(3S)-carboxylate (1.08 g).

Ethyl 2-benzyl-7-(2-methylaminoethoxy)-1,2,3,4-tetrahydroisoquinoline-(3S)-carboxylate IR ν (neat) $cm^{-1}$; 3332, 1732, 1612, 1504.
$^1$H-NMR ($CDCl_3$) δ (ppm);
1.22 (3H, t, J=7.0 Hz), 2.41 (1H, br-s), 2.49 (3H, s), 2.95 (2H, t, J=5.5 Hz), 3.08 (2H, d, J=4.9 Hz), 3.60–4.25 (7H, m), 6.52 (1H, d, J=2.0 Hz), 6.70 (1H, dd, J=2.0, 8.4 Hz), 7.00 (1H, d, J=8.4 Hz), 7.20–7.50 (5H, m).

(3) The compound (1.05 g) obtained in (2) above was dissolved in 2-chloropyridine (2.0 ml), and the mixture was stirred at 140° C. for 16 hr. The reaction mixture was purified by silica gel column chromatography to give ethyl 2-benzyl-7-[2-(N-methyl-N-(pyridin-2-yl)amino)ethoxy]-1,2,3,4-tetrahydroisoquinoline-(3S)-carboxylate (0.5 g).

Ethyl 2-benzyl-7-[2-(N-methyl-N-(pyridin-2-yl)amino)ethoxy]-1,2,3,4-tetrahydroisoquinoline-(3S)-carboxylate IR ν (neat) $cm^{-1}$; 2932, 2905, 1732, 1597, 1560, 1504.
$^1$H-NMR ($CDCl_3$) δ (ppm);
1.22 (3H, t, J=7.0 Hz), 3.06 (2H, d, J=6.2 Hz), 3.11 (3H, s), 3.60–4.30 (11H, m), 6.40–6.80 (4H, m), 6.97 (1H, d, J=8.4 Hz), 7.20–7.50 (6H, m), 8.00–8.20 (1H, m).

(4) The compound (488 mg) obtained in (3) above was dissolved in 5.0 ml of a mixed solution of tetrahydrofuran-methanol (3:1). Thereto was added 1N aqueous sodium hydroxide solution (2.2 ml), and the mixture was stirred at room temperature for 6 hr. The solvent was evaporated under reduced pressure. Water (10 ml) and then saline were added to supersaturation, and the mixture was extracted three times with ethyl acetate (30 ml). The ethyl acetate layer was washed with saturated brine (10 ml) and dried over $Na_2SO_4$. Ethyl acetate was evaporated under reduced pressure. Diethyl ether was added to the obtained residue. The solid was collected by filtration to give the title compound (356 mg).
IR ν (nujol) $cm^{-1}$; 1597, 1497.
$^1$H-NMR (MeOH-$d_4$) δ (ppm);
2.95–3.20 (2H, m), 3.07 (3H, s), 3.40–4.20 (9H, m), 6.40–6.70 (4H, m), 6.92 (1H, d, J=8.4 Hz), 7.20–7.50 (3H, m), 7.90–8.15 (1H, m).

Example 12

Sodium 2-benzyl-7-[2-(5-ethyl-pyridin-2-yl)ethoxy] 1,2,3,4-tetrahydroisoquinoline-(3S)-carboxylate (1) Ethyl 2-benzyl-7-hydroxy-1,2,3,4-tetrahydroisoquinoline-(3S)-carboxylate (1.0 g) was dissolved in N,N-dimethylformamide (10 ml). Thereto was added sodium hydride (200 mg, 60% suspension in oil) under ice-cooling and the mixture was stirred at room temperature for 30 mm to give solution (A). Separately, 5-ethyl-2-pyridineethanol (1.5 g) and triethylamine (1.68 ml) were dissolved in methylene chloride (40 ml). Thereto was added trifluoromethanesulfonic anhydride (2.0 ml) under ice-cooling, and the mixture was stirred at room temperature for 30 min. The reaction mixture was washed with water (30 ml) and dried over $Na_2SO_4$. Methylene chloride was evaporated under reduced pressure. The obtained 2-(5-ethylpyridin-2-yl)ethyl trifluoromethanesulfonate (2.81 g) was added to the above-mentioned solution (A), and the mixture was stirred at room temperature for 30 min. Ethyl acetate (100 ml) was added to the reaction mixture, and the mixture was washed with water (50 ml) and saturated brine (50 ml) and dried over $Na_2SO_4$. Ethyl acetate was evaporated under reduced pressure. The obtained residue was purified by silica gel column chromatography to give ethyl 2-benzyl-7-[2-(5-ethyl-pyridin-2-yl)ethoxy]-1,2,3,4-tetrahydroisoquinoline-(3S)-carboxylate (0.58 g).

Ethyl 2-benzyl-7-[2-(5-ethyl-pyridin-2-yl)ethoxy]-1,2,3,4-tetrahydroisoquinoline-(3S)-carboxylate IR ν (nujol) $cm^{-1}$; 1732, 1612, 1504.
$^1$H-NMR ($CDCl_3$) δ (ppm);
1.22 (6H, t, J=7.2 Hz), 2.61 (2H, q, J=7.2 Hz), 3.07 (2H, d, J=5.5 Hz), 3.18 (2H, t, J=6.6 Hz), 3.72 (1H, t, J=5.5 Hz), 3.81 (1H, s), 3.90 (4H, s), 4.13 (2H, q, J=7.2 Hz), 4.27 (2H, t, J=6.6 Hz), 6.51 (1H, d, J=2.0 Hz), 6.69 (1H, dd, J=2.0, 8.4 Hz), 6.98 (1H, d, J=8.4 Hz), 7.10–7.50 (7H, m), 8.00–8.20 (1H, m).

(2) The compound (0.94 g) obtained in (1) above was dissolved in 40 ml of a mixed solution of tetrahydrofuran-methanol (3:1). Thereto was added 2N aqueous sodium hydroxide solution (6.0 ml), and the mixture was stirred at 40° C. for 2 hr. The solvent was evaporated under reduced pressure. Water (10 ml) and then sodium chloride were added to supersaturation, and the mixture was extracted three times with ethyl acetate (30 ml). The ethyl acetate layer was washed with saturated brine (10 ml) and dried over $Na_2SO_4$. Ethyl acetate was evaporated under reduced pressure. Diisopropyl ether was added to the obtained residue. The solid was collected by filtration to give the title compound (0.58 g).
IR ν (nujol) $cm^{-1}$; 1576, 1504.
$^1$H-NMR (MeOH-$d_4$) δ (ppm);
1.22 (6H, t, J=7.5 Hz), 2.63 (2H, q, J=7.5 Hz), 2.90–3.20 (4H, m), 3.72 (1H, s), 3.85 (1H, s), 3.95–4.35 (5H, m), 4.27 (2H, t, J=6.6 Hz), 6.40–6.75 (2H, m), 6.91 (1H, d, J=8.4 Hz), 7.20–7.65 (7H, m), 8.20–8.35 (1H, m).

Example 13

2-Benzyl-7-[2-(indolin-1-yl)ethoxy]-1,2,3,4-tetrahydroisoquinoline-(3S)-carboxylic acid (1) Ethyl 2-benzyl-7-hydroxy-1,2,3,4-tetrahydroisoquinoline-(3S)-carboxylate (1.0 g) was dissolved in N,N-dimethylformamide (10 ml). Thereto was added sodium hydride (154 mg, 60% suspension in oil) under ice-cooling and the mixture was stirred at the same temperature for 30 min. 1-(2-Bromoethyl)indoline (1.09 g) was added and the mixture was further stirred at room temperature for 2 hr. Ethyl acetate (100 ml) was added to the reaction mixture, and the mixture was washed with water (100 ml) and saturated brine (50 ml) and dried over $Na_2SO_4$. Ethyl acetate was evaporated under reduced pressure. The obtained residue was purified by silica gel column chromatography to give ethyl 2-benzyl-7-[2-

(indolin-1-yl)ethoxy]-1,2,3,4-tetrahydroisoquinoline-(3S)-carboxylate (1.18 g).

Ethyl 2-benzyl-7-[2-(indolin-1-yl)ethoxy]-1,2,3,4-tetrahydroisoquinoline-(3S)-carboxylate IR ν(neat) cm$^{-1}$; 2926, 2843, 1732, 1609, 1493.
$^1$H-NMR (CDCl$_3$) δ (ppm);
1.22 (3H, t, J=7.2 Hz), 2.95 (2H, t, J=8.3 Hz), 3.08 (2H, d, J=5.3 Hz), 3.20–3.60 (3H, m), 3.60–4.30 (10H, m), 6.40–6.80 (4H, m), 6.80–7.20 (3H, m), 7.20–7.50 (5H, m).
(2) The compound (1.17 g) obtained in (1) above was dissolved in 24 ml of a mixed solution of tetrahydrofuran-methanol (3:1). Thereto was added 1N aqueous lithium hydroxide solution (7.69 ml), and the mixture was stirred at 50° C. for 1 hr. The solvent was evaporated under reduced pressure, and the obtained residue was acidified with citric acid. The precipitated crystals were collected by filtration to give the title compound (0.93 g).
IR ν (nujol) cm$^{-1}$; 1634, 1609, 1491.
$^1$H-NMR (CDCl$_3$) δ (ppm);
2.95 (2H, br-t, J=8.2 Hz), 3.16 (2H, br-d, J=6.1 Hz), 3.25–3.60 (3H, m), 3.60–4.40 (8H, m), 4.07 (2H, s), 4.10 (2H, t, J=5.5 Hz), 4.13 (2H, q, J=7.2 Hz), 5.60–6.30 (1H, br), 6.30–6.85 (4H, m), 6.85–7.20 (3H, m), 7.32 (5H, s).

Example 14

Ethyl 2-benzyl-7-[2-(5-methyl-2-phenyloxazol-4-yl)ethoxy]-1,2,3,4-tetrahydroisoquinoline-(3S)-carboxylate Ethyl 2-benzyl-7-hydroxy-1,2,3,4-tetrahydroisoquinoline-(3S)-carboxylate (10.0 g) and 2-(5-methyl-2-phenyloxazol-4-yl)ethyl methanesulfonate (18.01 g) were dissolved in N,N-dimethylformamide (200 ml). Thereto was added potassium carbonate (13.3 g) and the mixture was stirred at 80° C. for 10 hr. Water (1 L) was added to the reaction mixture, and the mixture was extracted twice with ethyl acetate (200 ml). The ethyl acetate layer was washed with saturated brine (500 ml) and dried over Na$_2$SO$_4$. Ethyl acetate was evaporated under reduced pressure. The obtained residue was purified by silica gel column chromatography to give the title compound (7.06 g).

IR and NMR spectrum corresponded to those obtained in Example 2(1).

Example 15

Methyl 7-[2-(5-methyl-2-phenyloxazol-4-yl)ethoxy]-1,2,3,4-tetrahydroisoquinoline-(3S)-carboxylate (1) Methyl 2-tert-butoxycarbonyl-7-hydroxy-1,2,3,4-tetrahydroisoquinoline-(3S)-carboxylate (15.16 g) and 2-(5-methyl-2-phenyloxazol-4-yl)ethyl methanesulfonate (20.0 g) were dissolved in N,N-dimethylformamide (300 ml). Thereto was added potassium carbonate (19.7 g) and the mixture was stirred at 80° C. for 3.5 hr. Water (1 L) was added to the reaction mixture, and the mixture was extracted twice with ethyl acetate (300 ml). The ethyl acetate layer was washed with saturated brine (500 ml) and dried over Na$_2$SO$_4$. Ethyl acetate was evaporated under reduced pressure. The obtained residue was purified by silica gel column chromatography to give methyl 2-tert-butoxycarbonyl-7-[2-(5-methyl-2-phenyloxazol-4-yl)ethoxy]-1,2,3,4-tetrahydroisoquinoline-(3S)-carboxylate (14.0 g).

Methyl 2-tert-butoxycarbonyl-7-[2-(5-methyl-2-phenyloxazol-4-yl)ethoxy]-1,2,3,4-tetrahydroisoquinoline-(3S)-carboxylate $^1$H-NMR (CDCl$_3$) δ (ppm);
1.46, 1.50 (9H, s, s), 2.36 (3H, s), 2.95 (2H, t, J=6.8 Hz), 2.90–3.30 (2H, m), 3.60 (3H, s), 4.21 (2H, t, J=6.8 Hz), 4.50, 4.60 (2H, s, s), 4.70–4.90, 5.00–5.20 (1H, m, m), 6.60–6.90 (2H, m), 7.12 (1H, d, J=8.4 Hz), 7.30–7.55 (3H, m), 7.90–8.15 (2H, m).
(2) The compound (14.0 g) obtained in (1) above was dissolved in formic acid (42 ml). Thereto was added 8.78N hydrogen chloride solution (10.7 ml) in 2-propanol under ice-cooling, and the mixture was stirred at room temperature for 20 min. Ethyl acetate (300 ml) and water (500 ml) were added to the reaction mixture, and the mixture was neutralized with sodium hydrogencarbonate and the two layers were separated. The obtained ethyl acetate layer was washed with saturated brine (500 ml) and dried over Na$_2$SO$_4$. Ethyl acetate was evaporated under reduced pressure. The obtained residue was purified by silica gel column chromatography to give the title compound (9.4 g).
IR ν (nujol) cm$^{-1}$; 3560, 1744, 1643, 1612, 1578, 1553, 1504.
$^1$H-NMR (CDCl$_3$) δ (ppm);
1.92 (1H, s), 2.36 (3H, s), 2.80–3.20 (4H, m), 3.60–3.85 (1H, m), 3.76 (3H, s), 4.04 (2H, s), 4.21 (2H, t, J=6.6 Hz,), 6.57 (1H, d, J=2.0 Hz), 6.71 (1H, dd, J=2.0, 8.6 Hz), 7.00 (1H, d, J=8.6 Hz), 7.30–7.60 (3H, m), 7.85–8.15 (2H, m).

Example 16

2-(4-Methoxybenzyl)-7-[2-(5-methyl-2-phenyloxazol-4-yl)ethoxy]-1,2,3,4-tetrahydroisoquinoline-(3S)-carboxylic acid (1) The compound (800 mg) of Example 15 was dissolved in N,N-dimethylformamide (8 ml). Thereto was added sodium hydride (96 mg, 60% suspension in oil) under ice-cooling and the mixture was stirred at room temperature for 30 min. To the obtained mixture was dropwise added 4-methoxybenzyl chloride (0.41 ml), and the mixture was stirred further at 50° C. for 3 hr. Ethyl acetate (50 ml) was added to the reaction mixture, and the mixture was washed water (50 ml) and saturated brine (30 ml) and dried over Na$_2$SO$_4$. Ethyl acetate was evaporated under reduced pressure. The obtained residue was purified by silica gel column chromatography to give methyl 2-(4-methoxybenzyl)-7-[2-(5-methyl-2-phenyloxazol-4-yl)ethoxy]-1,2,3,4-tetrahydroisoquinoline-(3S)-carboxylate (0.82 g). Methyl 2-(4-methoxybenzyl)-7-[2-(5-methyl-2-phenyloxazol-4-yl)ethoxy]-1,2,3,4-tetrahydroisoquinoline-(3S)-carboxylate:
IR ν (nujol) cm$^{-1}$; 1736, 1638, 1614, 1553, 1514
$^1$H-NMR (CDCl$_3$) δ (ppm);
2.35 (3H, s), 2.93 (2H, t, J=6.6 Hz), 3.05 (2H, d, J=5.5 Hz), 3.66 (3H, s), 3.70–4.00 (8H, m), 4.17 (2H, t, J=6.6 Hz), 6,50 (1H, d, J=2.0 Hz), 6.68 (1H, dd, J=2.0, 8.6 Hz), 6.85 (2H, d, J=8.6 Hz), 6.98 (1H, d, J=8.6 Hz), 7.28 (2H, d, J=8.6 Hz), 7.30–7.50 (3H, m), 7.80–8.10 (2H, m).
(2) The compound (450 mg) obtained in (1) above was dissolved in 10 ml of a mixed solution of tetrahydrofuran-methanol (3:1). Thereto was added 2N aqueous lithium hydroxide solution (2.5 ml), and the mixture was stirred at room temperature for 3 hr. The solvent was evaporated under reduced pressure, and the obtained residue was acidified with citric acid. The precipitated crystals were collected by filtration to give the title compound (350 mg).

IR ν (nujol) cm$^{-1}$; 3288, 1612, 1555, 1514.
$^1$H-NMR (CDCl$_3$) δ (ppm);
2.35 (3H, s), 2.93 (2H, t, J=6.4 Hz), 3.18 (2H, d, J=6.8 Hz), 3.70–4.10 (5H, m), 3.77 (3H, s), 4.17 (2H, t, J=6.4 Hz), 4.50 (1H, br-s), 6.60 (1H, d, J=2.0 Hz), 6.65–6.95 (3H, m), 7.08 (2H, d, J=8.4 Hz), 7.20–7.60 (5H, m), 7.80–8.10 (2H, m).

Example 17

Ethyl 2-(4-methoxybenzyl)-7-[2-(5-methyl-2-phenyloxazol-4-yl)ethoxy]-1,2,3,4-tetrahydroisoquinoline-(3S)-carboxylate In the same manner as in Example 16(1), the title compound was obtained.
$^1$H-NMR (CDCl$_3$) δ (ppm);
1.21 (3H, t, J=7.0 Hz), 2.34 (3H, s), 2.91 (2H, t, J=7.0 Hz), 3.04 (2H, d, J=5.5 Hz), 3.60–3.95 (8H, m), 4.12 (2H, q, J=7.0 Hz), 4.15 (2H, t, J=7.0 Hz), 6.51 (1H, d, J=2.0 Hz), 6.67 (1H, dd, J=2.0, 8.8 Hz), 6.75–7.00 (3H, m), 7.15–7.50 (5H, m), 7.85–8.10 (2H, m).

Example 18

2-(4-Methylbenzyl)-7-[2-(5-methyl-2-phenyloxazol-4-yl)ethoxy]-1,2,3,4-tetrahydroisoquinoline-(3S)-carboxylic acid (1) The compound (800 mg) of Example 15 was dissolved in N,N-dimethylformamide (8.0 ml). Thereto was added sodium hydride (96 mg, 60% suspension in oil) under ice-cooling and the mixture was stirred at room temperature for 30 min. To the obtained mixture was dropwise added α-chloro-p-xylene (0.40 ml), and the mixture was stirred at 50° C. for 3 hr and further stirred at room temperature for 15 hr. Ethyl acetate (50 ml) was added to the reaction mixture, and the mixture was washed with water (50 ml) and saturated brine (30 ml) and dried over Na$_2$SO$_4$. Ethyl acetate was evaporated under reduced pressure. The obtained residue was purified by silica gel column chromatography to give methyl 2-(4-methylbenzyl)-7-[2-(5-methyl-2-phenyloxazol-4-yl)ethoxy]-1,2,3,4-tetrahydroisoquinoline-(3S)-carboxylate (0.90 g).

Methyl 2-(4-methylbenzyl)-7-[2-(5-methyl-2-phenyloxazol-4-yl)ethoxy]-1,2,3,4-tetrahydroisoquinoline-(3S)-carboxylate IR ν (nujol) cm$^{-1}$; 1736, 1639, 1614, 1595, 1551.
$^1$H-NMR (CDCl$_3$) δ (ppm);
2.34 (6H, s), 2.93 (2H, t, J=6.7 Hz), 3.06 (2H, d, J=5.0 Hz), 3.50–4.00 (5H, m), 3.65 (3H, s), 4.17 (2H, t, J=6.7 Hz), 6.51 (1H, d, J=2.0 Hz), 6.68 (1H, dd, J=2.0, 8.6 Hz), 6.98 (2H, d, J=8.6 Hz), 7.11 (2H, d, J=8.4 Hz), 7.26 (2H, d, J=8.4 Hz), 7.30–7.55 (3H, m), 7.80–8.15 (2H, m).

(2) The compound (608 mg) obtained in (1) above was dissolved in 17 ml of a mixed solution of tetrahydrofuran-methanol (3:1). Thereto was added 1N aqueous lithium hydroxide solution (6.1 ml), and the mixture was stirred at room temperature for 3 hr. The solvent was evaporated under reduced pressure, and the obtained residue was acidified with citric acid. The precipitated crystals were collected by filtration to give the title compound (400 mg).
IR ν (nujol) cm$^{-1}$; 1620, 1555, 1506.
$^1$H-NMR (CDCl$_3$) δ (ppm);
2.32 (3H, s), 2.35 (3H, s), 2.93 (2H, t, J=7.0 Hz), 3.17 (2H, d, J=6.6 Hz), 3.65–4.05 (5H, m), 4.17 (2H, t, J=7.0 Hz), 4.73 (1H, br-s), 6.60 (1H, d, J=2.0 Hz), 6.77 (1H, dd, J=2.0, 8.8 Hz), 6.95–7.60 (8H, m), 7.85–8.10 (2H, m).

Example 19

Ethyl 2-(4-methylbenzyl)-7-[2-(5-methyl-2-phenyloxazol-4-yl)ethoxy]-1,2,3,4-tetrahydroisoquinoline-(3S)-carboxylate In the same manner as in Example 18(1), the title compound was obtained.
$^1$H-NMR (CDCl$_3$) δ (ppm);
1.21 (3H, t, J=7.0 Hz), 2.34 (3H, s), 2.92 (2H, t, J=7.0 Hz), 3.05 (2H, d, J=5.4 Hz), 3.71 (1H, t, J=5.4 Hz), 3.80 (1H, s), 3.92 (1H, s), 4.12 (2H, q, J=7.0 Hz), 4.16 (2H, t, J=7.0 Hz), 6.51 (1H, d, J=2.0 Hz), 6.68 (1H, dd, J=2.0, 8.4 Hz), 6.98 (1H, d, J=8.4 Hz), 7.00–7.60 (7H, m), 7.80–8.10 (2H, m).

Example 20

2-Benzyl-7-[2-(6-carboxyindolin-1-yl)ethoxy]-1,2,3,4-tetrahydroisoquinoline-(3S)-carboxylic acid (1) Ethyl 2-benzyl-7-hydroxy-1,2,3,4-tetrahydroisoquinoline-(3S)-carboxylate (1.0 g) was dissolved in N,N-dimethylformamide (10 ml). Thereto was added sodium hydride (154 mg, 60% suspension in oil) under ice-cooling and the mixture was stirred at the same temperature for 30 min. To the obtained mixture was added 1-(2-bromoethyl)-6-methoxycarbonylindoline (1.36 g), and the mixture was stirred further at room temperature for 4 hr. Ethyl acetate (100 ml) was added to the reaction mixture, and the mixture was washed water (100 ml) and saturated brine (50 ml) and dried over Na$_2$SO$_4$. Ethyl acetate was evaporated under reduced pressure. The obtained residue was purified by silica gel column chromatography to give ethyl 2-benzyl-7-[2-(6-methoxycarbonylindolin-1-yl)ethoxy]-1,2,3,4-tetrahydroisoquinoline-(3S)-carboxylate (1.18 g).

Ethyl 2-benzyl-7-[2-(6-methoxycarbonylindolin-1-yl)ethoxy]-1,2,3,4-tetrahydroisoquinoline-(3S)-carboxylate IR ν(neat) cm$^{-1}$; 2949, 2841, 1717, 1611, 1587, 1497.
$^1$H-NMR (CDCl$_3$) δ (ppm);
1.23 (3H, t, J=7.2 Hz), 2.99 (2H, t, J=8.8 Hz), 3.00–3.25 (2H, m), 3.35–4.35 (13H, m), 3.87 (3H, s), 6.52 (1H, d, J=2.4 Hz), 6.70 (1H, dd, J=2.4, 8.3 Hz), 6.90–7.20 (3H, m), 7.20–7.55 (6H, m).

(2) The compound (1.31 g) obtained in (1) above was dissolved in 33 ml of a mixed solution of tetrahydrofuran-methanol (3:1). Thereto was added 1N aqueous lithium hydroxide solution (15.3 ml), and the mixture was stirred at 50° C. for 2 hr. The solvent was evaporated under reduced pressure, and the obtained residue was acidified with citric acid. The precipitated crystals were collected by filtration to give the title compound (1.0 g).
IR ν (nujol) cm$^{-1}$; 3400, 1693, 1612, 1497.
$^1$H-NMR (MeOH-d$_4$) δ (ppm);
2.96 (2H, br-t, J=8.0 Hz), 3.15–3.75 (3H, m), 3.80–4.50 (10H, m), 6.65–7.70 (11H, m).

Example 21

2-(4-Fluorobenzyl)-7-[2-(5-methyl-2-phenyloxazol-4-yl)ethoxy]-1,2,3,4-tetrahydroisoquinoline-(3S)-carboxylic acid (1) The compound (1.00 g) obtained in Example 15 was dissolved in N,N-dimethylformamide (20 ml). Thereto were added 4-fluorobenzyl chloride (0.46 ml), potassium carbonate (0.53 g) and potassium iodide (0.21 g), and the mixture was stirred at 50° C. for 1.5 hr. Ethyl acetate (50 ml) was added to the reaction mixture, and the mixture was washed with water (100 ml) and saturated brine (100 ml) and dried over $Na_2SO_4$. Ethyl acetate was evaporated under reduced pressure. The obtained residue was purified by silica gel column chromatography to give methyl 2-(4-fluorobenzyl)-7-[2-(5-methyl-2-phenyloxazol-4-yl)ethoxy]-1,2,3,4-tetrahydroisoquinoline-(3S)-carboxylate (0.92 g).

Methyl 2-(4-fluorobenzyl)-7-[2-(5-methyl-2-phenyloxazol-4-yl)ethoxy]-1,2,3,4-tetrahydroisoquinoline-(3S)-carboxylate IR ν (nujol) $cm^{-1}$; 1738, 1639, 1616, 1551, 1510
$^1$H-NMR (CDCl$_3$) δ (ppm);
2.35 (3H, s), 2.93 (2H, t, J=6.8 Hz), 3.07 (2H, d, J=5.0 Hz), 3.55–4.00 (5H, m), 3.65 (3H, s), 4.18 (2H, t, J=6.8 Hz), 6.51 (1H, d, J=2.0 Hz), 6.70 (1H, dd, J=2.0, 8.6 Hz), 6.80–7.15 (3H, m), 7.15–7.50 (5H, m), 7.80–8.15 (2H, m).

(2) The compound (900 mg) of (1) above was dissolved in 18 ml of a mixed solution of tetrahydrofuran-methanol (3:1). Thereto was added 1N aqueous lithium hydroxide solution (8.9 ml), and the mixture was stirred at room temperature for 3 hr. The solvent was evaporated under reduced pressure, and the obtained residue was acidified with citric acid. The precipitated crystals were collected by filtration to give the title compound (0.68 g).

IR ν (nujol) $cm^{-1}$; 3398, 1614, 1555, 1510.
$^1$H-NMR (CDCl$_3$) δ (ppm);
2.36 (3H, s), 2.94 (2H, t, J=6.4 Hz), 3.15 (2H, d, J=6.4 Hz), 3.45–4.00 (5H, m), 4.19 (2H, t, J=6.4 Hz), 6.60 (1H, d, J=2.0 Hz), 6.75 (1H, dd, J=2.0, 8.6 Hz), 6.90–7.55 (8H, m), 7.90–8.10 (2H, m).

Example 22

2-(2,2-Dimethylpropionyl)-7-[2-(5-methyl-2-phenyloxazol-4-yl)ethoxy]-1,2,3,4-tetrahydroisoquinoline-(3S)-carboxylic acid Methyl 7-[2-(5-methyl-2-phenyloxazol-4-yl)ethoxy]-1,2,3,4-tetrahydroisoquinoline-(3S)-carboxylate (0.60 g) was dissolved in methylene chloride (6 ml). Thereto were added pivaloyl chloride (0.22 ml) and triethylamine (0.32 ml) under ice-cooling, and the mixture was stirred at the same temperature for 15 min. Ethyl acetate (100 ml) was added to the reaction mixture, and the mixture was washed successively with 10% aqueous citric acid solution (50 ml), saturated aqueous sodium hydrogencarbonate solution (50 ml) and saturated brine (50 ml) and dried over $Na_2SO_4$. The solvent was evaporated under reduced pressure. The obtained residue was dissolved in 18 ml of a mixed solution of tetrahydrofuran-methanol (3:1). Thereto was added 1N aqueous lithium hydroxide solution (4.6 ml), and the mixture was stirred at 50° C. for 30 min. The solvent was evaporated under reduced pressure. Thereto was added water (20 ml) and the mixture was acidified with citric acid. The obtained mixture was extracted with ethyl acetate (50 ml). The ethyl acetate layer was washed with saturated brine (30 ml) was dried over $Na_2SO_4$. Ethyl acetate was evaporated under reduced pressure to give the title compound (0.65 g).

IR ν (nujol) $cm^{-1}$; 1734, 1630, 1612, 1553.
$^1$H-NMR (DMSO-d$_6$) δ (ppm);
1.24 (9H, s), 2.36 (3H, s), 2.80–4.00 (1H, br), 2.92 (2H, t, J=6.4 Hz), 2.95–3.15 (2H, m), 4.18 (2H, t, J=6.4 Hz), 4.41, 4.91 (2H, ABq, J=18.1 Hz), 4.90–5.15 (1H, m), 6.77 (1H, dd, J=2.0, 8.1 Hz), 6.89 (1H, d, J=2.0 Hz), 7.09 (1H, d, J=8.1 Hz), 7.30–7.65 (3H, m), 7.80–8.10 (2H, m).

Example 23

2-(2,2-Dimethylpropyl)-7-[2-(5-methyl-2-phenyloxazol-4-yl)ethoxy]-1,2,3,4-tetrahydroisoquinoline-(3S.)-carboxylic acid The title compound (1.66 g) of Example 22 was dissolved in pyridine (16.6 ml). Thereto was added sodium borohydride (1.36 g) and the mixture was stirred at 100° C. for 4 hr. The mixture was acidified with 10% aqueous citric acid solution and extracted with ethyl acetate (100 ml). The ethyl acetate layer was washed successively by adding 10% aqueous citric acid solution (100 ml) and saturated brine (50 ml) and dried over $Na_2SO_4$. Ethyl acetate was evaporated under reduced pressure. The obtained residue was purified by silica gel column chromatography to give the title compound (0.84 g).

IR ν (nujol) $cm^{-1}$; 3391, 3279, 1668, 1645, 1616, 1597, 1497.
$^1$H-NMR (CDCl$_3$) δ (ppm);
0.96 (9H, s), 2.35 (3H, s), 2.46, 2.73 (2H, ABq, J=13.9 Hz), 2.93 (2H, t, J=6.7 Hz), 3.03–3.23 (2H, m), 3.57–3.78 (1H, m), 3.91, 4.18 (1H, ABq, J=15.4 Hz), 4.17 (2H, t, J=6.7 Hz), 5.60–6.05 (1H, br), 6.60 (1H, d, J=2.0 Hz), 6.73 (1H, dd, J=2.0, 8.4 Hz), 7.04 (1H, d, J=8.4 Hz), 7.30–7.55 (3H, m), 7.80–8.10 (2H, m).

Example 24

2-(2,2-Dimethylpropyl)-7-[2-(5-methyl-2-phenyloxazol-4-yl)ethoxy]-1,2,3,4-tetrahydroisoquinoline-(3S)-carboxylic acid (1) Methyl 2-(2,2-dimethylpropyl)-7-[2-(5-methyl-2-phenyloxazol-4-yl)ethoxy]-1,2,3,4-tetrahydroisoquinoline-(3S)-carboxylate Methyl 2-(2,2-dimethylpropyl)-7-hydroxy-1,2,3,4-tetrahydroisoquinoline-(3S)-carboxylate (1.5 g) and 2-(5-methyl-2-phenyloxazol-4-yl)ethyl methanesulfonate (2.59 g) were dissolved in toluene (45 ml). Thereto were added potassium carbonate (2.24 g) and tetraethylammomium fluoride (0.60 g) and the mixture was stirred at 80° C. for 3 hr. The reaction mixture was washed successively with water (50 ml) and saturated brine (50 ml) and dried over $Na_2SO_4$. Toluene was evaporated under reduced pressure. The obtained residue was purified by silica gel column chromatography to give methyl 2-(2,2-dimethylpropyl)-7-[2-(5-methyl-2-phenyloxazol-4-yl)ethoxy]-1,2,3,4-tetrahydroisoquinoline-(3S)-carboxylate (2.77 g).

1H-NMR (CDCl$_3$) δ (ppm);
0.88 (9H, s), 2.35, 2.58 (2H, ABq, J=14.5 Hz), 2.36 (3H, s), 2.46 (2H, t, J=6.8 Hz), 2.95–3.20 (2H, m), 3.60 (3H, s), 3.60–3.80 (1H, m), 3.85–4.20 (2H, m), 4.19 (2H, t, J=6.8 Hz), 6.54 (1H, d, J=2.0 Hz), 6.68 (1H, dd, J=2.0, 8.4 Hz), 6.98 (1H, d, J=8.4 Hz), 7.30–7.50 (3H, m), 7.85–8.05 (2H, m).

(2) The compound (5.0 g) of (1) above was dissolved in 130 ml of a mixed solution of tetrahydrofuran-methanol (3:1). Thereto was added 1N aqueous lithium hydroxide solution (54 ml), and the mixture was stirred at 50° C. for 3.5 hr and acidified with 6N hydrochloric acid. The solvent was evaporated under reduced pressure. The obtained residue was extracted with ethyl acetate (200 ml). The ethyl acetate layer was washed with saturated brine (100 ml) and dried over Na$_2$SO$_4$. Ethyl acetate was evaporated under reduced pressure. The obtained residue was dissolved in ethanol (25 ml). Thereto was added water (150 ml) and the mixture was stirred at room temperature to allow crystallization. The precipitated crystals were collected by filtration to give the title compound (4.52 g).

IR and $^1$H-NMR NMR spectrum are correspondent to that obtained in Example 23.

Example 25

2-Benzyl-7-[2-(5-methyl-2-phenyloxazol-4-yl) ethoxy]-1,2,3,4-tetrahydroisoquinoline-(3S)-carboxylic acid hydrochloride The title compound (675 mg) of Example 2 was dissolved in 75% ethanol (10.1 ml) under heating. Thereto was added 6N hydrochloric acid (2.23 ml), and the mixture was stood at room temperature for 2 hr to allow crystallization. The precipitated crystals were collected by filtration to give the title compound (625 mg).

IR ν (nujol) cm$^{-1}$; 3398, 1734, 1680, 1641, 1620, 1587, 1574, 1551.

$^1$H-NMR (DMSO-d$_6$) δ (ppm);

2.36 (3H, s), 2.92 (2H, t, J=6.0 Hz), 3.00–3.70 (2H, m), 4.19 (2H, t, J=6.0 Hz), 4.25–4.75 (5H, m), 4.80–6.70 (2H, br), 6.70–7.05 (2H, m), 7.20 (1H, d, J=8.6 Hz), 7.30–7.77 (8H, m), 7.80–8.10 (2H, m).

Example 26

Sodium 2-benzyl-7-[2-(5-methyl-2-phenyloxazol-4-yl)ethoxy]-1,2,3,4-tetrahydroisoquinoline-(3S)-carboxylate The title compound (1.0 g) of Example 2 was suspended in methanol (10 ml). Thereto was added a 2.09N sodium hydroxide solution (1.02 ml) in methanol. After dissolution, methanol was evaporated under reduced pressure. Diethyl ether was added to the obtained residue, and the precipitated crystals were collected by filtration to give the title compound (1.03 g)

IR ν (nujol) cm$^{-1}$; 1638, 1589, 1503.

$^1$H-NMR (DMSO-d$_6$) δ (ppm);

2.33 (3H, s), 2.55–3.60 (6H, m), 3.60–4.30 (5H, m), 6.47 (1H, s), 6.60 (1H, d, J=8.6 Hz), 6.92 (1H, d, J=8.6 Hz), 7.00–7.67 (8H, m), 7.67–8.05 (2H, m).

Example 27

2-(2,2-Dimethylpropyl)-7-[2-(5-methyl-2-phenyloxazol-4-yl)ethoxy]-1,2,3,4-tetrahydroisoquinoline-(3S)-carboxylic acid hydrochloride The title compound (2.1 g) of Example 23 was dissolved in methanol (10.5 ml). 8.78N Hydrogen chloride solution (1.07 ml) in isopropanol and then ethyl acetate (50 ml) were added to the mixture and the mixture was stirred at room temperature for crystallization. The precipitated crystals were collected by filtration to give the title compound (1.03 g).

IR ν (nujol) cm$^{-1}$; 3362, 3206, 1740, 1672, 1612, 1576, 1553.

$^1$H-NMR (DMSO-d$_6$) δ (ppm);

1.12 (9H, s), 2.37 (3H, s), 2.65–3.50 (6H, m), 4.21 (2H, t, J=6.5 Hz), 4.40–4.80 (3H, m), 4.85–6.50 (2H, br), 6.90 (1H, d, J=8.1 Hz), 6.94 (1H, s), 7.21 (1H, d, J=8.1 Hz), 7.35–7.65 (3H, m), 7.80–8.05 (2H, m).

Example 28

2-(2,2-Dimethylpropyl)-7-[2-(5-methyl-2-phenyloxazol-4-yl)ethoxy]-1,2,3,4-tetrahydroisoquinoline-(3S)-carboxylic acid sulfate The title compound (0.5 g) of Example 23 was dissolved in methanol (1.25 ml). Sulfuric acid (0.3 ml) and then water (16.8 ml) were added to the mixture and the mixture was stirred at room temperature for crystallization. The precipitated crystals were collected by filtration to give the title compound (0.25 g).

IR ν (nujol) cm$^{-1}$; 3400, 1715, 1650, 1615, 1550.

$^1$H-NMR (DMSO-d$_6$) δ (ppm);

0.93 (9H, s), 2.36 (3H, s), 2.40–3.30 (6H, m), 3.75–4.45 (5H, m), 4.60–6.50 (2H, br), 6.70 (1H, br-s), 6.74 (1H, d, J=8.1 Hz), 7.06 (1H, d, J=8.1 Hz), 7.25–7.65 (3H, m), 7.75–8.10 (2H, m).

Example 29

2-(2,2-Dimethylpropyl)-7-[2-(5-methyl-2-phenyloxazol-4-yl)ethoxy]-1,2,3,4-tetrahydroisoquinoline-(3S)-carboxylic acid tosylate The title compound (0.5 g) of Example 23 and p-toluenesulfonic acid (0.28 g) were dissolved in ethanol (10 ml) under heating. After crystallization at room temperature under stirring, the precipitated crystals were collected by filtration to give the title compound (0.3 g).

IR ν (nujol) cm$^{-1}$; 3047, 1734, 1645, 1612, 1514.

$^1$H-NMR (DMSO-d$_6$) δ (ppm);

1.07 (9H, s), 2.28 (3H, s), 2.36 (3H, s), 2.70–3.50 (6H, m), 4.21 (2H, t, J=6.5 Hz), 4.40–4.80 (3H, m), 6.80–7.35 (5H, m), 7.35–7.65 (5H; m), 7.75–8.05 (2H, m), 8.40–12.00 (2H, br).

Example 30

2-(2,2-Dimethylpropyl)-7-[2-(5-methyl-2-phenyloxazol-4-yl)ethoxy]-1,2,3,4-tetrahydroisoquinoline-(3S)-carboxylic acid fumarate The title compound (1.0 g) of Example 23 and fumaric acid (0.23 g) were dissolved in methanol (5 ml). Water (5 ml) was added to the mixture and the mixture was stirred at room temperature for crystallization. The precipitated crystals were collected by filtration to give the title compound (0.94 g).

IR ν (nujol) cm$^{-1}$; 3500, 3395, 1680, 1650, 1625, 1575, 1550.

$^1$H-NMR (DMSO-d$_6$) δ (ppm);

0.85 (9H, s), 2.00–6.30 (2H, br), 2.35 (3H, s), 2.32, 2.59 (2H, ABq, J=14.9 Hz), 2.75–3.10 (2H, m), 2.85 (2H, t, J=6.6 Hz), 3.45–4.30 (3H, m), 4.15 (2H, t, J=6.6 Hz), 6.61 (1H, d, J=2.2 Hz), 6.64 (1H, s), 6.66 (1H, dd, J=2.2, 8.4 Hz), 7.00 (1H, d, J=8.4 Hz), 7.35–7.65 (3H, m), 7.75–8.10 (2H, m).

Example 31

Calcium 2-(2,2-dimethylpropyl)-7-[2-(5-methyl-2-phenyloxazol-4-yl)ethoxy]-1,2,3,4-tetrahydroisoquinoline-(3S)-carboxylate The title compound (0.9 g) of Example 23 was dissolved in ethanol (9 ml). 0.04N Aqueous calcium hydroxide solution (54 ml) was added to the mixture and the mixture was stirred at room temperature for crystallization. The precipitated crystals were collected by filtration to give the title compound (0.79 g).

IR ν (nujol) cm$^{-1}$; 3396, 1638, 1611, 1556, 1504.
$^1$H-NMR (MeOH-d$_4$) δ (ppm);
0.87 (9H, s), 2.34 (3H, s), 2.36, 2.58 (2H, ABq, J=14.0 Hz), 2.80–3.10 (2H, m), 2.90 (2H, t, J=6.5 Hz), 3.30–3.80 (3H, m), 4.15 (2H, t, J=6.5 Hz), 6.50 (1H, d, J=2.4 Hz), 6.60 (1H, dd, J=2.4, 8.2 Hz), 6.90 (1H, d, J=8.2 Hz), 7.30–7.60 (3H, m), 7.80–8.05 (2H, m).

The following compounds were synthesized in the same manner as in Examples 1–24.

Example 32

2-Benzyl-7-[2-(5-methyl-2-tert-butyloxazol-4-yl) ethoxy]-1,2,3,4-tetrahydroisoquinoline-(3S)-carboxylic acid IR ν (nujol) cm$^{-1}$; 3458, 1682, 1618, 1587, 1510.
$^1$H-NMR (DMSO-d$_6$) δ (ppm);
1.32 (9H, s), 2.23 (3H, s), 2.83 (2H, t, J=6.6 Hz), 3.18 (2H, d, J=5.9 Hz), 3.65–4.40 (7H, m), 5.60 (1H, br-s), 6.56 (1H, br-s), 6.73 (1H, br-d), 7.06 (1H, d, J=8.4 Hz), 7.20–7.55 (5H, m).

Example 33

2-Benzyl-7-[2-(5-methyl-2-(thiophen-2-yl)oxazol-4-yl)ethoxy]-1,2,3,4-tetrahydroisoquinoline-(3S)-carboxylic acid IR ν (nujol) cm$^{-1}$; 3423, 1616, 1578, 1510.
$^1$H-NMR (DMSO-d$_6$) δ (ppm);
2.31 (3H, s), 2.70–3.10 (4H, m), 3.40–4.00 (4H, m), 3.39 (2H, s), 4.11 (2H, d, J=6.2 Hz), 6.59 (1H, br-s), 6.67 (1H, d, J=8.4 Hz), 7.01 (1H, d, J=8.4 Hz), 7.05–7.80 (3H, m), 7.32 (5H, s).

Example 34

2-Benzyl-7-[2-(5-methyl-2-isopropyloxazol-4-yl) ethoxy]-1,2,3,4-tetrahydroisoquinoline-(3S)-carboxylic acid IR ν (nujol) cm$^{-1}$; 3456, 1684, 1614, 1576, 1510.
$^1$H-NMR (DMSO-d$_6$) δ (ppm);
1.21 (6H, m), 2.19 (3H, s), 2.70–3.10 (5H, m), 3.50–4.20 (5H, m), 6.40–6.85 (2H, m), 7.01 (1H, d, J=8.1 Hz), 7.34 (5H, br-s).

Example 35

2-Butyl-7-[2-(5-methyl-2-phenyloxazol-4-yl) ethoxy]-1,2,3,4-tetrahydroisoquinoline-(3S)-carboxylic acid IR ν (nujol) cm$^{-1}$; 3382, 1722, 1614, 1554, 1506.
$^1$H-NMR (CDCl$_3$) δ (ppm);
0.88 (3H, t, J=6.6 Hz), 1.10–1.95 (4H, m), 2.36 (3H, s), 2.75–3.40 (6H, m), 3.71 (2H, br-t), 3.95–4.25 (4H, m), 6.57–7.57 (6H, m), 7.80–8.10 (3H, m).

Example 36

2-Benzyl-7-{2-[5-methyl-2-(2-methylpropenyl) oxazol-4-yl]ethoxy}-1,2,3,4-tetrahydroisoquinoline-(3S)-carboxylic acid IR ν (nujol) cm$^{-1}$; 3443, 3300, 1695, 1655, 1622, 1543, 1508.
$^1$H-NMR (DMSO-d$_6$) δ (ppm);
1.89 (3H, s), 2.11 (3H, s), 2.27 (3H, s), 2.79 (2H, t, J=6.1 Hz), 2.90–3.20 (2H, m), 3.50–4.00 (4H, m), 3.93 (2H, s), 4.07 (2H, t, J=6.1 Hz), 5.99 (1H, s), 6.58 (1H, s), 6.67 (1H, d, J=8.2 Hz), 6.72 (1H, d, J=8.2 Hz), 7.33 (5H, s).

Example 37

2-Benzyl-7-{2-[2-(3-butenyl)-5-methyloxazol-4-yl] ethoxy}-1,2,3,4-tetrahydroisoquinoline-(3S)-carboxylic acid IR ν (nujol) cm$^{-1}$; 3442, 1688, 1614, 1578, 1508.
$^1$H-NMR (CDCl$_3$) δ (ppm);
2.23 (3H, s), 2.49 (2H, t, J=6.2 Hz), 2.65–2.90 (4H, m), 3.05–3.30 (2H, m), 3.75–4.50 (8H, m), 4.90–5.20 (2H, m), 5.65–6.10 (1H, m), 6.58 (1H, d, J=1.7 Hz), 6.75 (1H, dd, J=1.7, 8.2 Hz), 7.07 (1H, d, J=8.2 Hz), 7.35 (5H, s).

Example 38

2-Allyl-7-[2-(5-methyl-2-phenyloxazol-4-yl) ethoxy]-1,2,3,4-tetrahydroisoquinoline-(3S)-carboxylic acid IR ν (nujol) cm$^{-1}$; 3335, 1690, 1618, 1553, 1506.
$^1$H-NMR (DMSO-d$_6$) δ (ppm);
2.35 (3H, s), 2.70–3.15 (4H, m), 3.38 (2H, d, J=6.2 Hz), 3.55–4.00 (3H, m), 4.16 (2H, t, J=6.6 Hz), 4.40–5.50 (1H, br), 5.00–5.40 (2H, m), 5.60–6.10 (1H, m), 6.65 (1H, s), 6.69 (1H, d, J=8.1 Hz), 7.01 (1H, d, J=8.1 Hz), 7.35–7.65 (3H, m), 7.75–8.10 (2H, m).

Example 39

7-[2-(5-Methyl-2-phenyloxazol-4-yl)ethoxy]-2-(2-propynyl)-1,2,3,4-tetrahydroisoquinoline-(3S)-carboxylic acid IR ν (nujol) cm$^{-1}$; 3383, 3306, 3221, 1692, 1622, 1508.
$^1$H-NMR (DMSO-d$_6$) δ (ppm);
2.00–6.40 (1H, br), 2.35 (3H, s), 2.70–3.10 (4H, m), 3.10–3.25 (1H, m), 3.50–4.00 (5H, m), 4.17 (2H, t, J=6.4 Hz), 6.66 (1H, s), 6.70 (1H, d, J=8.6 Hz), 7.01 (1H, d, J=8.6 Hz), 7.30–7.70 (3H, m), 7.85–8.05 (2H, m).

Example 40

2-(2-Butenyl)-7-[2-(5-methyl-2-phenyloxazol-4-yl) ethoxy]-1,2,3,4-tetrahydroisoquinoline-(3S)-carboxylic acid IR ν (nujol) cm$^{-1}$; 3447, 3342, 1684, 1620, 1556.
$^1$H-NMR (DMSO-d$_6$) δ (ppm);
1.67 (3H, d, J=4.9 Hz), 2.35 (3H, s), 2.70–3.10 (4H, m), 3.20–3.50 (2H, m), 3.50–4.00 (3H, m), 4.16 (2H, t, J=6.4 Hz), 4.35–5.20 (1H, br), 5.25–5.90 (2H, m), 6.55–6.90 (2H, m), 7.01 (2H, d, J=8.1 Hz), 7.35–7.70 (3H, m), 7.75–8.10 (2H, m).

Example 41

2-Benzyl-7-[(indolin-3-yl)ethoxy]-1,2,3,4-tetrahydroisoquinoline-(3S)-carboxylic acid IR ν (nujol) cm$^{-1}$; 1611, 1506.
$^1$H-NMR (DMSO-d$_6$) δ (ppm);
1.60–2.30 (2H, m), 2.80–4.20 (10H, m), 3.91 (2H, s), 4.20–6.00 (1H, br), 6.25–7.10 (7H, m), 7.33 (5H, s).

Example 42

2-(3-Butenyl)-7-[2-(5-methyl-2-phenyloxazol-4-yl)ethoxy]-1,2,3,4-tetrahydroisoquinoline-(3S)-carboxylic acid IR ν (nujol) cm$^{-1}$; 3425, 1682, 1612, 1555.
$^1$H-NMR (DMSO-d$_6$) δ (ppm);
2.10–2.40 (2H, m), 2.35 (3H, s), 2.60–3.15 (6H, m), 3.50–4.00 (3H, m), 4.17 (2H, t, J=6.3 Hz), 4.40–5.40 (1H, br), 4.85–5.25 (2H, m), 5.55–6.10 (1H, m), 6.50–6.85 (2H, m), 7.01 (1H, d, J=8.1 Hz), 7.35–7.70 (3H, m), 7.75–8.05 (2H, m).

Example 43

7-[2-(5-Methyl-2-phenyloxazol-4-yl)ethoxy]-2-pentanoyl-1,2,3,4-tetrahydroisoquinoline-(3S)-carboxylic acid IR ν (nujol) cm$^{-1}$; 1742, 1639, 1611, 1572, 1506.
$^1$H-NMR (DMSO-d$_6$) δ (ppm);
0.88 (3H, br-t), 1.05–1.75 (4H, m), 2.15–2.70 (2H, m), 2.35 (3H, s), 2.70–3.30 (4H, m), 4.18 (2H, br-t), 4.30–4.90 (2H, m), 4.90–5.25 (1H, m), 6.60–6.95 (2H, m), 7.08 (1H, d, J=7.9 Hz), 7.35–7.70 (3H, m), 7.75–8.10 (2H, m), 11.00–13.00 (1H, br).

Example 44

7-[2-(5-Methyl-2-phenyloxazol-4-yl)ethoxy]-2-(4-pentenoyl)-1,2,3,4-tetrahydroisoquinoline-(3S)-carboxylic acid IR ν (nujol) cm$^{-1}$; 1742, 1641, 1611, 1570.
$^1$H-NMR (DMSO-d$_6$) δ (ppm);
2.15–2.70 (2H, m), 2.35 (3H, s), 2.70–3.30 (4H, m), 4.18 (2H, br-t), 4.37–5.50 (5H, m), 5.60–6.15 (1H, m), 6.60–6.95 (2H, m), 7.09 (1H, d, J=7.7 Hz), 7.30–7.75 (3H, m), 7.75–8.15 (2H, m), 11.00–13.00 (1H, br).

Example 45

2-(3-Methyl-2-butenoyl)-7-[2-(5-methyl-2-phenyloxazol-4-yl)ethoxy]-1,2,3,4-tetrahydroisoquinoline-(3S)-carboxylic acid IR ν (nujol) cm$^{-1}$; 1738, 1641, 1611, 1555.
$^1$H-NMR (DMSO-d$_6$) δ (ppm);
1.87 (6H, s), 2.35 (3H, s), 2.70–3.30 (4H, m), 4.18 (2H, br-t), 4.49 (1H, d, J=18.0 Hz), 4.76 (1H, d, J=18.0 Hz), 4.95–5.22 (1H, m), 5.75–6.10 (1H, m), 6.50–6.90 (2H, m), 7.08 (1H, d, J=7.5 Hz), 7.20–7.60 (3H, m), 7.60–8.05 (2H, m), 11.00–13.00 (1H, br).

Example 46

2-(3,3-Dimethylbutyryl)-7-[2-(5-methyl-2-phenyloxazol-4-yl)ethoxy]-1,2,3,4-tetrahydroisoquinoline-(3S)-carboxylic acid IR ν (nujol) cm$^{-1}$; 1738, 1639, 1611, 1583, 1555.
$^1$H-NMR (DMSO-d$_6$) δ (ppm);
1.02 (9H, s), 2.36 (5H, s), 2.73–3.20 (4H, m), 4.17 (2H, t, J=7.0 Hz), 4.50 (1H, d, J=9.0 Hz), 4.83 (1H, d, J=9.0 Hz), 5.12 (1H, t, J=6.0 Hz), 6.60–6.95 (2H, m), 7.10 (1H, d, J=7.0 Hz), 7.35–7.65 (3H, m), 7.80–8.05 (2H, m), 11.00–13.00 (1H, br).

Example 47

2-Benzyl-7-methoxy-6-[2-(5-methyl-2-phenyloxazol-4-yl)ethoxy]-1,2,3,4-tetrahydroisoquinoline-(3RS)-carboxylic acid IR ν (nujol) cm$^{-1}$; 1722, 1628, 1553, 1520.
$^1$H-NMR (DMSO-d$_6$) δ (ppm);
2.36 (3H, s), 3.00 (2H, t, J=6.8 Hz), 3.10–3.35 (2H, m), 3.80–4.10 (3H, m), 3.75 (3H, s), 4.23 (2H, t, J=6.8 Hz), 5.80–6.20 (1H, br), 6.50, 6.72 (2H, s, s), 7.20–7.60 (8H, m), 7.80–8.10 (2H, m).

Example 48

Sodium 7-[2-(5-methyl-2-phenyloxazol-4-yl)ethoxy]-2-(pyridin-2-ylmethyl)-1,2,3,4-tetrahydroisoquinoline-(3S)-carboxylate IR ν (nujol) cm$^{-1}$; 1609, 1575, 1554, 1502.
$^1$H-NMR (CDCl$_3$) δ (ppm);
2.32 (3H, s), 2.60–3.20 (4H, m), 3.20–3.90 (5H, m), 4.08 (2H, br-t, J=6.5 Hz), 6.15–6.40 (1H, m), 6.40–6.70 (1H, m), 7.75–8.20 (3H, m), 7.20–7.65 (4H, m), 7.75–8.10 (2H, m), 8.25–8.60 (1H, m).

Example 49

2-Benzyl-7-(3-methyl-3-phenylbutoxy)-1,2,3,4-tetrahydroisoquinoline-(3S)-carboxylic acid IR ν (nujol) cm$^{-1}$; 1612, 1506.
$^1$H-NMR (DMSO-d$_6$) δ (ppm);
1.32 (6H, s), 2.02 (2H, t, J=7.5 Hz), 2.80–3.10 (2H, m), 3.40–4.00 (5H, m), 3.88 (2H, s), 4.10–6.00 (1H, br), 6.36 (1H, d, J=2.0 Hz), 6.53 (1H, dd, J=2.0, 8.6 Hz), 6.96 (1H, d, J=8.6 Hz), 7.10–7.55 (10H, m).

Example 50

2-Benzyl-7-(3,3-dimethyl-4-phenylbutoxy)-1,2,3,4-tetrahydroisoquinoline-(3S)-carboxylic acid IR ν (nujol) cm$^{-1}$; 1611, 1506.
$^1$H-NMR (DMSO-d$_6$) δ (ppm);
0.87 (6H, S), 1.61 (2H, t, J=7.0 Hz), 2.54 (2H, s), 2.85–3.15 (2H, m), 3.50–4.20 (5H, m), 3.91 (2H, s), 4.20–6.00 (1H, br), 6.60 (1H, br-s), 6.67 (1H, d, J=8.6 Hz), 7.01 (1H, d, J=8.6 Hz), 7.05–7.50 (10H, m).

Example 51

2-Benzyl-7-(2-isopropylbenzoxazol-6-yl)methoxy-1,2,3,4-tetrahydroisoquinoline-(3S)-carboxylic acid IR ν (Nujol) cm$^{-1}$; 1632, 1585, 1572, 1501.
$^1$H-NMR (DMSO-d$_6$) δ (ppm);
1.37 (6H, d, J=7.0 Hz), 2.85–3.45 (4H, m), 3.50–4.20 (6H, m), 5.12 (2H, s), 6.69 (1H, s), 6.77 (1H, d, J=8.6 Hz), 7.04 (1H, d, J=8.6 Hz), 7.25–7.85 (8H, m).

Example 52

2-Benzyl-7-(2-tert-butylbenzoxazol-6-yl)methoxy-1,2,3,4-tetrahydroisoquinoline-(3S)-carboxylic acid IR ν (Nujol) cm$^{-1}$; 1611, 1583, 1562, 1506.
$^1$H-NMR (DMSO-d$_6$) δ (ppm);
1.42 (9H, s), 2.85–3.10 (2H, br), 3.50–4.20 (6H, m), 5.13 (2H, s), 6.70 (1H, s), 6.77 (1H, d, J=8.4 Hz), 7.04 (1H, d, J=8.4 Hz), 7.20–7.50 (6H, m), 7.55–7.65 (1H, m), 7.70 (1H, s).

Example 53

2-Benzyl-7-(2-tert-butylbenzoxazol-5-yl)methoxy-1,2,3,4-tetrahydroisoquinoline-(3S)-carboxylic acid IR ν (nujol) cm$^{-1}$; 1717, 1645, 1612, 1553.
$^1$H-NMR (DMSO-d$_6$) δ (ppm);
1.43 (9H, s), 2.85–3.15 (2H, m), 3.50–4.15 (3H, m), 3.90 (2H, s), 5.11 (2H, s), 6.69 (1H, br-s), 6.75 (1H, d, J=8.1 Hz), 7.03 (1H, d, J=8.1 Hz), 7.10–7.50 (6H, m), 7.65 (1H, d, J=9.0), 7.71 (1H, br-s).

Example 54

7-(2-tert-Butylbenzoxazol-6-yl)methoxy-2-(2,2-dimethylpropyl)-1,2,3,4-tetrahydroisoquinoline-(3S)-carboxylic acid IR ν (nujol) cm$^{-1}$; 1740, 1612, 1560, 1508.
$^1$H-NMR (DMSO-d$_6$) δ (ppm);
1.10 (9H, s), 1.43 (9H, s), 2.79, 3.19 (2H, ABq, J=13.6 Hz), 3.20–3.45 (3H, m), 4.25–4.55 (4H, br), 5.20 (2H, s), 6.96 (1H, d, J=8.1 Hz), 7.00 (1H, s), 7.20 (1H, d, J=8.1 Hz), 7.40 (1H, d, J=8.1 Hz), 7.68 (1H, d, J=8.1 Hz), 7.73 (1H, s).

Example 55

2-Benzyl-7-(2-isopropylbenzoxazol-5-yl)methoxy-1,2,3,4-tetrahydroisoquinoline-(3S)-carboxylic acid IR ν (nujol) cm$^{-1}$; 1634, 1587, 1570, 1501.
$^1$H-NMR (DMSO-d$_6$) δ (ppm);
1.37 (6H, d, J=6.8 Hz), 2.90–3.15 (2H, m), 3.25 (1H, quintet, J=6.8 Hz), 3.50–4.30 (7H, m), 5.11 (2H, s), 6.69 (1H, s), 6.76 (1H, d, J=8.1 Hz), 7.04 (1H, d, J=8.1 Hz), 7.20–7.50 (6H, m), 7.55–7.65 (1H, m), 7.70 (1H, s).

Example 56

Sodium 7-[2-(5-methyl-2-phenyloxazol-4-yl)ethoxy]-2-(pyridin-4-ylmethyl)-1,2,3,4-tetrahydroisoquinoline-(3S)-carboxylate IR ν (nujol) cm$^{-1}$; 3420, 3177, 1639, 1558, 1504.
$^1$H-NMR (DMSO-d$_6$) δ (ppm);
2.34 (3H, s), 2.70–3.05 (4H, m), 3.10–3.60 (3H, m), 3.98 (2H, br-t, J=5.7 Hz), 4.10–4.25 (2H, m), 6.51 (1H, br-s), 6.61 (1H, br-d, J=8.7 Hz), 6.94 (1H, br-d, J=8.7 Hz), 7.25–7.65 (5H, m), 7.75–8.00 (2H, m), 8.46 (2H, d, J=5.2 Hz).

Example 57

Sodium 7-[2-(5-methyl-2-phenyloxazol-4-yl)ethoxy]-2-[(pyridin-2-yl)carbonyl]-1,2,3,4-tetrahydroisoquinoline-(3S)-carboxylate IR ν (nujol) cm$^{-1}$; 3385, 1624, 1566, 1504.
$^1$H-NMR (MeOH-d$_4$) δ (ppm);
2.31, 2.36 (3H, s, s), 2.75–3.05 (2H, m), 3.05–3.30 (2H, m), 4.00–4.30 (2H, m), 4.50–5.30 (3H, m), 6.60–6.80 (2H, m) 7.03 (1H, dd, J=2.0, 8.5 Hz), 7.30–7.75 (5H, m), 7.75–8.10 (3H, m), 8.50–8.70 (1H, m).

Example 58

Methyl 2-benzyl-7-[2-(5-methyl-2-phenyloxazol-4-yl)ethoxy]-1,2,3,4-tetrahydroisoquinoline-(3S)-carboxylate IR ν (nujol) cm$^{-1}$; 1736, 1639, 1612, 1504.
$^1$H-NMR (CDCl$_3$) δ (ppm);
2.34 (3H, s), 2.92 (2H, t, J=7.0 Hz), 3.07 (2H, d, J=5.0 Hz), 3.64 (3H, s), 3.64–4.00 (5H, m), 4.17 (2H, t, J=7.0 Hz), 6.51 (1H, d, J=2.0 Hz), 6.68 (1H, dd, J=2.0, 8.4 Hz), 6.98 (1H, d, J=8.4 Hz), 7.20–7.60 (8H, m), 7.80–8.10 (2H, m).

Example 59

2-Benzyl-7-[2-(2-cyclopropyl-5-methyloxazol-4-yl)ethoxy]-1,2,3,4-tetrahydroisoquinoline-(3S)-carboxylic acid IR ν (nujol) cm$^{-1}$; 3470, 1684, 1618, 1583, 1510.
$^1$H-NMR (DMSO-d$_6$) δ (ppm);
0.70–1.10 (4H, m), 1.80–2.20 (1H, m), 2.16 (3H, s), 2.60–2.85 (2H, m), 2.90–3.15 (2H, m), 3.50–4.20 (5H, m), 6.50–6.80 (2H, m), 7.03 (1H, d, J=8.1 Hz), 7.34 (5H, s).

Example 60

2-(3-Methyl-2-butenyl)-7-[2-(5-methyl-2-phenyloxazol-4-yl)ethoxy]-1,2,3,4-tetrahydroisoquinoline-(3S)-carboxylic acid IR ν (nujol) cm$^{-1}$; 3447, 3335, 1670, 1668, 1622, 1556, 1506.
$^1$H-NMR (DMSO-d$_6$) δ (ppm);
1.61 (3H, s), 1.72 (3H, s), 2.35 (3H, s), 2.70–3.20 (4H, m), 3.39 (2H, d, J=7.0 Hz), 3.50–4.01 (3H, m), 4.16 (2H, t, J=7.0 Hz), 4.35–5.60 (1H, br), 5.25 (1H, br-t), 6.67 (1H, s), 6.71 (1H, d, J=8.4 Hz), 7.02 (1H, d, J=8.4 Hz), 7.30–7.70 (8H, m), 7.75–8.10 (2H, m).

Example 61

2-(2,2-Dimethylpropyl)-7-[2-(5-methyl-2-tert-butyloxazol-4-yl)ethoxy]-1,2,3,4-tetrahydroisoquinoline-(3S)-carboxylic acid IR ν (nujol) cm$^{-1}$; 1717, 1614, 1566, 1504.
$^1$H-NMR (CDCl$_3$) δ (ppm);
0.97 (9H, s), 1.33 (9H, s), 2.24 (3H, s), 2.44, 2.68 (2H, ABq, J=13.9 Hz), 2.84 (2H, t, J=6.7 Hz), 3.00–3.22 (2H, m), 3.65 (3H, t, J=6.1 Hz), 3.83, 4.08 (2H, ABq, J=15.1 Hz), 4.07 (2H, t, J=6.7 Hz), 6.58 (1H, d, J=1.7 Hz), 6.72 (1H, dd, J=1.7, 8.4 Hz), 7.05 (1H, d, J=8.4 Hz), 7.50–8.20 (1H, br).

Example 62

2-Benzyl-7-{2-[2-(1-butenyl)-5-methyloxazol-4-yl]ethoxy}-1,2,3,4-tetrahydroisoguinoline-(3S)-carboxylic acid IR ν (nujol) cm$^{-1}$; 3470, 1682, 1614, 1585, 1512.
$^1$H-NMR (CDCl$_3$) δ (ppm);
1.07 (3H, t, J=7.5 Hz), 2.05–2.20 (1H, m), 2.26 (3H, s), 2.50–3.00 (3H, m), 3.65–4.45 (7H, m), 5.92 (1H, br-s), 6.17 (1H, d, J=16.3 Hz), 6.45–6.85 (3H, m), 7.05 (1H, d, J=8.4 Hz), 7.34 (5H, s).

Example 63

2-Benzyl-7-{2-[2-(2,2-dimethylpropyl)-5-methyloxazol-4-yl]ethoxy}-1,2,3,4-tetrahydroisoquinoline-(3S)-carboxylic acid IR ν (nujol) cm$^{-1}$; 1722, 1614, 1568, 1506.
$^1$H-NMR (CDCl$_3$) δ (ppm);
0.95 (9H, s), 2.34 (3H, s), 2.55 (2H, s), 2.60–3.00 (2H, m), 3.00–3.30 (2H, m), 3.80–4.40 (7H, m), 6.64 (1H, br-s), 6.70 (1H, d, J=8.8 Hz), 7.02 (1H, d, J=8.8 Hz), 7.32 (5H, s), 7.80 (1H, br-s).

Example 64

Ethyl 2-(2,2-dimethylpropyl)-7-[2-(5-methyl-2-phenyloxazol-4-yl)ethoxy]-1,2,3,4-tetrahydroisoquinoline-(3S)-carboxylate hydrochloride IR ν (nujol) cm$^{-1}$; 3400, 1744, 1676, 1614, 1589, 1574, 1553, 1508.

$^1$H-NMR (DMSO-d$_6$) δ (ppm);

1.12 (9H, s), 1.23 (3H, t, J=7.0 Hz), 2.36 (3H, s), 2.60–3.60 (6H, m), 4.00–4.40 (4H, m), 4.40–6.00 (4H, m), 6.88 (1H, d, J=8.0 Hz), 6.92(1H, s), 7.18 (1H, d, J=8.0 Hz), 7.35–7.70 (8H, m), 7.75–8.10 (2H, m).

Example 65

7-(Benzofran-2-ylmethoxy)-2-benzyl-1,2,3,4-tetrahydroisoquinoline-(3S)-carboxylic acid IR ν (nujol) cm$^{-1}$; 1632, 1587, 1501.

$^1$H-NMR (DMSO-d$_6$) a (ppm);

2.00–6.50 (1H, br), 2.85–3.15 (2H, m), 3.50–4.10 (3H, m), 3.91 (2H, s), 5.16 (2H,s), 6.60–7.80 (8H, m), 7.33 (5H,s).

Example 66

2-Isobutyryl-7-[2-(5-methyl-2-phenyloxazol-4-yl)ethoxy]-1,2,3,4-tetrahydroisoquinoline-(3S)-carboxylic acid IR ν (nujol) cm$^{-1}$; 1736, 1639, 1612, 1504.

$^1$H-NMR (DMSO-d$_6$) δ (ppm);

1.02 (6H, br-d), 2.35 (3H, s), 2.65–3.30 (5H, m), 4.00–5.30 (6H, m), 6.60–6.95 (2H, m), 7.09 (1H, d, J=8.0 Hz), 7.25–7.70 (8H, m), 7.70–8.10 (2H, m).

Example 67

7-[2-(Benzofran-2-yl)ethoxy]-2-benzyl-1,2,3,4-tetrahydroisoquinoline-(3S)-carboxylic acid IR ν (nujol) cm$^{-1}$; 1634, 1585, 1501.

$^1$H-NMR (DMSO-d$_6$) δ (ppm);

2.80–3.10 (2H, m), 3.19 (2H, br-t), 3.45–4.10 (3H, m), 3.90 (2H,s), 4.25 (2H, br-t), 6.50–7.80 (9H, m), 7.33 (5H, s).

Example 68

7-[2-(5-Ethylpyridin-2-yl)ethoxy]-2-hexanoyl-1,2,3,4-tetrahydroisoquinoline-(3S)-carboxylic acid hydrochloride $^1$H-NMR (CDCl$_3$) δ (ppm);

0.87 (3H, br-t), 1.05–1.85 (9H, m), 2.15–2.55 (4H, m), 2.55–3.75 (4H, m), 4.00–4.90 (4H, m), 5.25–5.50 (1H, m), 6.40–7.10 (4H, m), 7.75 (1H, br-d), 8.15 (1H, br-d), 8.52 (1H, br-s).

Example 69

2-Carboxymethyl-7-[2-(5-methyl-2-phenyloxazol-4-yl)ethoxy]-1,2,3,4-tetrahydroisoquinoline-(3S)-carboxylic acid IR ν (nujol) cm$^{-1}$; 1620, 1585, 1556, 1508.

$^1$H-NMR (DMSO-d$_6$) δ (ppm);

2.35 (3H, s), 2.70–3.15 (4H, m), 3.41, 3.65 (2H, ABq, J=17.5 Hz), 3.70–4.00 (3H, m), 4.16 (2H, t, J=7.0 Hz), 6.00–11.00 (1H, br), 6.64 (1H, s), 6.69 (1H, d, J=8.2 Hz), 7.01 (1H, d, J=8.2 Hz), 7.20–7.70 (8H, m), 7.70–8.05 (2H, m).

Example 70

2-[3-(Methoxycarbonyl)propionyl]-7-[2-(5-methyl-2-phenyloxazol-4-yl)ethoxy]-1,2,3,4-tetrahydroisoquinoline-(3S)-carboxylic acid IR ν (nujol) cm$^{-1}$; 1732, 1652, 1554, 1505.

$^1$H-NMR (CDCl$_3$) δ (ppm);

2.33 (3H, s), 2.50–3.40 (7H, m), 3.65 (3H, s), 4.07 (2H, br-t), 4.45–5.50 (3H, m), 5.60–6.20 (1H, br), 6.59 (1H, br-s), 6.67 (1H, d, J=8.0 Hz), 7.03 (1H, d, J=8.0 Hz), 7.20–7.60 (3H, m), 7.80–8.10 (2H, m).

Example 71

2-[3-(Ethoxycarbonyl)propyl]-7-[2-(5-methyl-2-phenyloxazol-4-yl)ethoxy]-1,2,3,4-tetrahydroisoquinoline-(3S)-carboxylic acid IR ν (nujol) cm$^{-1}$; 3375, 1733, 1620, 1555, 1505.

$^1$H-NMR (CDCl$_3$) δ (ppm);

1.18 (3H, t, J=7.0 Hz), 1.76–2.15 (2H, m), 2.15–2.50 (2H, m), 2.35 (3H, s), 2.70–3.35 (6H, m), 3.60–4.40 (7H, m), 5.27 (1H, br-s), 6.61(1H, br-s), 6.73 (1H, d, J=8.4 Hz), 7.03 (1H, d, J=8.4 Hz), 7.25–7.55 (3H, m), 7.80–8.10 (2H, m).

Example 72

2-Benzyl-6-[2-(5-methyl-2-phenyloxazol-4-yl)ethoxy]-1,2,3,4-tetrahydroisoquinoline-(3RS)-carboxylic acid IR ν (nujol) cm$^{-1}$; 1634, 1614, 1499.

$^1$H-NMR (DMSO-d$_6$) δ (ppm);

2.35 (3H, s), 2.65–3.25 (4H, m), 3.40–4.00 (3H, m), 3.90 (2H, s), 4.17 (2H, br-t), 6.20–10.00 (1H, br), 6.50–7.00 (2H, m), 6.71 (1H, s), 7.30–7.70 (3H, m), 7.32 (5H, s), 7.75–8.15 (2H, m).

Example 73

2-(3-Acetylbenzyl)-7-[2-(5-methyl-2-phenyloxazol-4-yl)ethoxy]-1,2,3,4-tetrahydroisoquinoline-(3S)-carboxylic acid IR ν (nujol) cm$^{-1}$; 1682, 1620, 1508.

$^1$H-NMR (DMSO-d$_6$) δ (ppm);

2.33 (3H, s), 2.56 (3H, s), 2.70–3.20 (4H, m), 3.50–4.30 (5H, m), 3.97 (2H, s), 6.50–6.90 (2H, m), 7.02 (1H, d, J=8.4 Hz), 7.30–8.00 (9H, m).

Example 74

2-(2-Acetylbenzyl)-7-[2-(5-methyl-2-phenyloxazol-4-yl)ethoxy]-1,2,3,4-tetrahydroisoquinoline-(3S)-carboxylic acid IR ν (nujol) cm$^{-1}$; 1668, 1643, 1614, 1504.

$^1$H-NMR (DMSO-d$_6$) δ (ppm);

2.33 (3H, s), 2.36 (3H, s), 2.70–3.20 (4H, m), 3.30–4.30 (5H, m), 6.57 (1H, d, J=2.0 Hz), 6.66 (1H, dd, J=2.0, 8.4 Hz), 7.00 (1H, d, J=8.4 Hz), 7.20–7.75 (7H, m), 7.75–8.10 (2H, m).

Example 75

2-Benzyl-7-[(5-methyl-2-phenyloxazol-4-yl)methoxy]-1,2,3,4-tetrahydroisoquinoline-(3S)-carboxylic acid IR ν (nujol) cm$^{-1}$; 3462, 1680, 1614, 1556, 1508.

$^1$H-NMR (DMSO-d$_6$) δ (ppm);

2.41 (3H, s), 2.83–3.20 (2H, m), 3.44–4.20 (5H, m), 4.91 (2H, s), 6.73 (1H, br-s), 6.77 (1H, d, J=8.1 Hz), 7.34 (1H, d, J=8.1 Hz), 7.34 (5H, s), 7.40–7.68 (3H, m), 7.75–8.10 (2H, m).

Reference Example 1

Ethyl 2-tert-butoxycarbonyl-7-hydroxy-1,2,3,4-tetrahydroisoquinoline-(3S)-carboxylate (1) 3,5-Diiodo-L-tyrosine dihydrate (25.0 g) was suspended in concentrated hydrochloric acid (250 ml). Thereto were successively added 1,2-dimethoxyethane (18 ml) and 37% formalin (20 ml), and the mixture was warmed to 75° C. over 30 min. To the reaction mixture were further added concentrated hydrochloric acid (120 ml), 1,2-dimethoxyethane (9 ml) and 37% formalin (10 ml), and the mixture was stirred at 75° C. for 18 hr. The precipitated crystals were collected by filtration and washed with 1,2-dimethoxyethane (20 ml) to give 7-hydroxy-6,8-diiodo-1,2,3,4-tetrahydroisoquinoline-(3S)-carboxylic acid hydrochloride (12.8 g).

7-Hydroxy-6,8-diiodo-1,2,3,4-tetrahydroisoquinoline-(3S)-carboxylic acid hydrochloride IR ν (nujol) cm$^{-1}$; 1751, 1599, 1578.
$^{1}$H-NMR (CDCl$_3$) δ (ppm);
3.00–3.30 (2H, m), 4.05 (2H, s), 4.30 (1H, dd, J=5.9, 9.5 Hz), 7.71 (1H, s).

(2) The compound (12.8 g) obtained in (1) above was suspended in ethanol (500 ml). Thereto was added concentrated hydrochloric acid (10 ml) and the mixture was refluxed for 15 hr. Ethanol was evaporated under reduced pressure. Ethyl acetate (300 ml) was added to the obtained residue, and the compound was washed with saturated aqueous sodium hydrogencarbonate solution (100 ml) and saturated brine (100 ml) and dried over Na$_2$SO$_4$. Ethyl acetate was evaporated under reduced pressure to give ethyl 7-hydroxy-6,8-diiodo-1,2,3,4-tetrahydroisoquinoline-(3S)-carboxylate (11.11 g).

Ethyl 7-hydroxy-6,8-diiodo-1,2,3,4-tetrahydroisoquinoline-(3S)-carboxylate $^{1}$H-NMR (CDCl$_3$) δ (ppm);
1.29 (3H, t, J=7.0 Hz), 2.80–3.00 (2H, m), 3.30–4.10 (5H, m), 4.23 (2H, q, J=7.0 Hz), 7.46 (1H, s).

(3) 10% Pd-C (350 mg) was suspended in methanol (60 ml). Thereto were added triethylamine (2.0 ml) and the compound (2.80 g) obtained in (2) above, and the compound was catalytically hydrogenated at room temperature, 29.4×10$^4$ Pa (3.0 kgf/cm$^2$) for 3 hr. Pd-C was filtered off, and methanol was evaporated under reduced pressure. Ethyl acetate (10 ml) was added to the obtained residue. The mixture was washed with saturated brine (100 ml) and dried over Na$_2$SO$_4$. Ethyl acetate was evaporated under reduced pressure to give ethyl 7-hydroxy-1,2,3,4-tetrahydroisoquinoline-(3S)-carboxylate (1.14 g).

Ethyl 7-hydroxy-1,2,3,4-tetrahydroisoquinoline-(3S)-carboxylate

IR ν (nujol) cm$^{-1}$; 1732, 1607, 1516.
$^{1}$H-NMR (CDCl$_3$) δ (ppm);
1.28 (3H, t, J=7.0 Hz), 2.80–3.10 (3H, m), 3.60–3.80 (1H, m), 3.97 (2H, s), 4.05–4.20 (4H, m), 6.43 (1H, s), 6.50–6.80 (1H, m), 6.92 (1H, d, J=8.4 Hz).

(4) The compound (1.13 g) obtained in (3) above was dissolved in tetrahydrofuran (20 ml). Thereto was added di-tert-butyl dicarbonate (1.50 g) and the mixture was stirred at room temperature for 1 hr. Ethyl acetate (30 ml) was added to the reaction mixture, and the mixture was washed with saturated brine (20 ml) and dried over Na$_2$SO$_4$. Ethyl acetate was evaporated under reduced pressure. The obtained residue was purified by column chromatography to give the title compound (1.51 g).

IR ν (nujol) cm$^{-1}$; 3260, 1756, 1671, 1615, 1506.
$^{1}$H-NMR (CDCl$_3$) δ (ppm);
1.29 (3H, t, J=7.0 Hz), 1.47 (9H, s), 3.08 (2H, d, J=5.2 Hz), 4.21 (2H, q, J=7.0 Hz), 4.41 (1H, d, J=15.5 Hz), 4.60–5.25 (1H, m), 4.65 (1H, d, J=15.5 Hz), 5.00–6.00 (1H, br), 6.50–6.80 (2H, m), 6.98 (1H, d, J=8.1 Hz).

Reference Example 2

Methyl 2-tert-butoxycarbonyl-7-hydroxy-1,2,3,4-tetrahydroisoquinoline-(3S)-carboxylate In the same manner as in Reference Example 1, the title compound was obtained.

IR ν (nujol) cm$^{-1}$; 3261, 1755, 1672, 1614, 1506.
$^{1}$H-NMR (CDCl$_3$) δ (ppm);
1.47 (9H, s), 3.08 (2H, d, J=5.2 Hz), 3.63 (3H, s), 4.40 (1H, d, J=16.5 Hz), 4.60–5.25 (1H, m), 4.66 (1H, d, J=16.5 Hz), 5.60–6.60 (1H, br), 6.50–6.80 (2H, m), 6.99 (1H, d, J=8.1 Hz).

Reference Example 3

2-(5-Methyl-2-phenyl-oxazol-4-yl)ethyl methanesulfonate

To methylene chloride (200 ml) were added 2-(5-methyl-2-phenyl-oxazol-4-yl)ethanol (20 g) and triethylamine (19.2 ml). Thereto was dropwise added methanesulfonyl chloride (9.52 ml) at 0° C. and the mixture was stirred at the same temperature for 15 min. The mixture was washed with 10% aqueous citric acid solution (200 ml), saturated aqueous sodium hydrogencarbonate solution (100 ml) and saturated brine (100 ml) and dried over Na$_2$SO$_4$. Methylene chloride was evaporated under reduced pressure. The obtained residue was purified by column chromatography to give the title compound (21.45 g).

$^{1}$H-NMR (CDCl$_3$) δ (ppm);
2.53 (3H, s), 2.94 (3H, s), 2.94 (2H, t, J=7.0 Hz), 4.52 (2H, t, J=7.0 Hz), 7.30–7.50 (3H, m), 7.80–8.10 (2H, m).

Reference Example 4

Ethyl 2-benzyl-7-hydroxy-1,2,3,4-tetrahydroisoquinoline-(3S)-carboxylate

The compound (8.1 g) obtained in Reference Example 1(3) was dissolved in N,N-dimethylformamide (80 ml). Thereto were added triethylamine (2.0 ml) and benzyl bromide (4.57 ml) and the mixture was stirred at room temperature for 3 hr. Water (500 ml) was added to the reaction mixture, and the mixture was extracted twice with ethyl acetate (200 ml). The combined ethyl acetate layer was washed with saturated brine (500 ml) and dried over Na$_2$SO$_4$. Ethyl acetate was evaporated under reduced pressure. The obtained residue was purified by column chromatography to give the title compound (10.46 g).

IR ν (nujol) cm$^{-1}$; 3410, 1717, 1624, 1506.
$^{1}$H-NMR (CDCl$_3$) δ (ppm);
1.22 (3H, t, J=7.0 Hz), 3.06 (2H, d, J=5.0 Hz), 3.66 (1H, t, J=5.0 Hz), 3.78 (2H, s), 3.90 (2H, s), 4.13 (2H, q, J=7.0 Hz), 6.37 (1H, d, J=2.0 Hz), 6.56 (1H, dd, J=2.0, 8.4 Hz), 6.92 (1H, d, J=8.4 Hz), 7.20–7.50 (5H, m).

Reference Example 5

2-(N-tert-Butoxycarbonyl-N-methylamino)ethyl methanesulfonate (1) 2-(Methylamino)ethanol (3.5 ml) was dissolved in tetrahydrofuran (150 ml). Thereto was added di-tert-butyl dicarbonate (12.5 g) and the mixture was stirred at room temperature for 20 min. Tetrahydrofuran was evaporated under reduced pressure. The obtained residue was purified by column chromatography to give 2-(N-tert-butoxycarbonyl-N-methylamino)ethanol (6.35 g).
2-(N-tert-Butoxycarbonyl-N-methylamino)ethanol
IR ν(neat) cm$^{-1}$; 3423, 2976, 2934, 2882, 1674.
$^1$H-NMR (CDCl$_3$) δ (ppm);
1.43 (9H, s), 2.89 (3H, s), 3.34 (2H, t, J=5.8 Hz), 3.67 (2H, t, J=5.8 Hz), 4.00–6.00 (1H, br).

(2) The compound (505 mg) obtained in (1) above was dissolved in methylene chloride (20 ml). Thereto were added triethylamine (0.5 ml) and methanesulfonyl chloride (0.25 ml) and the mixture was stirred at room temperature for 1 hr. Methylene chloride (30 ml) was added to the mixture, and the mixture was washed with saturated brine (20 ml) and dried over Na$_2$SO$_4$. Methylene chloride was evaporated under reduced pressure to give the title compound (720 mg).
$^1$H-NMR (CDCl$_3$) δ (ppm);
1.46 (9H, s), 2.94 (3H, s), 3.01 (3H, s), 3.54 (2H, t, J=5.5 Hz), 4.33 (2H, t, J=5.5 Hz).

Reference Example 6

1-(2-Bromoethyl)indoline

To 1,2-dibromoethane (58.0 ml) were added indoline (5.0 g) and triethylamine (28.7 ml), and the mixture was stirred at 90° C. for 2 hr. Ethyl acetate (200 ml) was added to the reaction mixture, and the mixture was washed with saturated brine (400 ml) and dried over Na$_2$SO$_4$. Ethyl acetate was evaporated under reduced pressure. The obtained residue was purified by column chromatography to give the title compound (4.09 g).

IR ν(neat) cm$^{-1}$; 2924, 2845, 1607, 1489.
$^1$H-NMR (CDCl$_3$) δ (ppm);
2.99 (1H, t, J=8.4 Hz), 3.45 (1H, t, J=8.4 Hz), 3.49 (4H, s), 6.40–6.75 (2H, m), 6.90–7.20 (2H, m).

Reference Example 7

1-(2-Bromoethyl)-6-methoxycarbonylindoline

To 1,2-dibromoethane (15.7 ml) were added 6-methoxycarbonylindoline (2.41 g) and triethylamine (7.8 ml), and the mixture was stirred at 90° C. for 2 hr. Ethyl acetate (150 ml) was added to the reaction mixture, and the mixture was washed with saturated brine (300 ml) and dried over Na$_2$SO$_4$. Ethyl acetate was evaporated under reduced pressure. The obtained residue was purified by column chromatography to give the title compound (1.71 g).

IR ν(neat) cm$^{-1}$; 1713, 1611, 1499.
$^1$H-NMR (CDCl$_3$) δ (ppm);
3.03 (1H, t, J=8.4 Hz), 3.53 (1H, t, J=8.4 Hz), 3.53 (4H, s), 3.88 (3H, s), 6.00–6.20 (2H, m), 7.39 (1H, dd, J=1.5, 7.8 Hz).

Experimental Example 1

Hypoglycemic Action (Method A)

Blood was drawn under a non-fasting state from the tail vein of male KK-A$^y$ mice, which were spontaneously diabetic models, had developed diabetes due to insulin resistance and which showed hyperglycemia and hyperinsulinemia. The glucose level in the plasma was measured using a commercially available assay kit (glucose CII-test WAKO, Wako Pure Chemical Industries, Ltd.). The mice were grouped (5 mice per group) into a control group and an administration group, such that the mean and the standard deviation of the glucose level in the plasma of each group were nearly the same. Each test compound was suspended or dissolved in 5% gum arabic solution and administered orally to the administration group for 4 consecutive days from the next day. The 5% gum arabic solution was orally administered to the control group. Blood was drawn from the tail vein under a non-fasting state about 24 hours after the final administration and the glucose level in the plasma was measured. The decrease in the plasma glucose level was calculated from the following formula. The results are shown in Table 1.

Decrease (%) in plasma glucose level=[(mean plasma glucose level of control group−mean plasma glucose level of test compound administration group)/mean plasma glucose level of control group]×100

TABLE 1

Hypoglycemic action (method A)

| Test compound | Dose (mg/kg) | Decrease (%) in plasma glucose level |
|---|---|---|
| Example 2 | 10 | 38.3 |
|  | 30 | 60.6 |
| Example 3 | 30 | 11.8 |
| Example 5 | 10 | 34.1 |
|  | 30 | 43.4 |
| Example 6 | 10 | 10.7 |
|  | 30 | 12.2 |
| Example 7 | 10 | 11.4 |
|  | 30 | 17.4 |
| Example 9 | 30 | 20.3 |
| Example 12 | 10 | 12.0 |
| Example 16 | 30 | 34.5 |
| Example 18 | 30 | 39.7 |
| Example 21 | 30 | 43.4 |
| Example 23 | 10 | 24.3 |
|  | 30 | 42.9 |
| Example 32 | 30 | 36.4 |
| Example 33 | 30 | 38.8 |
| Example 34 | 30 | 23.5 |
| Example 35 | 30 | 22.1 |
| Example 36 | 30 | 28.4 |
| Example 37 | 30 | 11.1 |
| Example 38 | 30 | 28.0 |
| Example 39 | 30 | 30.7 |
| Example 40 | 30 | 46.3 |
| Example 41 | 30 | 11.1 |
| Example 42 | 10 | 27.6 |
|  | 30 | 49.6 |
| Example 43 | 30 | 27.5 |
| Example 44 | 30 | 48.0 |
| Example 45 | 30 | 12.6 |
| Example 46 | 30 | 28.6 |
| Example 48 | 30 | 16.1 |
| Example 49 | 30 | 11.1 |
| Example 50 | 30 | 11.4 |
| Example 51 | 30 | 20.0 |
| Example 52 | 30 | 26.3 |
| Example 53 | 30 | 13.6 |
| Example 54 | 30 | 10.8 |
| Example 55 | 30 | 13.9 |
| Example 58 | 30 | 19.1 |
| Example 67 | 30 | 10.6 |
| Example 69 | 30 | 12.5 |

TABLE 1-continued

Hypoglycemic action (method A)

| Test compound | Dose (mg/kg) | Decrease (%) in plasma glucose level |
|---|---|---|
| Example 70 | 30 | 15.2 |
| Example 71 | 30 | 10.5 |
| Example 72 | 30 | 15.9 |
| Example 73 | 30 | 14.8 |

Experimental Example 2

Hypoglycemic Action (Method B)

Blood was drawn under a non-fasting state from the tail vein of male KK-A$^y$ mice, which were spontaneously diabetic models, had developed diabetes due to insulin resistance and which showed hyperglucemia and hyperinsulemia. The glucose level in the plasma was measured using a commercially available assay kit (glucose CII-test WAKO, Wako Pure Chemical Industries, Ltd.). The mice were grouped (5 mice per group) into a control group and an administration group, such that the mean and the standard deviation of the glucose level in the plasma of each group were nearly the same. Each test compound was admixed in a proportion of 0.1 w/w % with a powder feed (CE-2, Clea) and the feed mixture was fed to the administration group for 4 days from the next day. A regular powder feed was fed to the control group. At day 5, blood was drawn from the tail vein under a non-fasting state and the glucose level in the plasma was measured. The decrease in the plasma glucose level was calculated from the following formula. The results are shown in Table 2.

Decrease (%) in plasma glucose level=[(mean plasma glucose level of control group−mean plasma glucose level of test compound administration group)/mean plasma glucose level of control group]×100

TABLE 2

Hypoglycemic action (method B)

| Test compound | Decrease (%) in plasma glucose level |
|---|---|
| Example 2 | 69.2 |
| Example 10 | 42.4 |

Experimental Example 3

Hypotriglyceridemic Action

Blood was drawn under a non-fasting state from the tail vein of male KK-A$^y$ mice, which were spontaneously diabetic models, had developed diabetes due to insulin resistance, and which showed hyperglycemia and hyperinsulinemia. The triglyceride level in the plasma was measured using a commercially available assay kit (triglyceride G-test WAKO, Wako Pure Chemical Industries, Ltd.). The mice were grouped (5 mice per group) into a control group and an administration group, such that the mean and the standard deviation of the triglyceride level in the plasma of each group were nearly the same. Each test compound was suspended or dissolved in 5% gum arabic solution and administered orally to the administration group for 4 consecutive days from the next day. The 5% gum arabic solution was orally administered to the control group. Blood was drawn from the tail vein under a non-fasting state about 24 hours after the final administration and the triglyceride level in the plasma was measured. The decrease in the plasma triglyceride level was calculated from the following formula. The results are shown in Table 3.

Decrease (%) in plasma triglyceride level=[(mean plasma triglyceride level of control group−mean plasma triglyceride level of test compound administration group)/mean plasma triglyceride level of control group]×100

TABLE 3 hypotriglyceridemic action

| Test compound | Dose (mg/kg) | Decrease (%) in plasma triglyceride level |
|---|---|---|
| Example 2 | 10 | 39.5 |
|  | 30 | 54.3 |
| Example 4 | 10 | 14.3 |
| Example 5 | 30 | 30.9 |
| Example 11 | 10 | 11.2 |
| Example 12 | 10 | 22.9 |
| Example 16 | 30 | 19.8 |
| Example 18 | 30 | 45.5 |
| Example 21 | 30 | 24.4 |
| Example 23 | 10 | 30.4 |
|  | 30 | 50.4 |
| Example 32 | 30 | 32.5 |
| Example 33 | 30 | 42.0 |
| Example 34 | 30 | 17.3 |
| Example 35 | 30 | 12.4 |
| Example 36 | 30 | 13.7 |
| Example 38 | 30 | 30.0 |
| Example 39 | 30 | 15.6 |
| Example 40 | 30 | 36.1 |
| Example 42 | 30 | 31.6 |
| Example 43 | 30 | 20.9 |
| Example 44 | 30 | 19.1 |
| Example 49 | 30 | 17.0 |
| Example 50 | 30 | 35.7 |
| Example 51 | 30 | 10.7 |
| Example 52 | 30 | 26.6 |
| Example 56 | 30 | 14.0 |
| Example 58 | 30 | 24.7 |
| Example 59 | 30 | 13.7 |
| Example 69 | 30 | 15.2 |
| Example 72 | 30 | 24.0 |
| Example 73 | 30 | 15.4 |

Experimental Example 4

Hypoglycemic Action and Hypoinsulinemic Action in Insulin Resistant Diabetic Mouse The insulin resistance improving action was examined in KK-A$^y$ mice, which were spontaneously diabetic models, had developed diabetes due to insulin resistance, and which showed hyperglycemia and hyperinsulinemia. Blood was drawn from the tail vein of 12-week-old male KK-A$^y$ mice under a non-fasting state, and the glucose level in the plasma was measured using a commercially available assay kit (glucose CII-test WAKO, Wako Pure Chemical Industries, Ltd.). The mice were grouped (5 mice per group) into a control group and an administration group, such that the mean glucose level in the plasma and the average body weight of each group, as well as the standard deviation thereof were nearly the same. The test compound (10 mg/kg) was suspended in 5% aqueous gum arabic solution and orally administered once a day to the administration group for 4 days from the next day. The 5% aqueous gum arabic solution was orally administered to the control group. Blood was drawn from the tail vein under a non-fasting state 24 hours after the final administration. The concentrations of plasma glucose and plasma insulin were measured. The results are shown in Table 4.

As a result, each test compound (10 mg/kg) lowered the glucose level in plasma and also decreased the insulin concentration in plasma. This means that the test compound lowered the plasma glucose level not by insulin secretion but by insulin sensitivity potentiating action (insulin resistance improving action), thereby to improve hyperinsulinemia.

TABLE 4

Hypoglycemic action and Hypoinsulinemic action

| Test compound | Dose of test compound (mg/kg) | Plasma glucose (mg/dl) | Insulin (ng/ml) |
|---|---|---|---|
| Control | 0 | 507 | 43 |
| Example 2 | 10 | 313 | 26 |
| Example 23 | 10 | 382 | 28 |
| Example 32 | 10 | 402 | 30 |
| Example 42 | 10 | 308 | 27 |

Experimental Example 5

Triglyceride Accumulation Promoting Action in 3T3-L1 cells

A culture medium of 80% confluent 3T3-L1 cells was removed and the cells were dissociated with 0.25% trypsin-EDTA solution. 5% FBS-DMEM (the same amount as the removed medium) was added and the obtained cell suspension was centrifuged at 25° C., 100×g for 1 min to give cell sediment and the supernatant was removed. The cells were re-suspended in a suitable amount of 5% FBS-DMEM medium and the cells were counted. 5% FBS-DMEM medium was added to adjust the concentration to $1\times10^5$ cells/ml and the mixture was dispensed by 1 ml to a 24 well plate. The cells were cultured with aeration of 5% $CO_2$ at 37° C. for 2 days. Upon confirmation of a post-confluent state, the culture supernatant was changed to a medium containing 0.5 mM-IBMX, and the cells were cultured for 2 days. Then, the medium was changed to a medium containing 10 ng/ml insulin and $10^{-7}$ M test compound and the cells were cultured further for 4 days. After removing the culture supernatant, the cells were lysed in a 0.1% SDS solution and the triglyceride amount was measured. The triglyceride accumulation (%) due to the potentiation of insulin activity by the test compound was calculated from the following formula. The results are shown in Table 5.

[(triglyceride amount with addition of test compound−triglyceride amount of control)/triglyceride amount of control]×100

TABLE 5

Triglyceride accumulation promoting action

| Test compound | Triglyceride accumulation (%) |
|---|---|
| Example 2 | 260.4 |
| Example 5 | 233.0 |
| Example 8 | 275.5 |
| Example 16 | 288.9 |
| Example 21 | 284.9 |
| Example 23 | 214.2 |

TABLE 5-continued

Triglyceride accumulation promoting action

| Test compound | Triglyceride accumulation (%) |
|---|---|
| Example 32 | 181.2 |
| Example 33 | 222.5 |
| Example 37 | 277.3 |
| Example 39 | 258.0 |
| Example 40 | 231.0 |
| Example 42 | 193.6 |
| Example 62 | 327.8 |

EFFECT OF THE INVENTION

The heterocyclic compound [I] and a pharmaceutically acceptable salt of the present invention show a superior hypoglycemic action, a blood hypolipidemic action, an insulin resistance-improving action and a PPAR activating action and are useful as hypoglycemic agents, hypolipidemic agents, insulin resistance improvers, therapeutic agents of diabetes, therapeutic agents of diabetic complications, glucose tolerance improvers, anti-atherosclerosis agents, anti-obesity agents, antiinflammatory agents, agents for the prophylaxis or treatment of PPAR-mediated disease and agents for the prophylaxis or treatment of syndrome X. Therefore, the heterocyclic compound [I] and a pharmaceutically acceptable salt of the present invention are useful for the prophylaxis or treatment of diabetes, diabetic complications, hyperlipidemia, atherosclerosis, hyperglycemia, diseases caused by insulin resistant impaired glucose tolerance and diseases caused by insulin resistance, obesity, inflammation, PPAR-mediated disease and syndrome X. The heterocyclic compound [I] of the present invention has a structure completely different from the structure of the compounds heretofore used as an active ingredient of conventional insulin resistance improvers. By the provision of this compound, hypoglycemic agents, hypolipidemic agents, insulin resistance improvers, therapeutic agents of diabetes, therapeutic agents of diabetic complications, glucose tolerance improvers, anti-atherosclerosis agents, anti-obesity agents, antiinflammatory agents, agents for the prophylaxis or treatment of PPAR-mediated disease and agents for the prophylaxis or treatment of syndrome X come to have a wide variety, from which a desired agent can be freely selected.

This application is based on patent application Nos. 345543/1999 and 295108/2000 filed in Japan, the contents of which are hereby incorporated by reference.

What is claimed is:
1. A heterocyclic compound of the formula [I]:

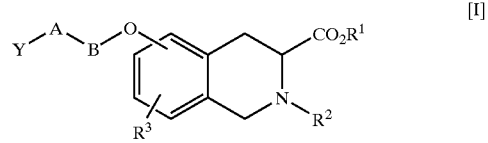

wherein
$R^1$ is hydrogen atom or lower alkyl,
$R^2$ is alkyl optionally having a substituent, cycloalkyl, cycloalkylalkyl, aryl optionally having a substituent, arylalkyl optionally having a substituent, alkenyl optionally having a substituent, alkynyl optionally having a substituent, heterocyclic alkyl optionally having a substituent or

—$COR^4$ wherein $R^4$ is $C_{4-8}$ alkyl optionally having a substituent, or alkenyl optionally having a substituent, R³ is hydrogen atom, lower alkyl or lower alkoxy,
A is a single bond or >N—R⁵
wherein R⁵ is hydrogen atom or lower alkyl,
B is lower alkylene, and
Y is an aromatic heterocyclic residue optionally having a substituent, or a pharmaceutically acceptable salt thereof.

2. The heterocyclic compound of claim 1, wherein, in the formula [I],

R¹ is hydrogen atom or lower alkyl,
R² is alkyl optionally having a substituent, cycloalkyl, cycloalkylalkyl, aryl optionally having a substituent, arylalkyl optionally having a substituent or —COR⁴ wherein R⁴ is C₄₋₈ alkyl optionally having a substituent,
R³ is hydrogen atom, lower alkyl or lower alkoxy,
A is a single bond or >N—R⁵ wherein R⁵ is hydrogen atom or lower alkyl,
B is lower alkylene, and
Y is an aromatic heterocyclic residue optionally having a substituent, or a pharmaceutically acceptable salt thereof.

3. The heterocyclic compound of claim 1, wherein, in the formula [I],

R¹ is hydrogen atom or lower alkyl,
R² is alkyl, cycloalkylalkyl, arylalkyl optionally having a substituent, alkenyl, alkynyl, heterocyclic alkyl or —COR⁴ wherein R⁴ is C₄₋₈ alkyl or alkenyl,
R³ is hydrogen atom or lower alkoxy,
A is a single bond or >N—R⁵ wherein R⁵ is lower alkyl,
B is lower alkylene, and
Y is an aromatic heterocyclic residue optionally having a substituent, or a pharmaceutically acceptable salt thereof.

4. The heterocyclic compound of claim 1, wherein, in the formula [I],

R¹ is hydrogen atom or lower alkyl,
R² is alkyl, cycloalkylalkyl, arylalkyl optionally having a substituent or —COR⁴ wherein R⁴ is C₄₋₈ alkyl,
R³ is hydrogen atom,
A is a single bond or >N—R⁵ wherein R⁵ is lower alkyl,
B is lower alkylene, and
Y is an aromatic heterocyclic residue optionally having a substituent, or a pharmaceutically acceptable salt thereof.

5. The heterocyclic compound of claim 1, wherein, in the formula [I], Y—A— is

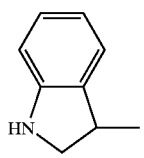 , 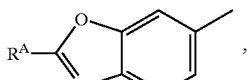 ,

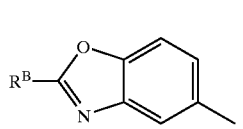 , 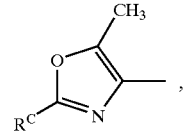 ,

-continued

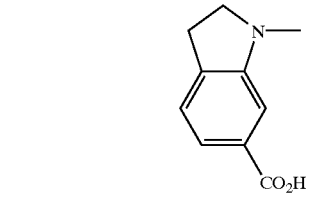

wherein
R^A is isopropyl or tert-butyl,
R^B is isopropyl or tert-butyl,
R^C is isopropyl, tert-butyl, phenyl, thiophen-2-yl, 2-methylpropenyl, 3-butenyl, cyclopropyl, 1-butenyl or 2,2-dimethylpropyl, or a pharmaceutically acceptable salt thereof.

6. The heterocyclic compound of claim 1, wherein, in the formula [I], Y—A— is

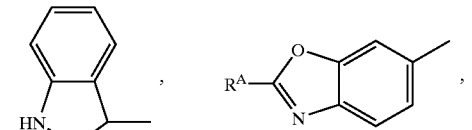

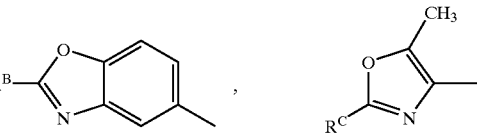

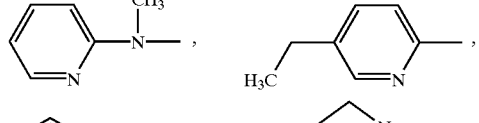

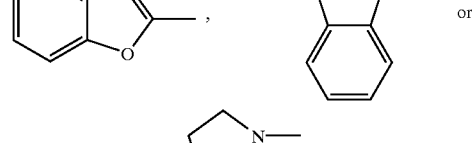

wherein
R^A is isopropyl or tert-butyl,
R^B is isopropyl or tert-butyl,
R^C is isopropyl, tert-butyl, phenyl, thiophen-2-yl, 2-methylpropenyl or 3-butenyl, or a pharmaceutically acceptable salt thereof.

7. The heterocyclic compound of claim 1, wherein, in the formula [I],
Y—A— is

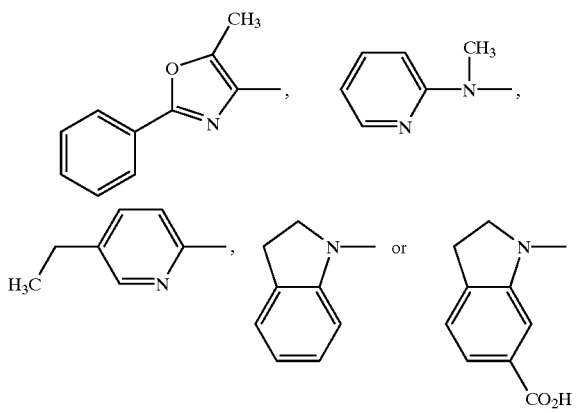

or a pharmaceutically acceptable salt thereof.

8. The heterocyclic compound of claim 1, wherein, in the formula [I],
Y—A— is

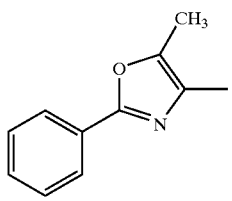

or a pharmaceutically acceptable salt thereof.

9. The heterocyclic compound of claim 1, wherein the heterocyclic compound of the formula [I] is any of the following compounds (1) to (60):

(1) 2-benzyl-7-[2-(5-methyl-2-phenyloxazol-4-yl)ethoxy]-1,2,3,4-tetrahydroisoquinoline-(3S)-carboxylic acid, (2) 2-methyl-7-[2-(5-methyl-2-phenyloxazol-4-yl)ethoxy]-1,2,3,4-tetrahydroisoquinoline-(3S)-carboxylic acid, (3) 2-hexanoyl-7-[2-(5-methyl-2-phenyloxazol-4-yl)ethoxy]-1,2,3,4-tetrahydroisoquinoline-(3S)-carboxylic acid, (4) 2-hexyl-7-[2-(5-methyl-2-phenyloxazol-4-yl)ethoxy]-1,2,3,4-tetrahydroisoquinoline-(3S)-carboxylic acid, (5) 2-isobutyl-7-[2-(5-methyl-2-phenyloxazol-4-yl)ethoxy]-1,2,3,4-tetrahydroisoquinoline-(3S)-carboxylic acid, (6) 2-cyclohexylmethyl-7-[2-(5-methyl-2-phenyloxazol-4-yl)ethoxy]-1,2,3,4-tetrahydroisoquinoline-(3S)-carboxylic acid, (7) 7-[2-(5-methyl-2-phenyloxazol-4-yl)ethoxy]-2-(3-phenylpropyl)-1,2,3,4-tetrahydroisoquinoline-(3S)-carboxylic acid, (8) 2-benzyl-7-[2-(N-methyl-N-(pyridin-2-yl)amino)ethoxy]-1,2,3,4-tetrahydroisoquinoline-(3S)-carboxylic acid, (9) 2-benzyl-7-[2-(5-ethyl-pyridin-2-yl)ethoxy]-1,2,3,4-tetrahydroisoquinoline-(3S)-carboxylic acid,

(10) 2-benzyl-7-[2-(indolin-1-yl)ethoxy]-1,2,3,4-tetrahydroisoquinoline-(3S)-carboxylic acid,

(11) ethyl 2-benzyl-7-[2-(5-methyl-2-phenyloxazol-4-yl)ethoxy]-1,2,3,4-tetrahydroisoquinoline-(3S)-carboxylate,

(12) 2-(4-methoxybenzyl)-7-[2-(5-methyl-2-phenyloxazol-4-yl)ethoxy]-1,2,3,4-tetrahydroisoquinoline-(3S)-carboxylic acid,

(13) ethyl 2-(4-methoxybenzyl)-7-[2-(5-methyl-2-phenyloxazol-4-yl)ethoxy]-1,2,3,4-tetrahydroisoquinoline-(3S)-carboxylate,

(14) 2-(4-methylbenzyl)-7-[2-(5-methyl-2-phenyloxazol-4-yl)ethoxy]-1,2,3,4-tetrahydroisoquinoline-(3S)-carboxylic acid,

(15) ethyl 2-(4-methylbenzyl)-7-[2-(5-methyl-2-phenyloxazol-4-yl)ethoxy]-1,2,3,4-tetrahydroisoquinoline-(3S)-carboxylate,

(16) 2-benzyl-7-[2-(6-carboxyindolin-1-yl)ethoxy]-1,2,3,4-tetrahydroisoquinoline-(3S)-carboxylic acid,

(17) 2-(4-fluorobenzyl)-7-[2-(5-methyl-2-phenyloxazol-4-yl)ethoxy]-1,2,3,4-tetrahydroisoquinoline-(3S)-carboxylic acid,

(18) 2-(2,2-dimethylpropionyl)-7-[2-(5-methyl-2-phenyloxazol-4-yl)ethoxy]-1,2,3,4-tetrahydroisoquinoline-(3S)-carboxylic acid,

(19) 2-(2,2-dimethylpropyl)-7-[2-(5-methyl-2-phenyloxazol-4-yl)ethoxy]-1,2,3,4-tetrahydroisoquinoline-(3S)-carboxylic acid,

(20) 2-benzyl-7-[2-(5-methyl-2-tert-butyloxazol-4-yl)ethoxy]-1,2,3,4-tetrahydroisoquinoline-(3S)-carboxylic acid,

(21) 2-benzyl-7-[2-(5-methyl-2-(thiophen-2-yl)oxazol-4-yl)ethoxy]-1,2,3,4-tetrahydroisoquinoline-(3S)-carboxylic acid,

(22) 2-benzyl-7-[2-(5-methyl-2-isopropyloxazol-4-yl)ethoxy]-1,2,3,4-tetrahydroisoquinoline-(3S)-carboxylic acid,

(23) 2-butyl-7-[2-(5-methyl-2-phenyloxazol-4-yl)ethoxy]-1,2,3,4-tetrahydroisoquinoline-(3S)-carboxylic acid,

(24) 2-benzyl-7-{2-[5-methyl-2-(2-methylpropenyl)oxazol-4-yl]ethoxy}-1,2,3,4-tetrahydroisoquinoline-(3S)-carboxylic acid,

(25) 2-benzyl-7-{2-[2-(3-butenyl)-5-methyloxazol-4-yl]ethoxy}-1,2,3,4-tetrahydroisoquinoline-(3S)-carboxylic acid,

(26) 2-allyl-7-[2-(5-methyl-2-phenyloxazol-4-yl)ethoxy]-1,2,3,4-tetrahydroisoquinoline-(3S)-carboxylic acid,

(27) 7-[2-(5-methyl-2-phenyloxazol-4-yl)ethoxy]-2-(2-propynyl)-1,2,3,4-tetrahydroisoquinoline-(3S)-carboxylic acid,

(28) 2-(2-butenyl)-7-[2-(5-methyl-2-phenyloxazol-4-yl)ethoxy]-1,2,3,4-tetrahydroisoquinoline-(3S)-carboxylic acid,

(29) 2-benzyl-7-[(indolin-3-yl)ethoxy]-1,2,3,4-tetrahydroisoquinoline-(3S)-carboxylic acid,

(30) 2-(3-butenyl)-7-[2-(5-methyl-2-phenyloxazol-4-yl)ethoxy]-1,2,3,4-tetrahydroisoquinoline-(3S)-carboxylic acid,

(31) 7-[2-(5-methyl-2-phenyloxazol-4-yl)ethoxy]-2-pentanoyl-1,2,3,4-tetrahydroisoquinoline-(3S)-carboxylic acid,

(32) 7-[2-(5-methyl-2-phenyloxazol-4-yl)ethoxy]-2-(4-pentenoyl)-1,2,3,4-tetrahydroisoquinoline-(3S)-carboxylic acid,

(33) 2-(3-methyl-2-butenoyl)-7-[2-(5-methyl-2-phenyloxazol-4-yl)ethoxy]-1,2,3,4-tetrahydroisoquinoline-(3S)-carboxylic acid,

(34) 2-(3,3-dimethylbutyryl)-7-[2-(5-methyl-2-phenyloxazol-4-yl)ethoxy]-1,2,3,4-tetrahydroisoquinoline-(3S)-carboxylic acid,

(35) 2-benzyl-7-methoxy-6-[2-(5-methyl-2-phenyloxazol-4-yl)ethoxy]-1,2,3,4-tetrahydroisoquinoline-(3RS)-carboxylic acid,

(36) 7-[2-(5-methyl-2-phenyloxazol-4-yl)ethoxy]-2-(pyridin-2-ylmethyl)-1,2,3,4-tetrahydroisoquinoline-(3S)-carboxylic acid,

(37) 2-benzyl-7-(2-isopropylbenzoxazol-6-yl)methoxy-1,2,3,4-tetrahydroisoquinoline-(3S)-carboxylic acid,

(38) 2-benzyl-7-(2-tert-butylbenzoxazol-6-yl)methoxy-1,2,3,4-tetrahydroisoquinoline-(3S)-carboxylic acid,

(39) 2-benzyl-7-(2-tert-butylbenzoxazol-5-yl)methoxy-1,2,3,4-tetrahydroisoquinoline-(3S)-carboxylic acid,

(40) 7-(2-tert-butylbenzoxazol-6-yl)methoxy-2-(2,2-dimethylpropyl)-1,2,3,4-tetrahydroisoquinoline-(3S)-carboxylic acid,

(41) 2-benzyl-7-(2-isopropylbenzoxazol-5-yl)methoxy-1,2,3,4-tetrahydroisoquinoline-(3S)-carboxylic acid,

(42) 7-[2-(5-methyl-2-phenyloxazol-4-yl)ethoxy]-2-(pyridin-4-ylmethyl)-1,2,3,4-tetrahydroisoquinoline-(3S)-carboxylic acid,

(43) methyl 2-benzyl-7-[2-(5-methyl-2-phenyloxazol-4-yl)ethoxy]-1,2,3,4-tetrahydroisoquinoline-(3S)-carboxylate,

(44) 2-benzyl-7-[2-(2-cyclopropyl-5-methyloxazol-4-yl)ethoxy]-1,2,3,4-tetrahydroisoquinoline-(3S)-carboxylic acid,

(45) 2-(3-methyl-2-butenyl)-7-[2-(5-methyl-2-phenyloxazol-4-yl)ethoxy]-1,2,3,4-tetrahydroisoquinoline-(3S)-carboxylic acid,

(46) 2-(2,2-dimethylpropyl)-7-[2-(5-methyl-2-tert-butyloxazol-4-yl)ethoxy]-1,2,3,4-tetrahydroisoquinoline-(3S)-carboxylic acid,

(47) 2-benzyl-7-{2-[2-(1-butenyl)-5-methyloxazol-4-yl]ethoxy}-1,2,3,4-tetrahydroisoquinoline-(3S)-carboxylic acid,

(48) 2-benzyl-7-{2-[2-(2,2-dimethylpropyl)-5-methyloxazol-4-yl]ethoxy}-1,2,3,4-tetrahydroisoqinoline-(3S)-carboxylic acid,

(49) ethyl 2-(2,2-dimethylpropyl)-7-[2-(5-methyl-2-phenyloxazol-4-yl)ethoxy]-1,2,3,4-tetrahydroisoquinoline-(3S)-carboxylate,

(50) 7-(benzofran-2-ylmethoxy)-2-benzyl-1,2,3,4-tetrahydroisoquinoline-(3S)-carboxylic acid,

(51) 2-isobutyryl-7-[2-(5-methyl-2-phenyloxazol-4-yl)ethoxy]-1,2,3,4-tetrahydroisoquinoline-(3S)-carboxylic acid,

(52) 7-[2-(benzofran-2-yl)ethoxy]-2-benzyl-1,2,3,4-tetrahydroisoquinoline-(3S)-carboxylic acid,

(53) 7-[2-(5-ethylpyridin-2-yl)ethoxy]-2-hexanoyl-1,2,3,4-tetrahydroisoquinoline-(3S)-carboxylic acid,

(54) 2-carboxymethyl-7-[2-(5-methyl-2-phenyloxazol-4-yl)ethoxy]-1,2,3,4-tetrahydroisoquinoline-(3S)-carboxylic acid,

(55) 2-[3-(methoxycarbonyl)propionyl]-7-[2-(5-methyl-2-phenyloxazol-4-yl)ethoxy]-1,2,3,4-tetrahydroisoquinoline-(3S)-carboxylic acid,

(56) 2-[3-(ethoxycarbonyl)propyl]-7-[2-(5-methyl-2-phenyloxazol-4-yl)ethoxy]-1,2,3,4-tetrahydroisoquinoline-(3S)-carboxylic acid,

(57) 2-benzyl-6-[2-(5-methyl-2-phenyloxazol-4-yl)ethoxy]-1,2,3,4-tetrahydroisoquinoline-(3RS)-carboxylic acid,

(58) 2-(3-acetylbenzyl)-7-[2-(5-methyl-2-phenyloxazol-4-yl)ethoxy]-1,2,3,4-tetrahydroisoquinoline-(3S)-carboxylic acid,

(59) 2-(2-acetylbenzyl)-7-[2-(5-methyl-2-phenyloxazol-4-yl)ethoxy]-1,2,3,4-tetrahydroisoquinoline-(3S)-carboxylic acid, and

(60) 2-benzyl-7-[(5-methyl-2-phenyloxazol-4-yl)methoxy]-1,2,3,4-tetrahydroisoquinoline-(3S)-carboxylic acid, or a pharmaceutically acceptable salt thereof.

10. The heterocyclic compound of claim 9, wherein the heterocyclic compound of the formula [I] is any of the above-mentioned compounds (1) to (41), or a pharmaceutically acceptable salt thereof.

11. The heterocyclic compound of claim 9, wherein the heterocyclic compound of the formula [I] is any of the above-mentioned compounds (1) to (17), or a pharmaceutically acceptable salt thereof.

12. A pharmaceutical composition comprising the heterocyclic compound of claim 1 or a pharmaceutically acceptable salt thereof.

13. A pharmaceutical agent comprising the heterocyclic compound of claim 1 or a pharmaceutically acceptable salt thereof, which is selected from the group consisting of a hypoglycemic agent, a hypolipidemic agent, an insulin resistance improver, a therapeutic agent of diabetes, a therapeutic agent of diabetic complication, a glucose tolerance improver, an anti-atherosclerosis agent, an anti-obesity agent, an antiinflammatory agent, an agent for the prophylaxis or treatment of PPAR-mediated disease and an agent for the prophylaxis or treatment of syndrome X.

14. A hypoglycemic agent comprising the heterocyclic compound of claim 1 or a pharmaceutically acceptable salt thereof.

15. A hypolipidemic agent comprising the heterocyclic compound of claim 1 or a pharmaceutically acceptable salt thereof.

16. An insulin resistance improver comprising the heterocyclic compound of claim 1 or a pharmaceutically acceptable salt thereof.

17. A therapeutic agent of diabetic complication comprising the heterocyclic compound of claim 1 or a pharmaceutically acceptable salt thereof.

18. A therapeutic agent of diabetes comprising the heterocyclic compound of claim 1 or a pharmaceutically acceptable salt thereof.

* * * * *